(12) United States Patent
Hestir et al.

(10) Patent No.: US 8,404,810 B2
(45) Date of Patent: Mar. 26, 2013

(54) COMPOSITIONS AND METHODS OF USE FOR MODULATORS OF POLYPEPTIDES AND POLYNUCLEOTIDES IN TREATING BREAST CANCER AND MELANOMA

(75) Inventors: Kevin Hestir, Kensington, CA (US); Justin Wong, Oakland, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 525 days.

(21) Appl. No.: 12/279,703

(22) PCT Filed: Feb. 20, 2007

(86) PCT No.: PCT/US2007/004255
§ 371 (c)(1),
(2), (4) Date: Aug. 30, 2010

(87) PCT Pub. No.: WO2007/098093
PCT Pub. Date: Aug. 30, 2007

(65) Prior Publication Data
US 2010/0324270 A1    Dec. 23, 2010

Related U.S. Application Data

(60) Provisional application No. 60/774,238, filed on Feb. 17, 2006, provisional application No. 60/774,268, filed on Feb. 17, 2006, provisional application No. 60/796,852, filed on May 3, 2006.

(51) Int. Cl.
*C07K 14/00* (2006.01)
(52) U.S. Cl. ............... 530/387.1; 530/387.7; 530/387.3
(58) Field of Classification Search .................. None
See application file for complete search history.

(56) References Cited

PUBLICATIONS

Greenbaum et al, Genome Biology vol. 4 p. 117 (2003).*

* cited by examiner

*Primary Examiner* — Sheela J Huff
(74) *Attorney, Agent, or Firm* — Anna L. Barry

(57) ABSTRACT

This invention relates to the polynucleotides and the encoded polypeptides, including novel sequences, of human or non-human primate genes that are amplified in breast and/or other tumor tissues melanoma, as compared to the corresponding normal tissue. The invention also relates to modulators of such polynucleotides and polypeptides, for example, antibodies, that specifically bind to and/or interfere with the activity of this polypeptide, polynucleotide, its fragments, variants, and antagonists. The invention further relates to compositions containing such a polypeptide, polynucleotide, or modulators thereof and uses of such compositions in methods of treating or preventing cancer, by detecting this polynucleotide, polypeptide, or antibodies thereto in patient samples. The invention also provides diagnostic tests for breast cancer and melanoma, by identifying polypeptides and polynucleotides encoded by the cDNA sequence of the invention that correlate with those disorders.

6 Claims, 11 Drawing Sheets

```
CLN004    MELPSHTQDSLVKLKGKFKLSIFIYEVVTLSLSLQIAQSGVLWFLLSHSPARKNLSFEFLKCIISSPPQTTCIPVSHLKGEMVI
          ++++++++++++++++++++++++++++++++++++++++++ +++++++++++++++++++++++ +++++++++++++++++
          ++++++++++++++++++++++++++++++++++++++++++ +++++++++++++++++++++++ +++++++++++++++++
chimp_    MELPSHTQDSLVKLKGKFKLSIFIYEVVTLSLSLQIAQSGVLWFLLSYSPARKNLSFEFLKCIISSRPQTTCIPVSHLKGEMVI
```

Fig. 8

SEQUENCE LISTING

<160> NUMBER OF SEQ ID NOS: 372

<210> SEQ ID NO 1
<211> LENGTH: 393
<212> TYPE: DNA
<213> ORGANISM: Homo sapiens

<400> SEQUENCE: 1

```
atgattttc cccctcttc acgggatcag agggaactaa tagaatgtga caatgattct    60
ttagcaggga ctgctgaggc ttctggttcc ttttaagat ctgcagtgaa agaagatgag   120
aaacatggat atgcccttct tttggtcccc ctcttccttt atttgatctc tacttccttc   180
tataaatata ttagggctac attgtcccct tgtatttcaa acaaggcaaa aagaggttgt   240
aattacactt tactgcaatc ctcagtttct ccagggaaca ggaatgcaaa ggctttgaag   300
gcctctctat ttgctgacat ggtcagctgg gtgccatggg ccaagtcctt ctgttgccct   360
cctctgtcac caagtaagct aggtcctttc tga                               393
```

<210> SEQ ID NO 2
<211> LENGTH: 123
<212> TYPE: DNA
<213> ORGANISM: Homo sapiens

<400> SEQUENCE: 2

```
atgattttc cccctcttc acgggatcag agggaactaa tagaatgtga caatgattct    60
ttagcaggga ctgctgaggc ttctggttcc ttttaagat ctgcagtgaa agaagatgag   120
aaa                                                                123
```

<210> SEQ ID NO 3
<211> LENGTH: 198
<212> TYPE: DNA
<213> ORGANISM: Homo sapiens

<400> SEQUENCE: 3

```
agggctacat tgtcccttg tatttcaaac aaggcaaaaa gaggttgtaa ttacactta    60 ctgcaatcct cagtttctcc agggaacagg aatgcaaagg ctttgaaggc ctctctattt   120
gctgacatgg tcagctgggt gccatgggcc aagtccttct gttgccctcc tctgtcacca   180
agtaagctag gtcctttc                                                198
```

<210> SEQ ID NO 4
<211> LENGTH: 130
<212> TYPE: PRT
<213> ORGANISM: Homo sapiens

<400> SEQUENCE: 4

```
Met Ile Phe Pro Pro Ser Ser Arg Asp Gln Arg Glu Leu Ile Glu Cys
 1               5                  10                  15

Asp Asn Asp Ser Leu Ala Gly Thr Ala Glu Ala Ser Gly Ser Phe Leu
            20                  25                  30

Arg Ser Ala Val Lys Glu Asp Glu Lys His Gly Tyr Ala Leu Leu Leu
        35                  40                  45

Val Pro Leu Phe Leu Tyr Leu Ile Ser Thr Ser Phe Tyr Lys Tyr Ile
    50                  55                  60

Arg Ala Thr Leu Ser Leu Cys Ile Ser Asn Lys Ala Lys Arg Gly Cys
65                  70                  75                  80

Asn Tyr Thr Leu Leu Gln Ser Ser Val Ser Pro Gly Asn Arg Asn Ala
                85                  90                  95

Lys Ala Leu Lys Ala Ser Leu Phe Ala Asp Met Val Ser Trp Val Pro
           100                 105                 110

Trp Ala Lys Ser Phe Cys Cys Pro Pro Leu Ser Pro Ser Lys Leu Gly
           115                 120                 125

Pro Phe
   130
```

```
<210> SEQ ID NO 5
<211> LENGTH: 41
<212> TYPE: PRT
<213> ORGANISM: Homo sapiens

<400> SEQUENCE: 5

Met Ile Phe Pro Pro Ser Ser Arg Asp Gln Arg Glu Leu Ile Glu Cys
1               5                   10                  15

Asp Asn Asp Ser Leu Ala Gly Thr Ala Glu Ala Ser Gly Ser Phe Leu
            20                  25                  30

Arg Ser Ala Val Lys Glu Asp Glu Lys
        35                  40

<210> SEQ ID NO 6
<211> LENGTH: 66
<212> TYPE: PRT
<213> ORGANISM: Homo sapiens

<400> SEQUENCE: 6

Arg Ala Thr Leu Ser Leu Cys Ile Ser Asn Lys Ala Lys Arg Gly Cys
1               5                   10                  15

Asn Tyr Thr Leu Leu Gln Ser Ser Val Ser Pro Gly Asn Arg Asn Ala
            20                  25                  30

Lys Ala Leu Lys Ala Ser Leu Phe Ala Asp Met Val Ser Trp Val Pro
        35                  40                  45

Trp Ala Lys Ser Phe Cys Cys Pro Leu Ser Pro Ser Lys Leu Gly
    50                  55                  60

Pro Phe
65

<210> SEQ ID NO 7
<211> LENGTH: 6
<212> TYPE: PRT
<213> ORGANISM: Homo sapiens

<400> SEQUENCE: 7

Met Ile Phe Pro Pro Ser
1               5

<210> SEQ ID NO 8
<211> LENGTH: 6
<212> TYPE: PRT
<213> ORGANISM: Homo sapiens

<400> SEQUENCE: 8

Ile Phe Pro Pro Ser Ser
1               5

<210> SEQ ID NO 9
<211> LENGTH: 6
<212> TYPE: PRT
<213> ORGANISM: Homo sapiens

<400> SEQUENCE: 9

Phe Pro Pro Ser Ser Arg
1               5

<210> SEQ ID NO 10
<211> LENGTH: 6
<212> TYPE: PRT
<213> ORGANISM: Homo sapiens

<400> SEQUENCE: 10
```

```
Pro Pro Ser Ser Arg Asp
1               5

<210> SEQ ID NO 11
<211> LENGTH: 6
<212> TYPE: PRT
<213> ORGANISM: Homo sapiens

<400> SEQUENCE: 11

Pro Ser Ser Arg Asp Gln
1               5

<210> SEQ ID NO 12
<211> LENGTH: 6
<212> TYPE: PRT
<213> ORGANISM: Homo sapiens

<400> SEQUENCE: 12

Ser Ser Arg Asp Gln Arg
1               5

<210> SEQ ID NO 13
<211> LENGTH: 6
<212> TYPE: PRT
<213> ORGANISM: Homo sapiens

<400> SEQUENCE: 13

Ser Arg Asp Gln Arg Glu
1               5

<210> SEQ ID NO 14
<211> LENGTH: 6
<212> TYPE: PRT
<213> ORGANISM: Homo sapiens

<400> SEQUENCE: 14

Arg Asp Gln Arg Glu Leu
1               5

<210> SEQ ID NO 15
<211> LENGTH: 6
<212> TYPE: PRT
<213> ORGANISM: Homo sapiens

<400> SEQUENCE: 15

Asp Gln Arg Glu Leu Ile
1               5

<210> SEQ ID NO 16
<211> LENGTH: 6
<212> TYPE: PRT
<213> ORGANISM: Homo sapiens

<400> SEQUENCE: 16

Gln Arg Glu Leu Ile Glu
1               5

<210> SEQ ID NO 17
<211> LENGTH: 6
<212> TYPE: PRT
<213> ORGANISM: Homo sapiens

<400> SEQUENCE: 17

Arg Glu Leu Ile Glu Cys
1               5
```

```
<210> SEQ ID NO 18
<211> LENGTH: 6
<212> TYPE: PRT
<213> ORGANISM: Homo sapiens

<400> SEQUENCE: 18

Glu Leu Ile Glu Cys Asp
1               5

<210> SEQ ID NO 19
<211> LENGTH: 6
<212> TYPE: PRT
<213> ORGANISM: Homo sapiens

<400> SEQUENCE: 19

Leu Ile Glu Cys Asp Asn
1               5

<210> SEQ ID NO 20
<211> LENGTH: 6
<212> TYPE: PRT
<213> ORGANISM: Homo sapiens

<400> SEQUENCE: 20

Ile Glu Cys Asp Asn Asp
1               5

<210> SEQ ID NO 21
<211> LENGTH: 6
<212> TYPE: PRT
<213> ORGANISM: Homo sapiens

<400> SEQUENCE: 21

Glu Cys Asp Asn Asp Ser
1               5

<210> SEQ ID NO 22
<211> LENGTH: 6
<212> TYPE: PRT
<213> ORGANISM: Homo sapiens

<400> SEQUENCE: 22

Cys Asp Asn Asp Ser Leu
1               5

<210> SEQ ID NO 23
<211> LENGTH: 6
<212> TYPE: PRT
<213> ORGANISM: Homo sapiens

<400> SEQUENCE: 23

Asp Asn Asp Ser Leu Ala
1               5

<210> SEQ ID NO 24
<211> LENGTH: 6
<212> TYPE: PRT
<213> ORGANISM: Homo sapiens

<400> SEQUENCE: 24

Asn Asp Ser Leu Ala Gly
1               5

<210> SEQ ID NO 25
<211> LENGTH: 6
```

```
<212> TYPE: PRT
<213> ORGANISM: Homo sapiens

<400> SEQUENCE: 25

Asp Ser Leu Ala Gly Thr
1               5

<210> SEQ ID NO 26
<211> LENGTH: 6
<212> TYPE: PRT
<213> ORGANISM: Homo sapiens

<400> SEQUENCE: 26

Ser Leu Ala Gly Thr Ala
1               5

<210> SEQ ID NO 27
<211> LENGTH: 6
<212> TYPE: PRT
<213> ORGANISM: Homo sapiens

<400> SEQUENCE: 27

Leu Ala Gly Thr Ala Glu
1               5

<210> SEQ ID NO 28
<211> LENGTH: 6
<212> TYPE: PRT
<213> ORGANISM: Homo sapiens

<400> SEQUENCE: 28

Ala Gly Thr Ala Glu Ala
1               5

<210> SEQ ID NO 29
<211> LENGTH: 6
<212> TYPE: PRT
<213> ORGANISM: Homo sapiens

<400> SEQUENCE: 29

Gly Thr Ala Glu Ala Ser
1               5

<210> SEQ ID NO 30
<211> LENGTH: 6
<212> TYPE: PRT
<213> ORGANISM: Homo sapiens

<400> SEQUENCE: 30

Thr Ala Glu Ala Ser Gly
1               5

<210> SEQ ID NO 31
<211> LENGTH: 6
<212> TYPE: PRT
<213> ORGANISM: Homo sapiens

<400> SEQUENCE: 31

Ala Glu Ala Ser Gly Ser
1               5

<210> SEQ ID NO 32
<211> LENGTH: 6
<212> TYPE: PRT
<213> ORGANISM: Homo sapiens
```

```
<400> SEQUENCE: 32

Glu Ala Ser Gly Ser Phe
1               5

<210> SEQ ID NO 33
<211> LENGTH: 6
<212> TYPE: PRT
<213> ORGANISM: Homo sapiens

<400> SEQUENCE: 33

Ala Ser Gly Ser Phe Leu
1               5

<210> SEQ ID NO 34
<211> LENGTH: 6
<212> TYPE: PRT
<213> ORGANISM: Homo sapiens

<400> SEQUENCE: 34

Ser Gly Ser Phe Leu Arg
1               5

<210> SEQ ID NO 35
<211> LENGTH: 6
<212> TYPE: PRT
<213> ORGANISM: Homo sapiens

<400> SEQUENCE: 35

Gly Ser Phe Leu Arg Ser
1               5

<210> SEQ ID NO 36
<211> LENGTH: 6
<212> TYPE: PRT
<213> ORGANISM: Homo sapiens

<400> SEQUENCE: 36

Ser Phe Leu Arg Ser Ala
1               5

<210> SEQ ID NO 37
<211> LENGTH: 6
<212> TYPE: PRT
<213> ORGANISM: Homo sapiens

<400> SEQUENCE: 37

Phe Leu Arg Ser Ala Val
1               5

<210> SEQ ID NO 38
<211> LENGTH: 6
<212> TYPE: PRT
<213> ORGANISM: Homo sapiens

<400> SEQUENCE: 38

Leu Arg Ser Ala Val Lys
1               5

<210> SEQ ID NO 39
<211> LENGTH: 6
<212> TYPE: PRT
<213> ORGANISM: Homo sapiens

<400> SEQUENCE: 39

Arg Ser Ala Val Lys Glu
```

<210> SEQ ID NO 40
<211> LENGTH: 6
<212> TYPE: PRT
<213> ORGANISM: Homo sapiens

<400> SEQUENCE: 40

Ser Ala Val Lys Glu Asp
1               5

<210> SEQ ID NO 41
<211> LENGTH: 6
<212> TYPE: PRT
<213> ORGANISM: Homo sapiens

<400> SEQUENCE: 41

Ala Val Lys Glu Asp Glu
1               5

<210> SEQ ID NO 42
<211> LENGTH: 6
<212> TYPE: PRT
<213> ORGANISM: Homo sapiens

<400> SEQUENCE: 42

Val Lys Glu Asp Glu Lys
1               5

<210> SEQ ID NO 43
<211> LENGTH: 6
<212> TYPE: PRT
<213> ORGANISM: Homo sapiens

<400> SEQUENCE: 43

Arg Ala Thr Leu Ser Leu
1               5

<210> SEQ ID NO 44
<211> LENGTH: 6
<212> TYPE: PRT
<213> ORGANISM: Homo sapiens

<400> SEQUENCE: 44

Ala Thr Leu Ser Leu Cys
1               5

<210> SEQ ID NO 45
<211> LENGTH: 6
<212> TYPE: PRT
<213> ORGANISM: Homo sapiens

<400> SEQUENCE: 45

Thr Leu Ser Leu Cys Ile
1               5

<210> SEQ ID NO 46
<211> LENGTH: 6
<212> TYPE: PRT
<213> ORGANISM: Homo sapiens

<400> SEQUENCE: 46

Leu Ser Leu Cys Ile Ser
1               5

```
<210> SEQ ID NO 47
<211> LENGTH: 6
<212> TYPE: PRT
<213> ORGANISM: Homo sapiens

<400> SEQUENCE: 47

Ser Leu Cys Ile Ser Asn
1               5

<210> SEQ ID NO 48
<211> LENGTH: 6
<212> TYPE: PRT
<213> ORGANISM: Homo sapiens

<400> SEQUENCE: 48

Leu Cys Ile Ser Asn Lys
1               5

<210> SEQ ID NO 49
<211> LENGTH: 6
<212> TYPE: PRT
<213> ORGANISM: Homo sapiens

<400> SEQUENCE: 49

Cys Ile Ser Asn Lys Ala
1               5

<210> SEQ ID NO 50
<211> LENGTH: 6
<212> TYPE: PRT
<213> ORGANISM: Homo sapiens

<400> SEQUENCE: 50

Ile Ser Asn Lys Ala Lys
1               5

<210> SEQ ID NO 51
<211> LENGTH: 6
<212> TYPE: PRT
<213> ORGANISM: Homo sapiens

<400> SEQUENCE: 51

Ser Asn Lys Ala Lys Arg
1               5

<210> SEQ ID NO 52
<211> LENGTH: 6
<212> TYPE: PRT
<213> ORGANISM: Homo sapiens

<400> SEQUENCE: 52

Asn Lys Ala Lys Arg Gly
1               5

<210> SEQ ID NO 53
<211> LENGTH: 6
<212> TYPE: PRT
<213> ORGANISM: Homo sapiens

<400> SEQUENCE: 53

Lys Ala Lys Arg Gly Cys
1               5

<210> SEQ ID NO 54
<211> LENGTH: 6
<212> TYPE: PRT
```

<213> ORGANISM: Homo sapiens

<400> SEQUENCE: 54

Ala Lys Arg Gly Cys Asn
1               5

<210> SEQ ID NO 55
<211> LENGTH: 6
<212> TYPE: PRT
<213> ORGANISM: Homo sapiens

<400> SEQUENCE: 55

Lys Arg Gly Cys Asn Tyr
1               5

<210> SEQ ID NO 56
<211> LENGTH: 6
<212> TYPE: PRT
<213> ORGANISM: Homo sapiens

<400> SEQUENCE: 56

Arg Gly Cys Asn Tyr Thr
1               5

<210> SEQ ID NO 57
<211> LENGTH: 6
<212> TYPE: PRT
<213> ORGANISM: Homo sapiens

<400> SEQUENCE: 57

Gly Cys Asn Tyr Thr Leu
1               5

<210> SEQ ID NO 58
<211> LENGTH: 6
<212> TYPE: PRT
<213> ORGANISM: Homo sapiens

<400> SEQUENCE: 58

Cys Asn Tyr Thr Leu Leu
1               5

<210> SEQ ID NO 59
<211> LENGTH: 6
<212> TYPE: PRT
<213> ORGANISM: Homo sapiens

<400> SEQUENCE: 59

Asn Tyr Thr Leu Leu Gln
1               5

<210> SEQ ID NO 60
<211> LENGTH: 6
<212> TYPE: PRT
<213> ORGANISM: Homo sapiens

<400> SEQUENCE: 60

Tyr Thr Leu Leu Gln Ser
1               5

<210> SEQ ID NO 61
<211> LENGTH: 6
<212> TYPE: PRT
<213> ORGANISM: Homo sapiens

<400> SEQUENCE: 61

Thr Leu Leu Gln Ser Ser
1               5

<210> SEQ ID NO 62
<211> LENGTH: 6
<212> TYPE: PRT
<213> ORGANISM: Homo sapiens

<400> SEQUENCE: 62

Leu Leu Gln Ser Ser Val
1               5

<210> SEQ ID NO 63
<211> LENGTH: 6
<212> TYPE: PRT
<213> ORGANISM: Homo sapiens

<400> SEQUENCE: 63

Leu Gln Ser Ser Val Ser
1               5

<210> SEQ ID NO 64
<211> LENGTH: 6
<212> TYPE: PRT
<213> ORGANISM: Homo sapiens

<400> SEQUENCE: 64

Gln Ser Ser Val Ser Pro
1               5

<210> SEQ ID NO 65
<211> LENGTH: 6
<212> TYPE: PRT
<213> ORGANISM: Homo sapiens

<400> SEQUENCE: 65

Ser Ser Val Ser Pro Gly
1               5

<210> SEQ ID NO 66
<211> LENGTH: 6
<212> TYPE: PRT
<213> ORGANISM: Homo sapiens

<400> SEQUENCE: 66

Ser Val Ser Pro Gly Asn
1               5

<210> SEQ ID NO 67
<211> LENGTH: 6
<212> TYPE: PRT
<213> ORGANISM: Homo sapiens

<400> SEQUENCE: 67

Val Ser Pro Gly Asn Arg
1               5

<210> SEQ ID NO 68
<211> LENGTH: 6
<212> TYPE: PRT
<213> ORGANISM: Homo sapiens

<400> SEQUENCE: 68

Ser Pro Gly Asn Arg Asn
1               5

```
<210> SEQ ID NO 69
<211> LENGTH: 6
<212> TYPE: PRT
<213> ORGANISM: Homo sapiens

<400> SEQUENCE: 69

Pro Gly Asn Arg Asn Ala
1               5

<210> SEQ ID NO 70
<211> LENGTH: 6
<212> TYPE: PRT
<213> ORGANISM: Homo sapiens

<400> SEQUENCE: 70

Gly Asn Arg Asn Ala Lys
1               5

<210> SEQ ID NO 71
<211> LENGTH: 6
<212> TYPE: PRT
<213> ORGANISM: Homo sapiens

<400> SEQUENCE: 71

Asn Arg Asn Ala Lys Ala
1               5

<210> SEQ ID NO 72
<211> LENGTH: 6
<212> TYPE: PRT
<213> ORGANISM: Homo sapiens

<400> SEQUENCE: 72

Arg Asn Ala Lys Ala Leu
1               5

<210> SEQ ID NO 73
<211> LENGTH: 6
<212> TYPE: PRT
<213> ORGANISM: Homo sapiens

<400> SEQUENCE: 73

Asn Ala Lys Ala Leu Lys
1               5

<210> SEQ ID NO 74
<211> LENGTH: 6
<212> TYPE: PRT
<213> ORGANISM: Homo sapiens

<400> SEQUENCE: 74

Ala Lys Ala Leu Lys Ala
1               5

<210> SEQ ID NO 75
<211> LENGTH: 6
<212> TYPE: PRT
<213> ORGANISM: Homo sapiens

<400> SEQUENCE: 75

Lys Ala Leu Lys Ala Ser
1               5

<210> SEQ ID NO 76
```

```
<211> LENGTH: 6
<212> TYPE: PRT
<213> ORGANISM: Homo sapiens

<400> SEQUENCE: 76

Ala Leu Lys Ala Ser Leu
1               5

<210> SEQ ID NO 77
<211> LENGTH: 6
<212> TYPE: PRT
<213> ORGANISM: Homo sapiens

<400> SEQUENCE: 77

Leu Lys Ala Ser Leu Phe
1               5

<210> SEQ ID NO 78
<211> LENGTH: 6
<212> TYPE: PRT
<213> ORGANISM: Homo sapiens

<400> SEQUENCE: 78

Lys Ala Ser Leu Phe Ala
1               5

<210> SEQ ID NO 79
<211> LENGTH: 6
<212> TYPE: PRT
<213> ORGANISM: Homo sapiens

<400> SEQUENCE: 79

Ala Ser Leu Phe Ala Asp
1               5

<210> SEQ ID NO 80
<211> LENGTH: 6
<212> TYPE: PRT
<213> ORGANISM: Homo sapiens

<400> SEQUENCE: 80

Ser Leu Phe Ala Asp Met
1               5

<210> SEQ ID NO 81
<211> LENGTH: 6
<212> TYPE: PRT
<213> ORGANISM: Homo sapiens

<400> SEQUENCE: 81

Leu Phe Ala Asp Met Val
1               5

<210> SEQ ID NO 82
<211> LENGTH: 6
<212> TYPE: PRT
<213> ORGANISM: Homo sapiens

<400> SEQUENCE: 82

Phe Ala Asp Met Val Ser
1               5

<210> SEQ ID NO 83
<211> LENGTH: 6
<212> TYPE: PRT
<213> ORGANISM: Homo sapiens
```

<400> SEQUENCE: 83

Ala Asp Met Val Ser Trp
1               5

<210> SEQ ID NO 84
<211> LENGTH: 6
<212> TYPE: PRT
<213> ORGANISM: Homo sapiens

<400> SEQUENCE: 84

Asp Met Val Ser Trp Val
1               5

<210> SEQ ID NO 85
<211> LENGTH: 6
<212> TYPE: PRT
<213> ORGANISM: Homo sapiens

<400> SEQUENCE: 85

Met Val Ser Trp Val Pro
1               5

<210> SEQ ID NO 86
<211> LENGTH: 6
<212> TYPE: PRT
<213> ORGANISM: Homo sapiens

<400> SEQUENCE: 86

Val Ser Trp Val Pro Trp
1               5

<210> SEQ ID NO 87
<211> LENGTH: 6
<212> TYPE: PRT
<213> ORGANISM: Homo sapiens

<400> SEQUENCE: 87

Ser Trp Val Pro Trp Ala
1               5

<210> SEQ ID NO 88
<211> LENGTH: 6
<212> TYPE: PRT
<213> ORGANISM: Homo sapiens

<400> SEQUENCE: 88

Trp Val Pro Trp Ala Lys
1               5

<210> SEQ ID NO 89
<211> LENGTH: 6
<212> TYPE: PRT
<213> ORGANISM: Homo sapiens

<400> SEQUENCE: 89

Val Pro Trp Ala Lys Ser
1               5

<210> SEQ ID NO 90
<211> LENGTH: 6
<212> TYPE: PRT
<213> ORGANISM: Homo sapiens

<400> SEQUENCE: 90

Pro Trp Ala Lys Ser Phe
1               5

<210> SEQ ID NO 91
<211> LENGTH: 6
<212> TYPE: PRT
<213> ORGANISM: Homo sapiens

<400> SEQUENCE: 91

Trp Ala Lys Ser Phe Cys
1               5

<210> SEQ ID NO 92
<211> LENGTH: 6
<212> TYPE: PRT
<213> ORGANISM: Homo sapiens

<400> SEQUENCE: 92

Ala Lys Ser Phe Cys Cys
1               5

<210> SEQ ID NO 93
<211> LENGTH: 6
<212> TYPE: PRT
<213> ORGANISM: Homo sapiens

<400> SEQUENCE: 93

Lys Ser Phe Cys Cys Pro
1               5

<210> SEQ ID NO 94
<211> LENGTH: 6
<212> TYPE: PRT
<213> ORGANISM: Homo sapiens

<400> SEQUENCE: 94

Ser Phe Cys Cys Pro Pro
1               5

<210> SEQ ID NO 95
<211> LENGTH: 6
<212> TYPE: PRT
<213> ORGANISM: Homo sapiens

<400> SEQUENCE: 95

Phe Cys Cys Pro Pro Leu
1               5

<210> SEQ ID NO 96
<211> LENGTH: 6
<212> TYPE: PRT
<213> ORGANISM: Homo sapiens

<400> SEQUENCE: 96

Cys Cys Pro Pro Leu Ser
1               5

<210> SEQ ID NO 97
<211> LENGTH: 6
<212> TYPE: PRT
<213> ORGANISM: Homo sapiens

<400> SEQUENCE: 97

Cys Pro Pro Leu Ser Pro
1               5

```
<210> SEQ ID NO 98
<211> LENGTH: 6
<212> TYPE: PRT
<213> ORGANISM: Homo sapiens

<400> SEQUENCE: 98

Pro Pro Leu Ser Pro Ser
1               5

<210> SEQ ID NO 99
<211> LENGTH: 6
<212> TYPE: PRT
<213> ORGANISM: Homo sapiens

<400> SEQUENCE: 99

Pro Leu Ser Pro Ser Lys
1               5

<210> SEQ ID NO 100
<211> LENGTH: 6
<212> TYPE: PRT
<213> ORGANISM: Homo sapiens

<400> SEQUENCE: 100

Leu Ser Pro Ser Lys Leu
1               5

<210> SEQ ID NO 101
<211> LENGTH: 6
<212> TYPE: PRT
<213> ORGANISM: Homo sapiens

<400> SEQUENCE: 101

Ser Pro Ser Lys Leu Gly
1               5

<210> SEQ ID NO 102
<211> LENGTH: 6
<212> TYPE: PRT
<213> ORGANISM: Homo sapiens

<400> SEQUENCE: 102

Pro Ser Lys Leu Gly Pro
1               5

<210> SEQ ID NO 103
<211> LENGTH: 6
<212> TYPE: PRT
<213> ORGANISM: Homo sapiens

<400> SEQUENCE: 103

Ser Lys Leu Gly Pro Phe
1               5

<210> SEQ ID NO 104
<211> LENGTH: 1247
<212> TYPE: DNA
<213> ORGANISM: Homo sapiens

<400> SEQUENCE: 104
cgtgggcttg aggacctgga gagagtagat cctgaagaac ttttcagtc tgctgaagag      60 cttggaagac tggagacaga aggcagagtc tcaggctctg aaggtataag gagtgtgagt    120
tcctgtgaga aacactcatt tgattgtgaa aagacttgaa ttctatgcta agcagggttc    180
```

```
caagtagcta aatgaatgat ctcagcaagt ctctcttgct gctgctgcta ctcgtttaca      240
tttattgatt acttacgatg attcaggtac tgttgtaagt gctttacatg ctgttatacg      300
agactcttgg gagaaatcac tttaatgaag cttgagacac atggcattgc catgcaatga      360 ttttccccc ctcttcacgg gatcagaggg aactaataga atgtgacaat gattctttag       420
cagggactgc tgaggcttct ggttcctttt taagatctgc agtgaaagaa gatgagaaac      480
atggatatgc ccttcttttg gtccccctct tcctttattt gatctctact ccttctata      540 aatatattag ggctacattg tccctttgta tttcaaacaa ggcaaaaga ggttgtaatt       600 acactttact gcaatcctca gtttctccag ggaacaggaa tgcaaaggct ttgaaggcct      660
ctctatttgc tgacatggtc agctgggtgc catgggccaa gtccttctgt tgccctcctc      720
tgtcaccaag taagctaggt cctttctgag gctcaggttt gctgtgatga tgatcacttt      780
taggcagaag gttagaggcc tcatgagtgc tatatggact ttattaggct ttagatttga     840
tggggaataa gggatgtgat tgtcttttg ggaactcatc tttgattcat cattgtctct       900
tggtatcttg gaatttccat gtcattacag tctacagaat gaaagagtaa cctgtcccag      960
aggagaggca ggtgaaagac tccacagcat gctcattctc attctgtctt ctcagtgaca     1020
ccgaggttta ctgagtgccc actatgtgcc aagcactgtg ctcagggctt tctttgtatg     1080
catgatctca gtgaatctca ccaagcctca tctggaaaac ggggacaaat taacaacagg     1140
atggcaaatt gaaaaacacg taaccatgtt ctacagatgg aaaggggtgc ttggttatta     1200
tgaaggcccc ctcgcaagcg tgtgggacat gggtgtgttc tctgggt                   1247

<210> SEQ ID NO 105
<211> LENGTH: 30
<212> TYPE: PRT
<213> ORGANISM: Homo sapiens

<400> SEQUENCE: 105

Arg Ala Thr Leu Ser Leu Cys Ile Ser Asn Lys Ala Lys Arg Gly Cys
1               5                   10                  15

Asn Tyr Thr Leu Leu Gln Ser Ser Val Ser Pro Gly Asn Arg
            20                  25                  30

<210> SEQ ID NO 106
<211> LENGTH: 255
<212> TYPE: DNA
<213> ORGANISM: Homo sapiens

<400> SEQUENCE: 106
atgttccttc cttctcacac acaggactcc cttgtgaaac tcaaggggaa gttcaagttg       60
tccatcttca tctatgaagt agtcacttta tcactgtctt tacagattgc acagtctggg      120
gttttgtggt ttctcttgtc tcactctcca gccaggaaga acttgtcatt tgagttttta      180
aaatgtatca tttcttcccc acctcaaacc acttgtatcc cagtttctca tttaaaggga      240
gaaatggtta tatag                                                       255

<210> SEQ ID NO 107
<211> LENGTH: 123
<212> TYPE: DNA
<213> ORGANISM: Homo sapiens

<400> SEQUENCE: 107
ctcttgtctc actctccagc caggaagaac ttgtcatttg agttttaaa atgtatcatt         60 tcttccccac ctcaaaccac ttgtatccca gtttctcatt taaagggaga aatggttata      120
```

```
-continued tag                                                          123

<210> SEQ ID NO 108
<211> LENGTH: 63
<212> TYPE: DNA
<213> ORGANISM: Homo sapiens

<400> SEQUENCE: 108
atgttccttc cttctcacac acaggactcc cttgtgaaac tcaaggggaa gttcaagttg    60
tcc                                                                 63

<210> SEQ ID NO 109
<211> LENGTH: 255
<212> TYPE: DNA
<213> ORGANISM: Pongo pygmaeus

<400> SEQUENCE: 109
atgttccttc cttctcacac acaggactcc cttgtgaaac tcaaggggaa gttcaagttg    60
tccatcttca tctatgaagt agtcacttta tcactgtctt tacagattgc acagtctggg   120
gttttgtggt ttctcttgtc ttactctcca gccaggaaga acttgtcatt tgagttttta   180
aaatgtatca tttcttcccg acctcaaacc acttgtatcc cagtttctca tttaaaggga   240
gaaatggtta tatag                                                   255

<210> SEQ ID NO 110
<211> LENGTH: 123
<212> TYPE: DNA
<213> ORGANISM: Pongo pygmaeus

<400> SEQUENCE: 110
ctcttgtctt actctccagc caggaagaac ttgtcatttg agttttttaaa atgtatcatt    60 tcttcccgac tcaaaccac ttgtatccca gtttctcatt taaagggaga atggttata    120 tag                                                                123

<210> SEQ ID NO 111
<211> LENGTH: 84
<212> TYPE: PRT
<213> ORGANISM: Homo sapiens

<400> SEQUENCE: 111

Met Phe Leu Pro Ser His Thr Gln Asp Ser Leu Val Lys Leu Lys Gly
1               5                   10                  15

Lys Phe Lys Leu Ser Ile Phe Ile Tyr Glu Val Val Thr Leu Ser Leu
            20                  25                  30

Ser Leu Gln Ile Ala Gln Ser Gly Val Leu Trp Phe Leu Leu Ser His
        35                  40                  45

Ser Pro Ala Arg Lys Asn Leu Ser Phe Glu Phe Leu Lys Cys Ile Ile
    50                  55                  60

Ser Ser Pro Pro Gln Thr Thr Cys Ile Pro Val Ser His Leu Lys Gly
65                  70                  75                  80

Glu Met Val Ile

<210> SEQ ID NO 112
<211> LENGTH: 40
<212> TYPE: PRT
<213> ORGANISM: Homo sapiens

<400> SEQUENCE: 112

Leu Leu Ser His Ser Pro Ala Arg Lys Asn Leu Ser Phe Glu Phe Leu
```

```
                 1               5                  10                  15
Lys Cys Ile Ile Ser Ser Pro Pro Gln Thr Thr Cys Ile Pro Val Ser
                20                  25                  30

His Leu Lys Gly Glu Met Val Ile
        35                  40
```

<210> SEQ ID NO 113
<211> LENGTH: 6
<212> TYPE: PRT
<213> ORGANISM: Homo sapiens

<400> SEQUENCE: 113

```
Leu Leu Ser His Ser Pro
1               5
```

<210> SEQ ID NO 114
<211> LENGTH: 6
<212> TYPE: PRT
<213> ORGANISM: Homo sapiens

<400> SEQUENCE: 114

```
Leu Ser His Ser Pro Ala
1               5
```

<210> SEQ ID NO 115
<211> LENGTH: 6
<212> TYPE: PRT
<213> ORGANISM: Homo sapiens

<400> SEQUENCE: 115

```
Ser His Ser Pro Ala Arg
1               5
```

<210> SEQ ID NO 116
<211> LENGTH: 6
<212> TYPE: PRT
<213> ORGANISM: Homo sapiens

<400> SEQUENCE: 116

```
His Ser Pro Ala Arg Lys
1               5
```

<210> SEQ ID NO 117
<211> LENGTH: 6
<212> TYPE: PRT
<213> ORGANISM: Homo sapiens

<400> SEQUENCE: 117

```
Ser Pro Ala Arg Lys Asn
1               5
```

<210> SEQ ID NO 118
<211> LENGTH: 6
<212> TYPE: PRT
<213> ORGANISM: Homo sapiens

<400> SEQUENCE: 118

```
Pro Ala Arg Lys Asn Leu
1               5
```

<210> SEQ ID NO 119
<211> LENGTH: 6
<212> TYPE: PRT
<213> ORGANISM: Homo sapiens

```
<400> SEQUENCE: 119

Ala Arg Lys Asn Leu Ser
1               5

<210> SEQ ID NO 120
<211> LENGTH: 6
<212> TYPE: PRT
<213> ORGANISM: Homo sapiens

<400> SEQUENCE: 120

Arg Lys Asn Leu Ser Phe
1               5

<210> SEQ ID NO 121
<211> LENGTH: 6
<212> TYPE: PRT
<213> ORGANISM: Homo sapiens

<400> SEQUENCE: 121

Lys Asn Leu Ser Phe Glu
1               5

<210> SEQ ID NO 122
<211> LENGTH: 6
<212> TYPE: PRT
<213> ORGANISM: Homo sapiens

<400> SEQUENCE: 122

Asn Leu Ser Phe Glu Phe
1               5

<210> SEQ ID NO 123
<211> LENGTH: 6
<212> TYPE: PRT
<213> ORGANISM: Homo sapiens

<400> SEQUENCE: 123

Leu Ser Phe Glu Phe Leu
1               5

<210> SEQ ID NO 124
<211> LENGTH: 6
<212> TYPE: PRT
<213> ORGANISM: Homo sapiens

<400> SEQUENCE: 124

Ser Phe Glu Phe Leu Lys
1               5

<210> SEQ ID NO 125
<211> LENGTH: 6
<212> TYPE: PRT
<213> ORGANISM: Homo sapiens

<400> SEQUENCE: 125

Phe Glu Phe Leu Lys Cys
1               5

<210> SEQ ID NO 126
<211> LENGTH: 6
<212> TYPE: PRT
<213> ORGANISM: Homo sapiens

<400> SEQUENCE: 126

Glu Phe Leu Lys Cys Ile
```

```
1               5

<210> SEQ ID NO 127
<211> LENGTH: 6
<212> TYPE: PRT
<213> ORGANISM: Homo sapiens

<400> SEQUENCE: 127

Phe Leu Lys Cys Ile Ile
1               5

<210> SEQ ID NO 128
<211> LENGTH: 6
<212> TYPE: PRT
<213> ORGANISM: Homo sapiens

<400> SEQUENCE: 128

Leu Lys Cys Ile Ile Ser
1               5

<210> SEQ ID NO 129
<211> LENGTH: 6
<212> TYPE: PRT
<213> ORGANISM: Homo sapiens

<400> SEQUENCE: 129

Lys Cys Ile Ile Ser Ser
1               5

<210> SEQ ID NO 130
<211> LENGTH: 6
<212> TYPE: PRT
<213> ORGANISM: Homo sapiens

<400> SEQUENCE: 130

Cys Ile Ile Ser Ser Pro
1               5

<210> SEQ ID NO 131
<211> LENGTH: 6
<212> TYPE: PRT
<213> ORGANISM: Homo sapiens

<400> SEQUENCE: 131

Ile Ile Ser Ser Pro Pro
1               5

<210> SEQ ID NO 132
<211> LENGTH: 6
<212> TYPE: PRT
<213> ORGANISM: Homo sapiens

<400> SEQUENCE: 132

Ile Ser Ser Pro Pro Gln
1               5

<210> SEQ ID NO 133
<211> LENGTH: 6
<212> TYPE: PRT
<213> ORGANISM: Homo sapiens

<400> SEQUENCE: 133

Ser Ser Pro Pro Gln Thr
1               5
```

<210> SEQ ID NO 134
<211> LENGTH: 6
<212> TYPE: PRT
<213> ORGANISM: Homo sapiens

<400> SEQUENCE: 134

Ser Pro Pro Gln Thr Thr
1               5

<210> SEQ ID NO 135
<211> LENGTH: 6
<212> TYPE: PRT
<213> ORGANISM: Homo sapiens

<400> SEQUENCE: 135

Pro Pro Gln Thr Thr Cys
1               5

<210> SEQ ID NO 136
<211> LENGTH: 6
<212> TYPE: PRT
<213> ORGANISM: Homo sapiens

<400> SEQUENCE: 136

Pro Gln Thr Thr Cys Ile
1               5

<210> SEQ ID NO 137
<211> LENGTH: 6
<212> TYPE: PRT
<213> ORGANISM: Homo sapiens

<400> SEQUENCE: 137

Gln Thr Thr Cys Ile Pro
1               5

<210> SEQ ID NO 138
<211> LENGTH: 6
<212> TYPE: PRT
<213> ORGANISM: Homo sapiens

<400> SEQUENCE: 138

Thr Thr Cys Ile Pro Val
1               5

<210> SEQ ID NO 139
<211> LENGTH: 6
<212> TYPE: PRT
<213> ORGANISM: Homo sapiens

<400> SEQUENCE: 139

Thr Cys Ile Pro Val Ser
1               5

<210> SEQ ID NO 140
<211> LENGTH: 6
<212> TYPE: PRT
<213> ORGANISM: Homo sapiens

<400> SEQUENCE: 140

Cys Ile Pro Val Ser His
1               5

<210> SEQ ID NO 141
<211> LENGTH: 6
<212> TYPE: PRT

<213> ORGANISM: Homo sapiens

<400> SEQUENCE: 141

Ile Pro Val Ser His Leu
1               5

<210> SEQ ID NO 142
<211> LENGTH: 6
<212> TYPE: PRT
<213> ORGANISM: Homo sapiens

<400> SEQUENCE: 142

Pro Val Ser His Leu Lys
1               5

<210> SEQ ID NO 143
<211> LENGTH: 6
<212> TYPE: PRT
<213> ORGANISM: Homo sapiens

<400> SEQUENCE: 143

Val Ser His Leu Lys Gly
1               5

<210> SEQ ID NO 144
<211> LENGTH: 6
<212> TYPE: PRT
<213> ORGANISM: Homo sapiens

<400> SEQUENCE: 144

Ser His Leu Lys Gly Glu
1               5

<210> SEQ ID NO 145
<211> LENGTH: 6
<212> TYPE: PRT
<213> ORGANISM: Homo sapiens

<400> SEQUENCE: 145

His Leu Lys Gly Glu Met
1               5

<210> SEQ ID NO 146
<211> LENGTH: 6
<212> TYPE: PRT
<213> ORGANISM: Homo sapiens

<400> SEQUENCE: 146

Leu Lys Gly Glu Met Val
1               5

<210> SEQ ID NO 147
<211> LENGTH: 6
<212> TYPE: PRT
<213> ORGANISM: Homo sapiens

<400> SEQUENCE: 147

Lys Gly Glu Met Val Ile
1               5

<210> SEQ ID NO 148
<211> LENGTH: 21
<212> TYPE: PRT
<213> ORGANISM: Homo sapiens

<400> SEQUENCE: 148

```
Met Phe Leu Pro Ser His Thr Gln Asp Ser Leu Val Lys Leu Lys Gly
 1               5                  10                  15

Lys Phe Lys Leu Ser
            20
```

<210> SEQ ID NO 149
<211> LENGTH: 6
<212> TYPE: PRT
<213> ORGANISM: Homo sapiens

<400> SEQUENCE: 149

```
Met Phe Leu Pro Ser His
 1               5
```

<210> SEQ ID NO 150
<211> LENGTH: 6
<212> TYPE: PRT
<213> ORGANISM: Homo sapiens

<400> SEQUENCE: 150

```
Phe Leu Pro Ser His Thr
 1               5
```

<210> SEQ ID NO 151
<211> LENGTH: 6
<212> TYPE: PRT
<213> ORGANISM: Homo sapiens

<400> SEQUENCE: 151

```
Leu Pro Ser His Thr Gln
 1               5
```

<210> SEQ ID NO 152
<211> LENGTH: 6
<212> TYPE: PRT
<213> ORGANISM: Homo sapiens

<400> SEQUENCE: 152

```
Pro Ser His Thr Gln Asp
 1               5
```

<210> SEQ ID NO 153
<211> LENGTH: 6
<212> TYPE: PRT
<213> ORGANISM: Homo sapiens

<400> SEQUENCE: 153

```
Ser His Thr Gln Asp Ser
 1               5
```

<210> SEQ ID NO 154
<211> LENGTH: 6
<212> TYPE: PRT
<213> ORGANISM: Homo sapiens

<400> SEQUENCE: 154

```
His Thr Gln Asp Ser Leu
 1               5
```

<210> SEQ ID NO 155
<211> LENGTH: 6
<212> TYPE: PRT
<213> ORGANISM: Homo sapiens

<400> SEQUENCE: 155

Thr Gln Asp Ser Leu Val
1               5

<210> SEQ ID NO 156
<211> LENGTH: 6
<212> TYPE: PRT
<213> ORGANISM: Homo sapiens

<400> SEQUENCE: 156

Gln Asp Ser Leu Val Lys
1               5

<210> SEQ ID NO 157
<211> LENGTH: 6
<212> TYPE: PRT
<213> ORGANISM: Homo sapiens

<400> SEQUENCE: 157

Asp Ser Leu Val Lys Leu
1               5

<210> SEQ ID NO 158
<211> LENGTH: 6
<212> TYPE: PRT
<213> ORGANISM: Homo sapiens

<400> SEQUENCE: 158

Ser Leu Val Lys Leu Lys
1               5

<210> SEQ ID NO 159
<211> LENGTH: 6
<212> TYPE: PRT
<213> ORGANISM: Homo sapiens

<400> SEQUENCE: 159

Leu Val Lys Leu Lys Gly
1               5

<210> SEQ ID NO 160
<211> LENGTH: 6
<212> TYPE: PRT
<213> ORGANISM: Homo sapiens

<400> SEQUENCE: 160

Val Lys Leu Lys Gly Lys
1               5

<210> SEQ ID NO 161
<211> LENGTH: 6
<212> TYPE: PRT
<213> ORGANISM: Homo sapiens

<400> SEQUENCE: 161

Lys Leu Lys Gly Lys Phe
1               5

<210> SEQ ID NO 162
<211> LENGTH: 6
<212> TYPE: PRT
<213> ORGANISM: Homo sapiens

<400> SEQUENCE: 162

Leu Lys Gly Lys Phe Lys
1               5

<210> SEQ ID NO 163
<211> LENGTH: 6
<212> TYPE: PRT
<213> ORGANISM: Homo sapiens

<400> SEQUENCE: 163

Lys Gly Lys Phe Lys Leu
1               5

<210> SEQ ID NO 164
<211> LENGTH: 6
<212> TYPE: PRT
<213> ORGANISM: Homo sapiens

<400> SEQUENCE: 164

Gly Lys Phe Lys Leu Ser
1               5

<210> SEQ ID NO 165
<211> LENGTH: 84
<212> TYPE: PRT
<213> ORGANISM: Pongo pygmaeus

<400> SEQUENCE: 165

Met Phe Leu Pro Ser His Thr Gln Asp Ser Leu Val Lys Leu Lys Gly
1               5                   10                  15

Lys Phe Lys Leu Ser Ile Phe Ile Tyr Glu Val Val Thr Leu Ser Leu
                20                  25                  30

Ser Leu Gln Ile Ala Gln Ser Gly Val Leu Trp Phe Leu Leu Ser Tyr
        35                  40                  45

Ser Pro Ala Arg Lys Asn Leu Ser Phe Glu Phe Leu Cys Ile Ile
    50                  55                  60

Ser Ser Arg Pro Gln Thr Thr Cys Ile Pro Val Ser His Leu Lys Gly
65                  70                  75                  80

Glu Met Val Ile

<210> SEQ ID NO 166
<211> LENGTH: 40
<212> TYPE: PRT
<213> ORGANISM: Pongo pygmaeus

<400> SEQUENCE: 166

Leu Leu Ser Tyr Ser Pro Ala Arg Lys Asn Leu Ser Phe Glu Phe Leu
1               5                   10                  15

Lys Cys Ile Ile Ser Ser Arg Pro Gln Thr Thr Cys Ile Pro Val Ser
                20                  25                  30

His Leu Lys Gly Glu Met Val Ile
        35                  40

<210> SEQ ID NO 167
<211> LENGTH: 6
<212> TYPE: PRT
<213> ORGANISM: Pongo pygmaeus

<400> SEQUENCE: 167

Leu Leu Ser Tyr Ser Pro
1               5

<210> SEQ ID NO 168
<211> LENGTH: 6
<212> TYPE: PRT

-continued

<213> ORGANISM: Pongo pygmaeus

<400> SEQUENCE: 168

Leu Ser Tyr Ser Pro Ala
1               5

<210> SEQ ID NO 169
<211> LENGTH: 6
<212> TYPE: PRT
<213> ORGANISM: Pongo pygmaeus

<400> SEQUENCE: 169

Ser Tyr Ser Pro Ala Arg
1               5

<210> SEQ ID NO 170
<211> LENGTH: 6
<212> TYPE: PRT
<213> ORGANISM: Pongo pygmaeus

<400> SEQUENCE: 170

Tyr Ser Pro Ala Arg Lys
1               5

<210> SEQ ID NO 171
<211> LENGTH: 6
<212> TYPE: PRT
<213> ORGANISM: Pongo pygmaeus

<400> SEQUENCE: 171

Cys Ile Ile Ser Ser Arg
1               5

<210> SEQ ID NO 172
<211> LENGTH: 6
<212> TYPE: PRT
<213> ORGANISM: Pongo pygmaeus

<400> SEQUENCE: 172

Ile Ile Ser Ser Arg Pro
1               5

<210> SEQ ID NO 173
<211> LENGTH: 6
<212> TYPE: PRT
<213> ORGANISM: Pongo pygmaeus

<400> SEQUENCE: 173

Ile Ser Ser Arg Pro Gln
1               5

<210> SEQ ID NO 174
<211> LENGTH: 6
<212> TYPE: PRT
<213> ORGANISM: Pongo pygmaeus

<400> SEQUENCE: 174

Ser Ser Arg Pro Gln Thr
1               5

<210> SEQ ID NO 175
<211> LENGTH: 6
<212> TYPE: PRT
<213> ORGANISM: Pongo pygmaeus

<400> SEQUENCE: 175

Ser Arg Pro Gln Thr Thr
1               5

<210> SEQ ID NO 176
<211> LENGTH: 6
<212> TYPE: PRT
<213> ORGANISM: Pongo pygmaeus

<400> SEQUENCE: 176

Arg Pro Gln Thr Thr Cys
1               5

<210> SEQ ID NO 177
<211> LENGTH: 955
<212> TYPE: DNA
<213> ORGANISM: Homo sapiens

<400> SEQUENCE: 177

| | | | | | |
|---|---|---|---|---|---|
| ggggaaagaa | ccagggctga | gctgtggagt | gaaggggagc | catttctctc | caccgactgc | 60 |
| aacctccgtg | ctcacagctc | acggttcacc | agaatccagg | ggcttggtcg | gcctaggaat | 120 |
| ccacaatgct | ggatattttc | atcctgatgt | tctttgccat | cataggcctg | gtcattctgt | 180 |
| cctacattat | ctatctgctc | tagtggcctg | gagctgcggc | cggagcctgc | tggagaacag | 240 |
| ctcagaagga | aggatggagc | tgaatggccg | agtgccctgc | ttgctgacgc | accggtggat | 300 |
| ttttgcttct | gctgttatct | cggctcctgg | tctctccagt | ccaacaagag | gcctctcatc | 360 |
| cacagaagca | gtcctactgc | ccagcagacc | tctttcagag | ccttccagac | atggctgacc | 420 |
| cctggcaagc | aagggggcttt | ttgagctgag | aggcacttgg | ctgggacttc | aggaattcat | 480 |
| ggacagggct | ggcagatact | gcatatgttt | gagctgtaga | tgggattgag | aacagaaagt | 540 |
| tgaaatggag | acttattaaa | gttaccgtgg | agaactgctc | aaaaattcat | tttgaattaa | 600 |
| ggaaacttaa | attcatttta | gtttccctta | gatctaaatg | caactgcaca | ttacactcaa | 660 |
| atatgttcct | tccttctcac | acacaggact | cccttgtgaa | actcaagggg | aagttcaagt | 720 |
| tgtccatctt | catctatgaa | gtagtcactt | tatcactgtc | tttacagatt | gcacagtctg | 780 |
| gggttttgtg | gtttctcttg | tctcactctc | cagccaggaa | gaacttgtca | tttgagtttt | 840 |
| taaaatgtat | catttcttcc | ccacctcaaa | ccacttgtat | cccagtttct | catttaaagg | 900 |
| gagaaatggt | tatatagtcc | tctctttgca | cctgattgaa | ttataaatga | tagaa | 955 |

<210> SEQ ID NO 178
<211> LENGTH: 1151
<212> TYPE: DNA
<213> ORGANISM: Pongo pygmaeus

<400> SEQUENCE: 178

| | | | | | |
|---|---|---|---|---|---|
| tcctggtact | ttgcagttgt | ccccatctga | gacttttat | ttctgggttt | cttacagctc | 60 |
| ctggtctctc | cagtccaaca | agaggcctct | catccacaga | agcagtcctg | ctgcccagca | 120 |
| gacctctttc | agagccttcc | agacatggct | gaccccctggc | aagcaagggg | cttttgagc | 180 |
| tgagaggcac | ttggctggga | catcaggaat | tcatggacag | ggctggcaga | tactgcatat | 240 |
| gtttgagctg | tagatgggat | tgagaacaga | aagttgaaat | ggagacttat | taaagttacc | 300 |
| gtggagaact | gctcaaaaat | tcattttgaa | ttaaggaaac | ttaaattcat | tttaagtttc | 360 |
| cttagatcta | aatgcaactg | cacattacac | tcaaatatgt | tccttccttc | tcacacacag | 420 |
| gactcccttg | tgaaactcaa | ggggaagttc | aagttgtcca | tcttcatcta | tgaagtagtc | 480 |
| actttatcac | tgtctttaca | gattgcacag | tctgggggttt | tgtggtttct | cttgtcttac | 540 |

| | | |
|---|---|---|
| tctccagcca ggaagaactt gtcatttgag tttttaaaat gtatcatttc ttcccgacct | 600 | |
| caaaccactt gtatcccagt ttctcattta aagggagaaa tggttatata gtcctctctt | 660 | |
| tgcacctgat tgaattataa atgatagaaa caagatggct atacttattt aggaaaaatc | 720 | |
| tcttacccca aaatgagtgt gtgtgtgtgt gtgtgtgtgt gtgtttgtgt gtgtgtgtgt | 780 | |
| tttctggaaa aaactttcca catagttctc tgacccatta gagttgaaga aactatatat | 840 | |
| tttgggattc agagtagaat tggcctgcaa atctgggatg tttattcctt ttacaagtct | 900 | |
| ataataattg ttctacattt aattttcctt tcttgcttaa aagtaaacaa ggagagtcag | 960 | |
| gagtggtggc tcatgcctgt aatcccagca ctctgggagg ccgaggcgga tggatcacct | 1020 | |
| gaggtcagga gttggagacc agcctggcca acacggtgaa accccatctc tactaaaaat | 1080 | |
| acaaaaatta gtcaggcaca gtagtgcgcg cctgtagtcc cagctacccg ggaggctgag | 1140 | |
| gccgaagaat t | 1151 | |

<210> SEQ ID NO 179
<211> LENGTH: 339
<212> TYPE: DNA
<213> ORGANISM: Homo sapiens

<400> SEQUENCE: 179

| | | |
|---|---|---|
| atggtaatca ccaaggaggt gacacctaag gtaatctgcg ccagtagctg ggcagtttat | 60 | |
| catagcttat gtatgcaagg ggcctgcgta cccagaagct tatgtatgta tcgggcttgt | 120 | |
| gtgcccaagg cttgtgtgtc aggcttatgt gtcaagcctg tgtatgtatt gggcctgcat | 180 | |
| gcccaaagtt tatatgtcag gcctgtatgc caaacctgtg gatcaaacct gtgtgtccaa | 240 | |
| ggcatatgtc tcgtttggcc taggggtgg agtgtaaggt acatatggat gtgctttggt | 300 | |
| caaggaacag gccgaggtgg atatccaagg cctgcgtaa | 339 | |

<210> SEQ ID NO 180
<211> LENGTH: 39
<212> TYPE: DNA
<213> ORGANISM: Homo sapiens

<400> SEQUENCE: 180

| | | |
|---|---|---|
| ggtcaaggaa caggccgagg tggatatcca aggcctgcg | 39 | |

<210> SEQ ID NO 181
<211> LENGTH: 306
<212> TYPE: DNA
<213> ORGANISM: Homo sapiens

<400> SEQUENCE: 181

| | | |
|---|---|---|
| atgtgtctca catacctgaa gacattctgg gggtggatgt tttgcacggc ttggcagctg | 60 | |
| tattgtctgt cacggacttg ccgaccgctt gacaacggaa ctgggacttc ttgtccagag | 120 | |
| agccaggaac agtttgcctt catgggaggg caacaatgga cttttttcttt tttcttttc | 180 | |
| tttttttttt tttttttga gatggagtct tgctctgtcg cccaggctgg agtgcagggc | 240 | |
| acgatctcag ctccctgcga cctccgccac ctgggttcaa gcaattctcc tgcctcagcc | 300 | |
| tcctga | 306 | |

<210> SEQ ID NO 182
<211> LENGTH: 132
<212> TYPE: DNA
<213> ORGANISM: Homo sapiens

<400> SEQUENCE: 182

```
atgtgtctca catacctgaa gacattctgg gggtggatgt tttgcacggc ttggcagctg    60
tattgtctgt cacggacttg ccgaccgctt gacaacggaa ctgggacttc ttgtccagag   120
agccaggaac ag                                                       132
```

<210> SEQ ID NO 183
<211> LENGTH: 105
<212> TYPE: DNA
<213> ORGANISM: Homo sapiens

<400> SEQUENCE: 183

```
gagatggagt cttgctctgt cgcccaggct ggagtgcagg gcacgatctc agctccctgc    60
gacctccgcc acctgggttc aagcaattct cctgcctcag cctcc                  105
```

<210> SEQ ID NO 184
<211> LENGTH: 63
<212> TYPE: DNA
<213> ORGANISM: Homo sapiens

<400> SEQUENCE: 184

```
cggacttgcc gaccgcttga caacggaact gggacttctt gtccagagag ccaggaacag    60
ttt                                                                  63
```

<210> SEQ ID NO 185
<211> LENGTH: 112
<212> TYPE: PRT
<213> ORGANISM: Homo sapiens

<400> SEQUENCE: 185

Met Val Ile Thr Lys Glu Val Thr Pro Lys Val Ile Cys Ala Ser Ser
1               5                   10                  15

Trp Ala Val Tyr His Ser Leu Cys Met Gln Gly Ala Cys Val Pro Arg
            20                  25                  30

Ser Leu Cys Met Tyr Arg Ala Cys Val Pro Lys Ala Cys Val Ser Gly
        35                  40                  45

Leu Cys Val Lys Pro Val Tyr Val Leu Gly Leu His Ala Gln Ser Leu
    50                  55                  60

Tyr Val Arg Pro Val Cys Gln Thr Cys Gly Ser Asn Leu Cys Val Gln
65                  70                  75                  80

Gly Ile Cys Leu Val Trp Pro Arg Gly Trp Ser Val Arg Tyr Ile Trp
                85                  90                  95

Met Cys Phe Gly Gln Gly Thr Gly Arg Gly Gly Tyr Pro Arg Pro Ala
            100                 105                 110

<210> SEQ ID NO 186
<211> LENGTH: 6
<212> TYPE: PRT
<213> ORGANISM: Homo sapiens

<400> SEQUENCE: 186

Met Val Ile Thr Lys Glu
1               5

<210> SEQ ID NO 187
<211> LENGTH: 6
<212> TYPE: PRT
<213> ORGANISM: Homo sapiens

<400> SEQUENCE: 187

Val Ile Thr Lys Glu Val

```
<210> SEQ ID NO 188
<211> LENGTH: 6
<212> TYPE: PRT
<213> ORGANISM: Homo sapiens

<400> SEQUENCE: 188

Ile Thr Lys Glu Val Thr
1               5

<210> SEQ ID NO 189
<211> LENGTH: 6
<212> TYPE: PRT
<213> ORGANISM: Homo sapiens

<400> SEQUENCE: 189

Thr Lys Glu Val Thr Pro
1               5

<210> SEQ ID NO 190
<211> LENGTH: 6
<212> TYPE: PRT
<213> ORGANISM: Homo sapiens

<400> SEQUENCE: 190

Lys Glu Val Thr Pro Lys
1               5

<210> SEQ ID NO 191
<211> LENGTH: 6
<212> TYPE: PRT
<213> ORGANISM: Homo sapiens

<400> SEQUENCE: 191

Glu Val Thr Pro Lys Val
1               5

<210> SEQ ID NO 192
<211> LENGTH: 6
<212> TYPE: PRT
<213> ORGANISM: Homo sapiens

<400> SEQUENCE: 192

Val Thr Pro Lys Val Ile
1               5

<210> SEQ ID NO 193
<211> LENGTH: 6
<212> TYPE: PRT
<213> ORGANISM: Homo sapiens

<400> SEQUENCE: 193

Thr Pro Lys Val Ile Cys
1               5

<210> SEQ ID NO 194
<211> LENGTH: 6
<212> TYPE: PRT
<213> ORGANISM: Homo sapiens

<400> SEQUENCE: 194

Pro Lys Val Ile Cys Ala
1               5
```

```
<210> SEQ ID NO 195
<211> LENGTH: 6
<212> TYPE: PRT
<213> ORGANISM: Homo sapiens

<400> SEQUENCE: 195

Lys Val Ile Cys Ala Ser
1               5

<210> SEQ ID NO 196
<211> LENGTH: 6
<212> TYPE: PRT
<213> ORGANISM: Homo sapiens

<400> SEQUENCE: 196

Val Ile Cys Ala Ser Ser
1               5

<210> SEQ ID NO 197
<211> LENGTH: 6
<212> TYPE: PRT
<213> ORGANISM: Homo sapiens

<400> SEQUENCE: 197

Ile Cys Ala Ser Ser Trp
1               5

<210> SEQ ID NO 198
<211> LENGTH: 6
<212> TYPE: PRT
<213> ORGANISM: Homo sapiens

<400> SEQUENCE: 198

Cys Ala Ser Ser Trp Ala
1               5

<210> SEQ ID NO 199
<211> LENGTH: 6
<212> TYPE: PRT
<213> ORGANISM: Homo sapiens

<400> SEQUENCE: 199

Ala Ser Ser Trp Ala Val
1               5

<210> SEQ ID NO 200
<211> LENGTH: 6
<212> TYPE: PRT
<213> ORGANISM: Homo sapiens

<400> SEQUENCE: 200

Ser Ser Trp Ala Val Tyr
1               5

<210> SEQ ID NO 201
<211> LENGTH: 6
<212> TYPE: PRT
<213> ORGANISM: Homo sapiens

<400> SEQUENCE: 201

Ser Trp Ala Val Tyr His
1               5

<210> SEQ ID NO 202
<211> LENGTH: 6
<212> TYPE: PRT
```

<213> ORGANISM: Homo sapiens

<400> SEQUENCE: 202

Trp Ala Val Tyr His Ser
1               5

<210> SEQ ID NO 203
<211> LENGTH: 6
<212> TYPE: PRT
<213> ORGANISM: Homo sapiens

<400> SEQUENCE: 203

Ala Val Tyr His Ser Leu
1               5

<210> SEQ ID NO 204
<211> LENGTH: 6
<212> TYPE: PRT
<213> ORGANISM: Homo sapiens

<400> SEQUENCE: 204

Val Tyr His Ser Leu Cys
1               5

<210> SEQ ID NO 205
<211> LENGTH: 6
<212> TYPE: PRT
<213> ORGANISM: Homo sapiens

<400> SEQUENCE: 205

Tyr His Ser Leu Cys Met
1               5

<210> SEQ ID NO 206
<211> LENGTH: 6
<212> TYPE: PRT
<213> ORGANISM: Homo sapiens

<400> SEQUENCE: 206

His Ser Leu Cys Met Gln
1               5

<210> SEQ ID NO 207
<211> LENGTH: 6
<212> TYPE: PRT
<213> ORGANISM: Homo sapiens

<400> SEQUENCE: 207

Ser Leu Cys Met Gln Gly
1               5

<210> SEQ ID NO 208
<211> LENGTH: 6
<212> TYPE: PRT
<213> ORGANISM: Homo sapiens

<400> SEQUENCE: 208

Leu Cys Met Gln Gly Ala
1               5

<210> SEQ ID NO 209
<211> LENGTH: 6
<212> TYPE: PRT
<213> ORGANISM: Homo sapiens

<400> SEQUENCE: 209

```
Cys Met Gln Gly Ala Cys
1               5

<210> SEQ ID NO 210
<211> LENGTH: 6
<212> TYPE: PRT
<213> ORGANISM: Homo sapiens

<400> SEQUENCE: 210

Met Gln Gly Ala Cys Val
1               5

<210> SEQ ID NO 211
<211> LENGTH: 6
<212> TYPE: PRT
<213> ORGANISM: Homo sapiens

<400> SEQUENCE: 211

Gln Gly Ala Cys Val Pro
1               5

<210> SEQ ID NO 212
<211> LENGTH: 6
<212> TYPE: PRT
<213> ORGANISM: Homo sapiens

<400> SEQUENCE: 212

Gly Ala Cys Val Pro Arg
1               5

<210> SEQ ID NO 213
<211> LENGTH: 6
<212> TYPE: PRT
<213> ORGANISM: Homo sapiens

<400> SEQUENCE: 213

Ala Cys Val Pro Arg Ser
1               5

<210> SEQ ID NO 214
<211> LENGTH: 6
<212> TYPE: PRT
<213> ORGANISM: Homo sapiens

<400> SEQUENCE: 214

Cys Val Pro Arg Ser Leu
1               5

<210> SEQ ID NO 215
<211> LENGTH: 6
<212> TYPE: PRT
<213> ORGANISM: Homo sapiens

<400> SEQUENCE: 215

Val Pro Arg Ser Leu Cys
1               5

<210> SEQ ID NO 216
<211> LENGTH: 6
<212> TYPE: PRT
<213> ORGANISM: Homo sapiens

<400> SEQUENCE: 216

Pro Arg Ser Leu Cys Met
1               5
```

```
<210> SEQ ID NO 217
<211> LENGTH: 6
<212> TYPE: PRT
<213> ORGANISM: Homo sapiens

<400> SEQUENCE: 217

Arg Ser Leu Cys Met Tyr
1               5

<210> SEQ ID NO 218
<211> LENGTH: 6
<212> TYPE: PRT
<213> ORGANISM: Homo sapiens

<400> SEQUENCE: 218

Ser Leu Cys Met Tyr Arg
1               5

<210> SEQ ID NO 219
<211> LENGTH: 6
<212> TYPE: PRT
<213> ORGANISM: Homo sapiens

<400> SEQUENCE: 219

Leu Cys Met Tyr Arg Ala
1               5

<210> SEQ ID NO 220
<211> LENGTH: 6
<212> TYPE: PRT
<213> ORGANISM: Homo sapiens

<400> SEQUENCE: 220

Cys Met Tyr Arg Ala Cys
1               5

<210> SEQ ID NO 221
<211> LENGTH: 6
<212> TYPE: PRT
<213> ORGANISM: Homo sapiens

<400> SEQUENCE: 221

Met Tyr Arg Ala Cys Val
1               5

<210> SEQ ID NO 222
<211> LENGTH: 6
<212> TYPE: PRT
<213> ORGANISM: Homo sapiens

<400> SEQUENCE: 222

Tyr Arg Ala Cys Val Pro
1               5

<210> SEQ ID NO 223
<211> LENGTH: 6
<212> TYPE: PRT
<213> ORGANISM: Homo sapiens

<400> SEQUENCE: 223

Arg Ala Cys Val Pro Lys
1               5

<210> SEQ ID NO 224
```

```
<211> LENGTH: 6
<212> TYPE: PRT
<213> ORGANISM: Homo sapiens

<400> SEQUENCE: 224

Ala Cys Val Pro Lys Ala
1               5

<210> SEQ ID NO 225
<211> LENGTH: 6
<212> TYPE: PRT
<213> ORGANISM: Homo sapiens

<400> SEQUENCE: 225

Cys Val Pro Lys Ala Cys
1               5

<210> SEQ ID NO 226
<211> LENGTH: 6
<212> TYPE: PRT
<213> ORGANISM: Homo sapiens

<400> SEQUENCE: 226

Val Pro Lys Ala Cys Val
1               5

<210> SEQ ID NO 227
<211> LENGTH: 6
<212> TYPE: PRT
<213> ORGANISM: Homo sapiens

<400> SEQUENCE: 227

Pro Lys Ala Cys Val Ser
1               5

<210> SEQ ID NO 228
<211> LENGTH: 6
<212> TYPE: PRT
<213> ORGANISM: Homo sapiens

<400> SEQUENCE: 228

Lys Ala Cys Val Ser Gly
1               5

<210> SEQ ID NO 229
<211> LENGTH: 6
<212> TYPE: PRT
<213> ORGANISM: Homo sapiens

<400> SEQUENCE: 229

Ala Cys Val Ser Gly Leu
1               5

<210> SEQ ID NO 230
<211> LENGTH: 6
<212> TYPE: PRT
<213> ORGANISM: Homo sapiens

<400> SEQUENCE: 230

Cys Val Ser Gly Leu Cys
1               5

<210> SEQ ID NO 231
<211> LENGTH: 6
<212> TYPE: PRT
<213> ORGANISM: Homo sapiens
```

<400> SEQUENCE: 231

Val Ser Gly Leu Cys Val
1               5

<210> SEQ ID NO 232
<211> LENGTH: 6
<212> TYPE: PRT
<213> ORGANISM: Homo sapiens

<400> SEQUENCE: 232

Ser Gly Leu Cys Val Lys
1               5

<210> SEQ ID NO 233
<211> LENGTH: 6
<212> TYPE: PRT
<213> ORGANISM: Homo sapiens

<400> SEQUENCE: 233

Gly Leu Cys Val Lys Pro
1               5

<210> SEQ ID NO 234
<211> LENGTH: 6
<212> TYPE: PRT
<213> ORGANISM: Homo sapiens

<400> SEQUENCE: 234

Leu Cys Val Lys Pro Val
1               5

<210> SEQ ID NO 235
<211> LENGTH: 6
<212> TYPE: PRT
<213> ORGANISM: Homo sapiens

<400> SEQUENCE: 235

Cys Val Lys Pro Val Tyr
1               5

<210> SEQ ID NO 236
<211> LENGTH: 6
<212> TYPE: PRT
<213> ORGANISM: Homo sapiens

<400> SEQUENCE: 236

Val Lys Pro Val Tyr Val
1               5

<210> SEQ ID NO 237
<211> LENGTH: 6
<212> TYPE: PRT
<213> ORGANISM: Homo sapiens

<400> SEQUENCE: 237

Lys Pro Val Tyr Val Leu
1               5

<210> SEQ ID NO 238
<211> LENGTH: 6
<212> TYPE: PRT
<213> ORGANISM: Homo sapiens

<400> SEQUENCE: 238

Pro Val Tyr Val Leu Gly
1               5

<210> SEQ ID NO 239
<211> LENGTH: 6
<212> TYPE: PRT
<213> ORGANISM: Homo sapiens

<400> SEQUENCE: 239

Val Tyr Val Leu Gly Leu
1               5

<210> SEQ ID NO 240
<211> LENGTH: 6
<212> TYPE: PRT
<213> ORGANISM: Homo sapiens

<400> SEQUENCE: 240

Tyr Val Leu Gly Leu His
1               5

<210> SEQ ID NO 241
<211> LENGTH: 6
<212> TYPE: PRT
<213> ORGANISM: Homo sapiens

<400> SEQUENCE: 241

Val Leu Gly Leu His Ala
1               5

<210> SEQ ID NO 242
<211> LENGTH: 6
<212> TYPE: PRT
<213> ORGANISM: Homo sapiens

<400> SEQUENCE: 242

Leu Gly Leu His Ala Gln
1               5

<210> SEQ ID NO 243
<211> LENGTH: 6
<212> TYPE: PRT
<213> ORGANISM: Homo sapiens

<400> SEQUENCE: 243

Gly Leu His Ala Gln Ser
1               5

<210> SEQ ID NO 244
<211> LENGTH: 6
<212> TYPE: PRT
<213> ORGANISM: Homo sapiens

<400> SEQUENCE: 244

Leu His Ala Gln Ser Leu
1               5

<210> SEQ ID NO 245
<211> LENGTH: 6
<212> TYPE: PRT
<213> ORGANISM: Homo sapiens

<400> SEQUENCE: 245

His Ala Gln Ser Leu Tyr
1               5

```
<210> SEQ ID NO 246
<211> LENGTH: 6
<212> TYPE: PRT
<213> ORGANISM: Homo sapiens

<400> SEQUENCE: 246

Ala Gln Ser Leu Tyr Val
1               5

<210> SEQ ID NO 247
<211> LENGTH: 6
<212> TYPE: PRT
<213> ORGANISM: Homo sapiens

<400> SEQUENCE: 247

Gln Ser Leu Tyr Val Arg
1               5

<210> SEQ ID NO 248
<211> LENGTH: 6
<212> TYPE: PRT
<213> ORGANISM: Homo sapiens

<400> SEQUENCE: 248

Ser Leu Tyr Val Arg Pro
1               5

<210> SEQ ID NO 249
<211> LENGTH: 6
<212> TYPE: PRT
<213> ORGANISM: Homo sapiens

<400> SEQUENCE: 249

Leu Tyr Val Arg Pro Val
1               5

<210> SEQ ID NO 250
<211> LENGTH: 6
<212> TYPE: PRT
<213> ORGANISM: Homo sapiens

<400> SEQUENCE: 250

Tyr Val Arg Pro Val Cys
1               5

<210> SEQ ID NO 251
<211> LENGTH: 6
<212> TYPE: PRT
<213> ORGANISM: Homo sapiens

<400> SEQUENCE: 251

Val Arg Pro Val Cys Gln
1               5

<210> SEQ ID NO 252
<211> LENGTH: 6
<212> TYPE: PRT
<213> ORGANISM: Homo sapiens

<400> SEQUENCE: 252

Arg Pro Val Cys Gln Thr
1               5

<210> SEQ ID NO 253
<211> LENGTH: 6
```

```
<212> TYPE: PRT
<213> ORGANISM: Homo sapiens

<400> SEQUENCE: 253

Pro Val Cys Gln Thr Cys
1               5

<210> SEQ ID NO 254
<211> LENGTH: 6
<212> TYPE: PRT
<213> ORGANISM: Homo sapiens

<400> SEQUENCE: 254

Val Cys Gln Thr Cys Gly
1               5

<210> SEQ ID NO 255
<211> LENGTH: 6
<212> TYPE: PRT
<213> ORGANISM: Homo sapiens

<400> SEQUENCE: 255

Cys Gln Thr Cys Gly Ser
1               5

<210> SEQ ID NO 256
<211> LENGTH: 6
<212> TYPE: PRT
<213> ORGANISM: Homo sapiens

<400> SEQUENCE: 256

Gln Thr Cys Gly Ser Asn
1               5

<210> SEQ ID NO 257
<211> LENGTH: 6
<212> TYPE: PRT
<213> ORGANISM: Homo sapiens

<400> SEQUENCE: 257

Thr Cys Gly Ser Asn Leu
1               5

<210> SEQ ID NO 258
<211> LENGTH: 6
<212> TYPE: PRT
<213> ORGANISM: Homo sapiens

<400> SEQUENCE: 258

Cys Gly Ser Asn Leu Cys
1               5

<210> SEQ ID NO 259
<211> LENGTH: 6
<212> TYPE: PRT
<213> ORGANISM: Homo sapiens

<400> SEQUENCE: 259

Gly Ser Asn Leu Cys Val
1               5

<210> SEQ ID NO 260
<211> LENGTH: 6
<212> TYPE: PRT
<213> ORGANISM: Homo sapiens
```

```
<400> SEQUENCE: 260

Ser Asn Leu Cys Val Gln
1               5

<210> SEQ ID NO 261
<211> LENGTH: 6
<212> TYPE: PRT
<213> ORGANISM: Homo sapiens

<400> SEQUENCE: 261

Asn Leu Cys Val Gln Gly
1               5

<210> SEQ ID NO 262
<211> LENGTH: 6
<212> TYPE: PRT
<213> ORGANISM: Homo sapiens

<400> SEQUENCE: 262

Leu Cys Val Gln Gly Ile
1               5

<210> SEQ ID NO 263
<211> LENGTH: 6
<212> TYPE: PRT
<213> ORGANISM: Homo sapiens

<400> SEQUENCE: 263

Cys Val Gln Gly Ile Cys
1               5

<210> SEQ ID NO 264
<211> LENGTH: 6
<212> TYPE: PRT
<213> ORGANISM: Homo sapiens

<400> SEQUENCE: 264

Val Gln Gly Ile Cys Leu
1               5

<210> SEQ ID NO 265
<211> LENGTH: 6
<212> TYPE: PRT
<213> ORGANISM: Homo sapiens

<400> SEQUENCE: 265

Gln Gly Ile Cys Leu Val
1               5

<210> SEQ ID NO 266
<211> LENGTH: 6
<212> TYPE: PRT
<213> ORGANISM: Homo sapiens

<400> SEQUENCE: 266

Gly Ile Cys Leu Val Trp
1               5

<210> SEQ ID NO 267
<211> LENGTH: 6
<212> TYPE: PRT
<213> ORGANISM: Homo sapiens

<400> SEQUENCE: 267

Ile Cys Leu Val Trp Pro
```

```
                               1               5

<210> SEQ ID NO 268
<211> LENGTH: 6
<212> TYPE: PRT
<213> ORGANISM: Homo sapiens

<400> SEQUENCE: 268

Cys Leu Val Trp Pro Arg
1               5

<210> SEQ ID NO 269
<211> LENGTH: 6
<212> TYPE: PRT
<213> ORGANISM: Homo sapiens

<400> SEQUENCE: 269

Leu Val Trp Pro Arg Gly
1               5

<210> SEQ ID NO 270
<211> LENGTH: 6
<212> TYPE: PRT
<213> ORGANISM: Homo sapiens

<400> SEQUENCE: 270

Val Trp Pro Arg Gly Trp
1               5

<210> SEQ ID NO 271
<211> LENGTH: 6
<212> TYPE: PRT
<213> ORGANISM: Homo sapiens

<400> SEQUENCE: 271

Trp Pro Arg Gly Trp Ser
1               5

<210> SEQ ID NO 272
<211> LENGTH: 6
<212> TYPE: PRT
<213> ORGANISM: Homo sapiens

<400> SEQUENCE: 272

Pro Arg Gly Trp Ser Val
1               5

<210> SEQ ID NO 273
<211> LENGTH: 6
<212> TYPE: PRT
<213> ORGANISM: Homo sapiens

<400> SEQUENCE: 273

Arg Gly Trp Ser Val Arg
1               5

<210> SEQ ID NO 274
<211> LENGTH: 6
<212> TYPE: PRT
<213> ORGANISM: Homo sapiens

<400> SEQUENCE: 274

Gly Trp Ser Val Arg Tyr
1               5
```

```
<210> SEQ ID NO 275
<211> LENGTH: 6
<212> TYPE: PRT
<213> ORGANISM: Homo sapiens

<400> SEQUENCE: 275

Trp Ser Val Arg Tyr Ile
1               5

<210> SEQ ID NO 276
<211> LENGTH: 6
<212> TYPE: PRT
<213> ORGANISM: Homo sapiens

<400> SEQUENCE: 276

Ser Val Arg Tyr Ile Trp
1               5

<210> SEQ ID NO 277
<211> LENGTH: 6
<212> TYPE: PRT
<213> ORGANISM: Homo sapiens

<400> SEQUENCE: 277

Val Arg Tyr Ile Trp Met
1               5

<210> SEQ ID NO 278
<211> LENGTH: 6
<212> TYPE: PRT
<213> ORGANISM: Homo sapiens

<400> SEQUENCE: 278

Arg Tyr Ile Trp Met Cys
1               5

<210> SEQ ID NO 279
<211> LENGTH: 6
<212> TYPE: PRT
<213> ORGANISM: Homo sapiens

<400> SEQUENCE: 279

Tyr Ile Trp Met Cys Phe
1               5

<210> SEQ ID NO 280
<211> LENGTH: 6
<212> TYPE: PRT
<213> ORGANISM: Homo sapiens

<400> SEQUENCE: 280

Ile Trp Met Cys Phe Gly
1               5

<210> SEQ ID NO 281
<211> LENGTH: 6
<212> TYPE: PRT
<213> ORGANISM: Homo sapiens

<400> SEQUENCE: 281

Trp Met Cys Phe Gly Gln
1               5

<210> SEQ ID NO 282
<211> LENGTH: 6
<212> TYPE: PRT
```

```
<213> ORGANISM: Homo sapiens

<400> SEQUENCE: 282

Met Cys Phe Gly Gln Gly
1               5

<210> SEQ ID NO 283
<211> LENGTH: 6
<212> TYPE: PRT
<213> ORGANISM: Homo sapiens

<400> SEQUENCE: 283

Cys Phe Gly Gln Gly Thr
1               5

<210> SEQ ID NO 284
<211> LENGTH: 6
<212> TYPE: PRT
<213> ORGANISM: Homo sapiens

<400> SEQUENCE: 284

Phe Gly Gln Gly Thr Gly
1               5

<210> SEQ ID NO 285
<211> LENGTH: 6
<212> TYPE: PRT
<213> ORGANISM: Homo sapiens

<400> SEQUENCE: 285

Gly Gln Gly Thr Gly Arg
1               5

<210> SEQ ID NO 286
<211> LENGTH: 6
<212> TYPE: PRT
<213> ORGANISM: Homo sapiens

<400> SEQUENCE: 286

Gln Gly Thr Gly Arg Gly
1               5

<210> SEQ ID NO 287
<211> LENGTH: 6
<212> TYPE: PRT
<213> ORGANISM: Homo sapiens

<400> SEQUENCE: 287

Gly Thr Gly Arg Gly Gly
1               5

<210> SEQ ID NO 288
<211> LENGTH: 6
<212> TYPE: PRT
<213> ORGANISM: Homo sapiens

<400> SEQUENCE: 288

Thr Gly Arg Gly Gly Tyr
1               5

<210> SEQ ID NO 289
<211> LENGTH: 6
<212> TYPE: PRT
<213> ORGANISM: Homo sapiens

<400> SEQUENCE: 289
```

Gly Arg Gly Gly Tyr Pro
1               5

<210> SEQ ID NO 290
<211> LENGTH: 6
<212> TYPE: PRT
<213> ORGANISM: Homo sapiens

<400> SEQUENCE: 290

Arg Gly Gly Tyr Pro Arg
1               5

<210> SEQ ID NO 291
<211> LENGTH: 6
<212> TYPE: PRT
<213> ORGANISM: Homo sapiens

<400> SEQUENCE: 291

Gly Gly Tyr Pro Arg Pro
1               5

<210> SEQ ID NO 292
<211> LENGTH: 6
<212> TYPE: PRT
<213> ORGANISM: Homo sapiens

<400> SEQUENCE: 292

Gly Tyr Pro Arg Pro Ala
1               5

<210> SEQ ID NO 293
<211> LENGTH: 12
<212> TYPE: PRT
<213> ORGANISM: Homo sapiens

<400> SEQUENCE: 293

Gly Gln Gly Thr Gly Arg Gly Gly Tyr Pro Arg Pro
1               5                   10

<210> SEQ ID NO 294
<211> LENGTH: 101
<212> TYPE: PRT
<213> ORGANISM: Homo sapiens

<400> SEQUENCE: 294

Met Cys Leu Thr Tyr Leu Lys Thr Phe Trp Gly Trp Met Phe Cys Thr
1               5                   10                  15

Ala Trp Gln Leu Tyr Cys Leu Ser Arg Thr Cys Arg Pro Leu Asp Asn
            20                  25                  30

Gly Thr Gly Thr Ser Cys Pro Glu Ser Gln Glu Gln Phe Ala Phe Met
        35                  40                  45

Gly Gly Gln Gln Trp Thr Phe Ser Phe Phe Phe Phe Phe Phe Phe Phe
    50                  55                  60

Phe Phe Glu Met Glu Ser Cys Ser Val Ala Gln Ala Gly Val Gln Gly
65                  70                  75                  80

Thr Ile Ser Ala Pro Cys Asp Leu Arg His Leu Gly Ser Ser Asn Ser
                85                  90                  95

Pro Ala Ser Ala Ser
            100

<210> SEQ ID NO 295
<211> LENGTH: 43

<212> TYPE: PRT
<213> ORGANISM: Homo sapiens

<400> SEQUENCE: 295

Met Cys Leu Thr Tyr Leu Lys Thr Phe Trp Gly Trp Met Phe Cys Thr
1               5                   10                  15

Ala Trp Gln Leu Tyr Cys Leu Ser Arg Thr Cys Arg Pro Leu Asp Asn
                20                  25                  30

Gly Thr Gly Thr Ser Cys Pro Glu Ser Gln Glu
            35                  40

<210> SEQ ID NO 296
<211> LENGTH: 35
<212> TYPE: PRT
<213> ORGANISM: Homo sapiens

<400> SEQUENCE: 296

Glu Met Glu Ser Cys Ser Val Ala Gln Ala Gly Val Gln Gly Thr Ile
1               5                   10                  15

Ser Ala Pro Cys Asp Leu Arg His Leu Gly Ser Ser Asn Ser Pro Ala
                20                  25                  30

Ser Ala Ser
        35

<210> SEQ ID NO 297
<211> LENGTH: 20
<212> TYPE: PRT
<213> ORGANISM: Homo sapiens

<400> SEQUENCE: 297

Arg Thr Cys Arg Pro Leu Asp Asn Gly Thr Gly Thr Ser Cys Pro Glu
1               5                   10                  15

Ser Gln Glu Gln
            20

<210> SEQ ID NO 298
<211> LENGTH: 6
<212> TYPE: PRT
<213> ORGANISM: Homo sapiens

<400> SEQUENCE: 298

Met Cys Leu Thr Tyr Leu
1               5

<210> SEQ ID NO 299
<211> LENGTH: 6
<212> TYPE: PRT
<213> ORGANISM: Homo sapiens

<400> SEQUENCE: 299

Cys Leu Thr Tyr Leu Lys
1               5

<210> SEQ ID NO 300
<211> LENGTH: 6
<212> TYPE: PRT
<213> ORGANISM: Homo sapiens

<400> SEQUENCE: 300

Leu Thr Tyr Leu Lys Thr
1               5

<210> SEQ ID NO 301

```
<211> LENGTH: 6
<212> TYPE: PRT
<213> ORGANISM: Homo sapiens

<400> SEQUENCE: 301

Thr Tyr Leu Lys Thr Phe
1               5

<210> SEQ ID NO 302
<211> LENGTH: 6
<212> TYPE: PRT
<213> ORGANISM: Homo sapiens

<400> SEQUENCE: 302

Tyr Leu Lys Thr Phe Trp
1               5

<210> SEQ ID NO 303
<211> LENGTH: 6
<212> TYPE: PRT
<213> ORGANISM: Homo sapiens

<400> SEQUENCE: 303

Leu Lys Thr Phe Trp Gly
1               5

<210> SEQ ID NO 304
<211> LENGTH: 6
<212> TYPE: PRT
<213> ORGANISM: Homo sapiens

<400> SEQUENCE: 304

Lys Thr Phe Trp Gly Trp
1               5

<210> SEQ ID NO 305
<211> LENGTH: 6
<212> TYPE: PRT
<213> ORGANISM: Homo sapiens

<400> SEQUENCE: 305

Thr Phe Trp Gly Trp Met
1               5

<210> SEQ ID NO 306
<211> LENGTH: 6
<212> TYPE: PRT
<213> ORGANISM: Homo sapiens

<400> SEQUENCE: 306

Phe Trp Gly Trp Met Phe
1               5

<210> SEQ ID NO 307
<211> LENGTH: 6
<212> TYPE: PRT
<213> ORGANISM: Homo sapiens

<400> SEQUENCE: 307

Trp Gly Trp Met Phe Cys
1               5

<210> SEQ ID NO 308
<211> LENGTH: 6
<212> TYPE: PRT
<213> ORGANISM: Homo sapiens
```

```
<400> SEQUENCE: 308

Gly Trp Met Phe Cys Thr
1               5

<210> SEQ ID NO 309
<211> LENGTH: 6
<212> TYPE: PRT
<213> ORGANISM: Homo sapiens

<400> SEQUENCE: 309

Trp Met Phe Cys Thr Ala
1               5

<210> SEQ ID NO 310
<211> LENGTH: 6
<212> TYPE: PRT
<213> ORGANISM: Homo sapiens

<400> SEQUENCE: 310

Met Phe Cys Thr Ala Trp
1               5

<210> SEQ ID NO 311
<211> LENGTH: 6
<212> TYPE: PRT
<213> ORGANISM: Homo sapiens

<400> SEQUENCE: 311

Phe Cys Thr Ala Trp Gln
1               5

<210> SEQ ID NO 312
<211> LENGTH: 6
<212> TYPE: PRT
<213> ORGANISM: Homo sapiens

<400> SEQUENCE: 312

Cys Thr Ala Trp Gln Leu
1               5

<210> SEQ ID NO 313
<211> LENGTH: 6
<212> TYPE: PRT
<213> ORGANISM: Homo sapiens

<400> SEQUENCE: 313

Thr Ala Trp Gln Leu Tyr
1               5

<210> SEQ ID NO 314
<211> LENGTH: 6
<212> TYPE: PRT
<213> ORGANISM: Homo sapiens

<400> SEQUENCE: 314

Ala Trp Gln Leu Tyr Cys
1               5

<210> SEQ ID NO 315
<211> LENGTH: 6
<212> TYPE: PRT
<213> ORGANISM: Homo sapiens

<400> SEQUENCE: 315
```

Trp Gln Leu Tyr Cys Leu
1               5

<210> SEQ ID NO 316
<211> LENGTH: 6
<212> TYPE: PRT
<213> ORGANISM: Homo sapiens

<400> SEQUENCE: 316

Gln Leu Tyr Cys Leu Ser
1               5

<210> SEQ ID NO 317
<211> LENGTH: 6
<212> TYPE: PRT
<213> ORGANISM: Homo sapiens

<400> SEQUENCE: 317

Leu Tyr Cys Leu Ser Arg
1               5

<210> SEQ ID NO 318
<211> LENGTH: 6
<212> TYPE: PRT
<213> ORGANISM: Homo sapiens

<400> SEQUENCE: 318

Tyr Cys Leu Ser Arg Thr
1               5

<210> SEQ ID NO 319
<211> LENGTH: 6
<212> TYPE: PRT
<213> ORGANISM: Homo sapiens

<400> SEQUENCE: 319

Cys Leu Ser Arg Thr Cys
1               5

<210> SEQ ID NO 320
<211> LENGTH: 6
<212> TYPE: PRT
<213> ORGANISM: Homo sapiens

<400> SEQUENCE: 320

Leu Ser Arg Thr Cys Arg
1               5

<210> SEQ ID NO 321
<211> LENGTH: 6
<212> TYPE: PRT
<213> ORGANISM: Homo sapiens

<400> SEQUENCE: 321

Ser Arg Thr Cys Arg Pro
1               5

<210> SEQ ID NO 322
<211> LENGTH: 6
<212> TYPE: PRT
<213> ORGANISM: Homo sapiens

<400> SEQUENCE: 322

Arg Thr Cys Arg Pro Leu
1               5

```
<210> SEQ ID NO 323
<211> LENGTH: 6
<212> TYPE: PRT
<213> ORGANISM: Homo sapiens

<400> SEQUENCE: 323

Thr Cys Arg Pro Leu Asp
1               5

<210> SEQ ID NO 324
<211> LENGTH: 6
<212> TYPE: PRT
<213> ORGANISM: Homo sapiens

<400> SEQUENCE: 324

Cys Arg Pro Leu Asp Asn
1               5

<210> SEQ ID NO 325
<211> LENGTH: 6
<212> TYPE: PRT
<213> ORGANISM: Homo sapiens

<400> SEQUENCE: 325

Arg Pro Leu Asp Asn Gly
1               5

<210> SEQ ID NO 326
<211> LENGTH: 6
<212> TYPE: PRT
<213> ORGANISM: Homo sapiens

<400> SEQUENCE: 326

Pro Leu Asp Asn Gly Thr
1               5

<210> SEQ ID NO 327
<211> LENGTH: 6
<212> TYPE: PRT
<213> ORGANISM: Homo sapiens

<400> SEQUENCE: 327

Leu Asp Asn Gly Thr Gly
1               5

<210> SEQ ID NO 328
<211> LENGTH: 6
<212> TYPE: PRT
<213> ORGANISM: Homo sapiens

<400> SEQUENCE: 328

Asp Asn Gly Thr Gly Thr
1               5

<210> SEQ ID NO 329
<211> LENGTH: 6
<212> TYPE: PRT
<213> ORGANISM: Homo sapiens

<400> SEQUENCE: 329

Asn Gly Thr Gly Thr Ser
1               5

<210> SEQ ID NO 330
<211> LENGTH: 6
```

```
<212> TYPE: PRT
<213> ORGANISM: Homo sapiens

<400> SEQUENCE: 330

Gly Thr Gly Thr Ser Cys
1               5

<210> SEQ ID NO 331
<211> LENGTH: 6
<212> TYPE: PRT
<213> ORGANISM: Homo sapiens

<400> SEQUENCE: 331

Thr Gly Thr Ser Cys Pro
1               5

<210> SEQ ID NO 332
<211> LENGTH: 6
<212> TYPE: PRT
<213> ORGANISM: Homo sapiens

<400> SEQUENCE: 332

Gly Thr Ser Cys Pro Glu
1               5

<210> SEQ ID NO 333
<211> LENGTH: 6
<212> TYPE: PRT
<213> ORGANISM: Homo sapiens

<400> SEQUENCE: 333

Thr Ser Cys Pro Glu Ser
1               5

<210> SEQ ID NO 334
<211> LENGTH: 6
<212> TYPE: PRT
<213> ORGANISM: Homo sapiens

<400> SEQUENCE: 334

Ser Cys Pro Glu Ser Gln
1               5

<210> SEQ ID NO 335
<211> LENGTH: 6
<212> TYPE: PRT
<213> ORGANISM: Homo sapiens

<400> SEQUENCE: 335

Cys Pro Glu Ser Gln Glu
1               5

<210> SEQ ID NO 336
<211> LENGTH: 6
<212> TYPE: PRT
<213> ORGANISM: Homo sapiens

<400> SEQUENCE: 336

Pro Glu Ser Gln Glu Gln
1               5

<210> SEQ ID NO 337
<211> LENGTH: 6
<212> TYPE: PRT
<213> ORGANISM: Homo sapiens
```

```
<400> SEQUENCE: 337

Glu Met Glu Ser Cys Ser
1               5

<210> SEQ ID NO 338
<211> LENGTH: 6
<212> TYPE: PRT
<213> ORGANISM: Homo sapiens

<400> SEQUENCE: 338

Met Glu Ser Cys Ser Val
1               5

<210> SEQ ID NO 339
<211> LENGTH: 6
<212> TYPE: PRT
<213> ORGANISM: Homo sapiens

<400> SEQUENCE: 339

Glu Ser Cys Ser Val Ala
1               5

<210> SEQ ID NO 340
<211> LENGTH: 6
<212> TYPE: PRT
<213> ORGANISM: Homo sapiens

<400> SEQUENCE: 340

Ser Cys Ser Val Ala Gln
1               5

<210> SEQ ID NO 341
<211> LENGTH: 6
<212> TYPE: PRT
<213> ORGANISM: Homo sapiens

<400> SEQUENCE: 341

Cys Ser Val Ala Gln Ala
1               5

<210> SEQ ID NO 342
<211> LENGTH: 6
<212> TYPE: PRT
<213> ORGANISM: Homo sapiens

<400> SEQUENCE: 342

Ser Val Ala Gln Ala Gly
1               5

<210> SEQ ID NO 343
<211> LENGTH: 6
<212> TYPE: PRT
<213> ORGANISM: Homo sapiens

<400> SEQUENCE: 343

Val Ala Gln Ala Gly Val
1               5

<210> SEQ ID NO 344
<211> LENGTH: 6
<212> TYPE: PRT
<213> ORGANISM: Homo sapiens

<400> SEQUENCE: 344

Ala Gln Ala Gly Val Gln
```

```
<210> SEQ ID NO 345
<211> LENGTH: 6
<212> TYPE: PRT
<213> ORGANISM: Homo sapiens

<400> SEQUENCE: 345

Gln Ala Gly Val Gln Gly
1               5

<210> SEQ ID NO 346
<211> LENGTH: 6
<212> TYPE: PRT
<213> ORGANISM: Homo sapiens

<400> SEQUENCE: 346

Ala Gly Val Gln Gly Thr
1               5

<210> SEQ ID NO 347
<211> LENGTH: 6
<212> TYPE: PRT
<213> ORGANISM: Homo sapiens

<400> SEQUENCE: 347

Gly Val Gln Gly Thr Ile
1               5

<210> SEQ ID NO 348
<211> LENGTH: 6
<212> TYPE: PRT
<213> ORGANISM: Homo sapiens

<400> SEQUENCE: 348

Val Gln Gly Thr Ile Ser
1               5

<210> SEQ ID NO 349
<211> LENGTH: 6
<212> TYPE: PRT
<213> ORGANISM: Homo sapiens

<400> SEQUENCE: 349

Gln Gly Thr Ile Ser Ala
1               5

<210> SEQ ID NO 350
<211> LENGTH: 6
<212> TYPE: PRT
<213> ORGANISM: Homo sapiens

<400> SEQUENCE: 350

Gly Thr Ile Ser Ala Pro
1               5

<210> SEQ ID NO 351
<211> LENGTH: 6
<212> TYPE: PRT
<213> ORGANISM: Homo sapiens

<400> SEQUENCE: 351

Thr Ile Ser Ala Pro Cys
1               5
```

<210> SEQ ID NO 352
<211> LENGTH: 6
<212> TYPE: PRT
<213> ORGANISM: Homo sapiens

<400> SEQUENCE: 352

Ile Ser Ala Pro Cys Asp
1               5

<210> SEQ ID NO 353
<211> LENGTH: 6
<212> TYPE: PRT
<213> ORGANISM: Homo sapiens

<400> SEQUENCE: 353

Ser Ala Pro Cys Asp Leu
1               5

<210> SEQ ID NO 354
<211> LENGTH: 6
<212> TYPE: PRT
<213> ORGANISM: Homo sapiens

<400> SEQUENCE: 354

Ala Pro Cys Asp Leu Arg
1               5

<210> SEQ ID NO 355
<211> LENGTH: 6
<212> TYPE: PRT
<213> ORGANISM: Homo sapiens

<400> SEQUENCE: 355

Pro Cys Asp Leu Arg His
1               5

<210> SEQ ID NO 356
<211> LENGTH: 6
<212> TYPE: PRT
<213> ORGANISM: Homo sapiens

<400> SEQUENCE: 356

Cys Asp Leu Arg His Leu
1               5

<210> SEQ ID NO 357
<211> LENGTH: 6
<212> TYPE: PRT
<213> ORGANISM: Homo sapiens

<400> SEQUENCE: 357

Asp Leu Arg His Leu Gly
1               5

<210> SEQ ID NO 358
<211> LENGTH: 6
<212> TYPE: PRT
<213> ORGANISM: Homo sapiens

<400> SEQUENCE: 358

Leu Arg His Leu Gly Ser
1               5

<210> SEQ ID NO 359
<211> LENGTH: 6
<212> TYPE: PRT

<213> ORGANISM: Homo sapiens

<400> SEQUENCE: 359

Arg His Leu Gly Ser Ser
1               5

<210> SEQ ID NO 360
<211> LENGTH: 6
<212> TYPE: PRT
<213> ORGANISM: Homo sapiens

<400> SEQUENCE: 360

His Leu Gly Ser Ser Asn
1               5

<210> SEQ ID NO 361
<211> LENGTH: 6
<212> TYPE: PRT
<213> ORGANISM: Homo sapiens

<400> SEQUENCE: 361

Leu Gly Ser Ser Asn Ser
1               5

<210> SEQ ID NO 362
<211> LENGTH: 6
<212> TYPE: PRT
<213> ORGANISM: Homo sapiens

<400> SEQUENCE: 362

Gly Ser Ser Asn Ser Pro
1               5

<210> SEQ ID NO 363
<211> LENGTH: 6
<212> TYPE: PRT
<213> ORGANISM: Homo sapiens

<400> SEQUENCE: 363

Ser Ser Asn Ser Pro Ala
1               5

<210> SEQ ID NO 364
<211> LENGTH: 6
<212> TYPE: PRT
<213> ORGANISM: Homo sapiens

<400> SEQUENCE: 364

Ser Asn Ser Pro Ala Ser
1               5

<210> SEQ ID NO 365
<211> LENGTH: 6
<212> TYPE: PRT
<213> ORGANISM: Homo sapiens

<400> SEQUENCE: 365

Asn Ser Pro Ala Ser Ala
1               5

<210> SEQ ID NO 366
<211> LENGTH: 6
<212> TYPE: PRT
<213> ORGANISM: Homo sapiens

<400> SEQUENCE: 366

Ser Pro Ala Ser Ala Ser
1               5

<210> SEQ ID NO 367
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
gaacaggaat gcaaaggctt tg                                              22

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
gcacccagct gaccatgtc                                                  19

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369
ccggtggatt tttgcttctg                                                 20

<210> SEQ ID NO 370
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
gcctcttgtt ggactggaga ga                                              22

<210> SEQ ID NO 371
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371 cataccttg ccagcagagt ca                                               22

<210> SEQ ID NO 372
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 372
ggcattcatt tccctcagca t                                              21
```

COMPOSITIONS AND METHODS OF USE FOR MODULATORS OF POLYPEPTIDES AND POLYNUCLEOTIDES IN TREATING BREAST CANCER AND MELANOMA

This application claims the benefit of priority to three U.S. provisional applications, which are all incorporated by reference in their entirety: No. 60/774,238, "Compositions and Methods of Use for Modulators of gi27498157 in Treating Disease," filed Feb. 17, 2006; No. 60/774,268, "Compositions and Methods of Use for Modulators of Novel Polynucleotides and Polypeptides in Treating Disease," filed Feb. 17, 2006; and No. 60/796,852, "Compositions and Methods of Use for Modulators of a Novel Polynucleotide and Polypeptide in Treating Proliferative Diseases," filed May 3, 2006.

TECHNICAL FIELD

This invention relates to polynucleotides and polypeptides found to be over expressed and/or amplified in certain populations of cancer patient tissue samples as compared to counterpart normal tissues. The invention also relates to modulators, for example, antibodies, and soluble receptors, of these polynucleotides and polypeptides, which specifically bind to and/or interfere with the binding or activity of these polynucleotides, their complements, polypeptides; and fragments and variants of the polynucleotides, complements, and polypeptides. The invention further relates to compositions containing such polynucleotides, complements, polypeptides, and their variants and fragments; as well as their modulators. It also relates to uses for such compositions in treating or preventing certain cancers and proliferative diseases. The invention provides diagnostic kits and tests for such proliferative disorders.

BACKGROUND

Each year, more than ten million new cases of cancer are diagnosed, a number that is expected to approach fifteen million by the year 2015 (Stewart, B W and Kleihues, P. (2003) World Cancer Report World Health Organization, IARC). Important for improving the quality of life and survivorship of individuals diagnosed with cancer, is the availability of new tools for the diagnosis and treatment of cancer. Currently used detection methods include imaging (CAT scan, EUS, ERCP), and histopathology, frequently involving the use of antibodies for cancer-specific markers on a biopsy specimen. Diagnosis of cancer may also involve the detection of cancer-specific markers in the serum.

The use of cancer type-specific drugs and biologics has also revolutionized the treatment of cancers. Older, non-surgical treatments typically involve powerful chemotherapeutic agents and radiotherapeutic approaches that often result in side-effects that lower the quality of life for the patient. The use of cancer tumor-type specific drugs; including antibodies, polypeptides, soluble receptors, small molecule drugs, aptamers, and polynucleotide-based reagents, has the potential to significantly improve the treatment outlook for all types of cancers, whether these treatments are used alone or in combination with existing therapies. The potential for improved treatment also increases with early detection.

The American Cancer Society has determined that breast cancer is the second leading cause of cancer death in women. Currently, there is a 1 in 33 chance that breast cancer will be responsible for a woman's death. Also according to the American Cancer Society, melanoma, which is the most deadly type of skin cancer, is increasing in frequency among the population in the U.S. In 2007, it is estimated that there will be over 59,000 new cases of melanoma diagnosed and over 8,100 deaths resulting from melanoma.

The success of available treatments for breast cancer may be enhanced by its early detection. Detection of cancer cell-specific biomarkers provides an effective screening strategy for a number of cancers. Their early detection provides not only early diagnosis, but also the ability to screen for and detect post-operative residual tumor cells, and for occult metastases, an early indicator of tumor recurrence. Early detection can thus improve survival in patients before diagnosis, while undergoing treatment, and while in remission.

BRIEF DESCRIPTION OF THE DRAWINGS AND TABLES

In the figure, relative gene expression is shown on the Y-axis, while breast cancer tissue and normal breast tissue specimens are indicated by specimen number on the X-axis. Normal tissue specimens are labeled "Normal." Gene expression values shown are relative to GAPDH, a housekeeping gene maintained at constant levels in all tissues. Each quantitative real time PCR was performed in duplicate, as represented by paired bars for each sample. The results show that a gene in cluster 192473 is overexpressed in eight of 19 breast cancer samples examined and in none of two normal breast cancer samples examined.

Figure 1:
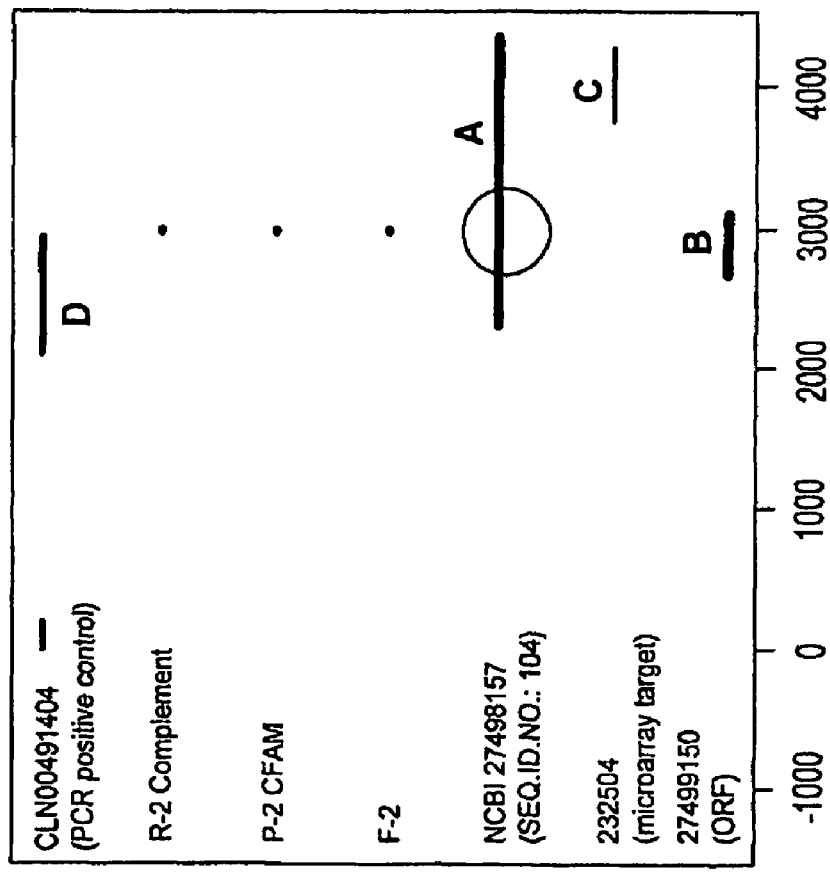
FIG. 1 shows an exon map providing the genomic locations of certain disclosed nucleotide sequences assigned to cluster 192473. The horizontal axis is a scaled version of the genome which considers all the introns to have equal lengths. Above and parallel to the horizontal axis, are a number of lines, each representing a nucleotide sequence in cluster 192473 and its relative location. Each of these lines is annotated by a label on the far left of the figure, identifying each nucleotide sequence. The location of the full-length nucleotide sequence of NCBI clone 27498157, which is contained within cluster 192473, is designated by line A. The relative location of the polynucleotide target sequence of the real-time PCR probes (Taqman probe SV and Taqman probe PD) used to analyze gene expression at cluster 192473 is indicated by the encircled area on line A. Line B represents the sequence of clone 27499150, which also contains the open reading frame (ORF) of NCBI 27498157. Line C represents the target polynucleotide sequence recognized by the Affymetrix microarray hybridization probe, 232504_at which contained a set of 11 matched and 11 mismatched 25-mer oligonucleotides, used to detect expression in tissue samples of genes in cluster 192473. The nucleotide sequence of probe 232504_at overlaps with the 3' untranslated region (UTR) of NCBI 27498157. The letter D indicates the nucleotide sequence encoded by clone, CLN00491404. Depicted beneath the CLN00491404 sequence, are shown the location of forward (F-2) and reverse (R-2 complement) primers and probes (P-2 CFAM) used for quantitative real time PCR analysis are also shown.
Figure 3:
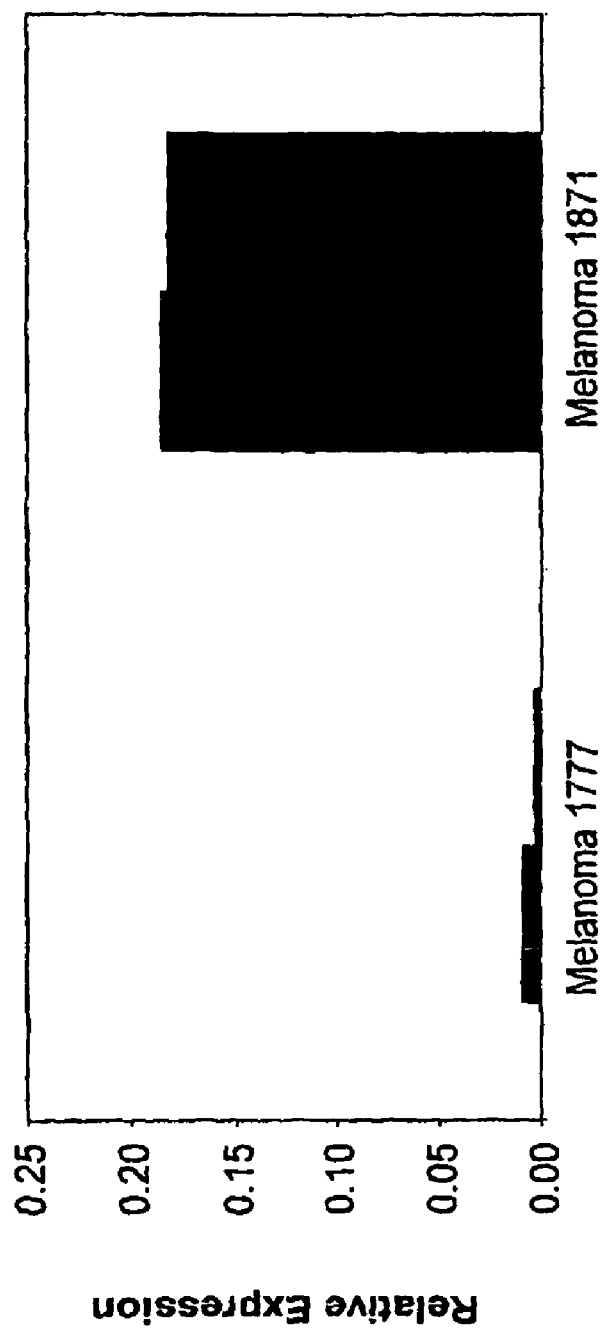

FIG. 3 shows the expression level of cluster 192473 in 2 melanoma tissues as detected by quantitative real time PCR using probes F-2, R-2 complement, and P-2 CFAM, all of which are specific to genes in cluster 192473 and described in FIG. 1.

In FIG. 3, relative gene expression is shown on the Y-axis, while melanoma cancer tissue samples are indicated by specimen number on the X-axis. Gene expression values shown are relative to GAPDH, a housekeeping gene maintained at constant levels in all tissues. Each quantitative real time PCR reaction was performed in duplicate, as represented by paired bars for each sample. The results show that a gene in cluster 192473 is overexpressed in one of two melanoma cancer samples examined.

Figure 4:
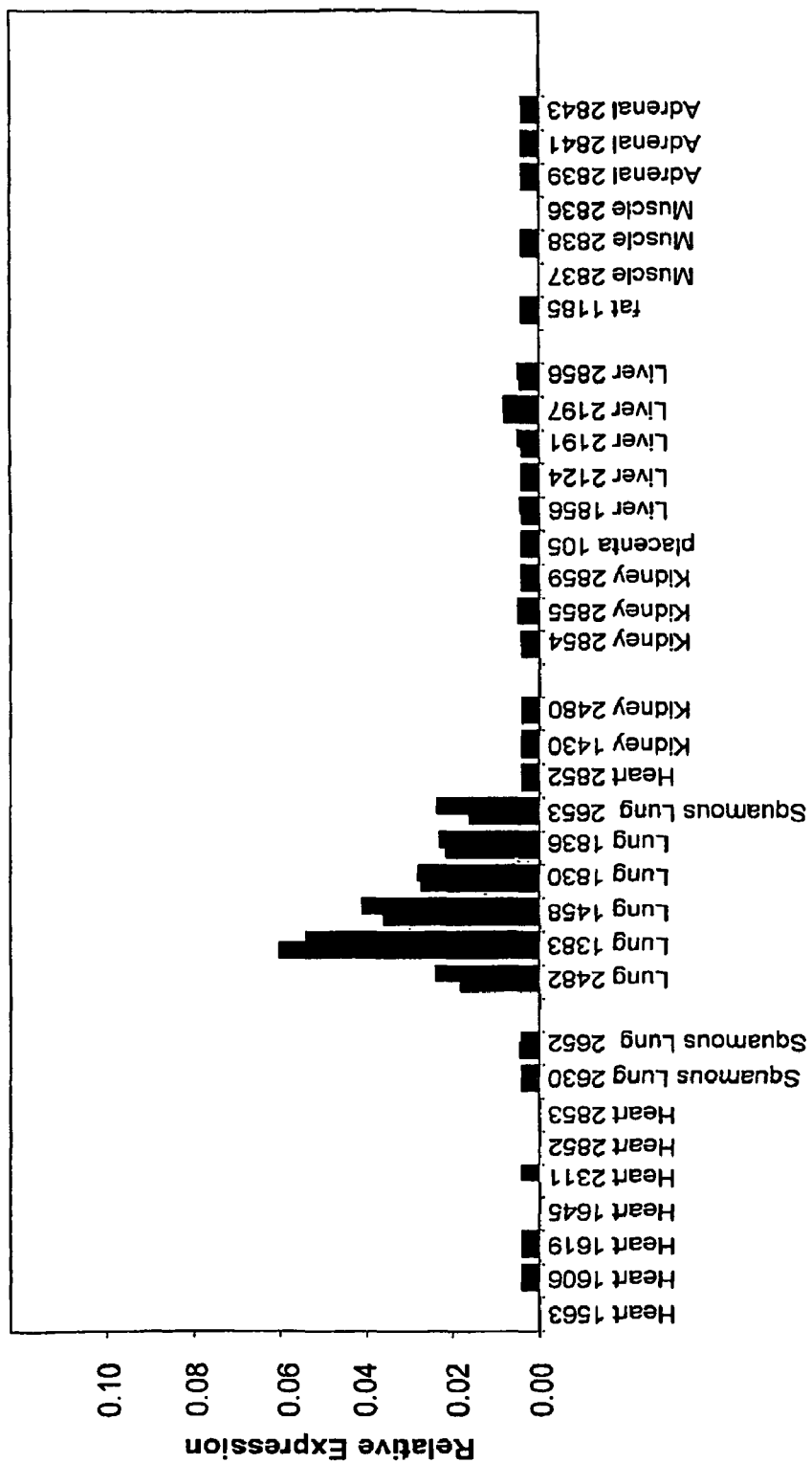

FIG. 4 shows the expression level of cluster 192473 in seven normal heart samples; five normal kidney samples; one normal placenta sample; five normal liver samples; one normal fat samples; three normal muscle samples; and three normal adrenal gland samples, as detected by quantitative real time PCR using probes F-2, R-2 complement, and P-2 CFAM, all of which are specific to genes in cluster 192473 and described in FIG. 1. Each quantitative real time PCR was performed in duplicate, as represented by paired bars for each sample.

Figure 5:
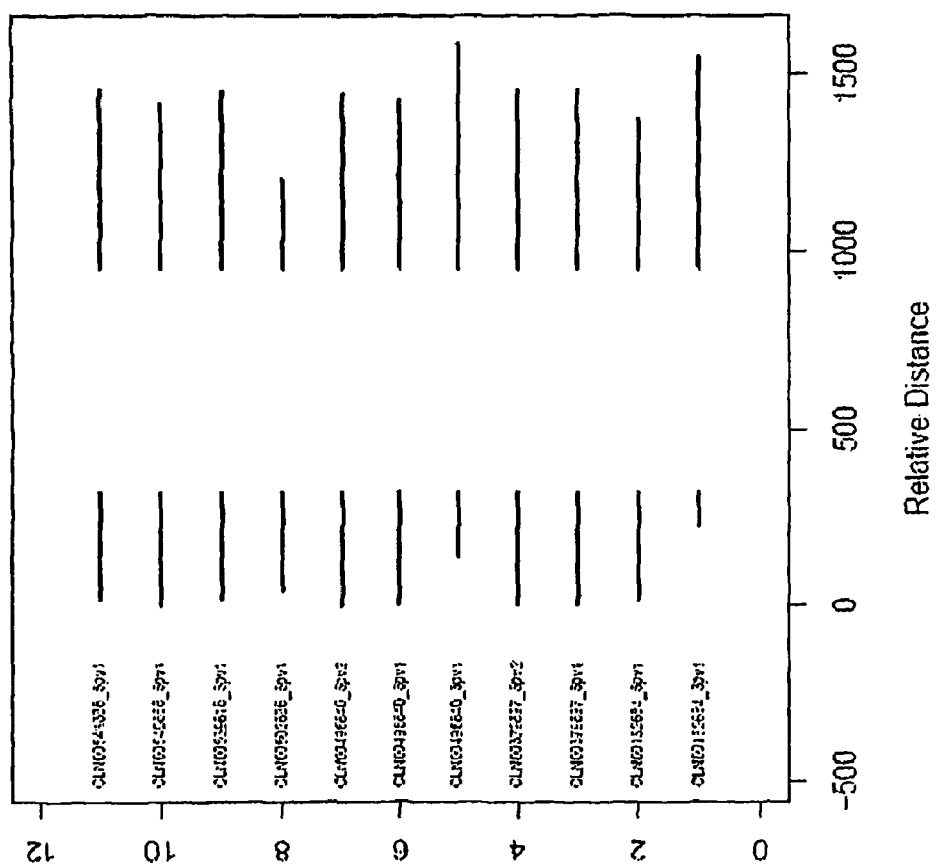

FIG. 5 shows an exon map, as described in FIG. 1, but providing the genomic locations of various clones assigned to cluster 800228. Each line represents the location of a nucleotide sequence, identified by a clone number, such as CLN00541308__5pv1, with a gap representing the location of the intron. The designation, "5pv1" represents the sequence identified in the first round of 5' end sequencing. Similarly, "5pv2" represents the sequence identified in the second round of 5' end sequencing. The designation, "3pv1" represents the sequence identified in the first round of 3' end sequencing and "3pv2" represents the sequence identified in the second round of 3' end sequencing. The overlap of the 5' end sequencing and the 3' end sequencing provided confidence that the full-length sequence of the clone had been obtained.

Figure 6:
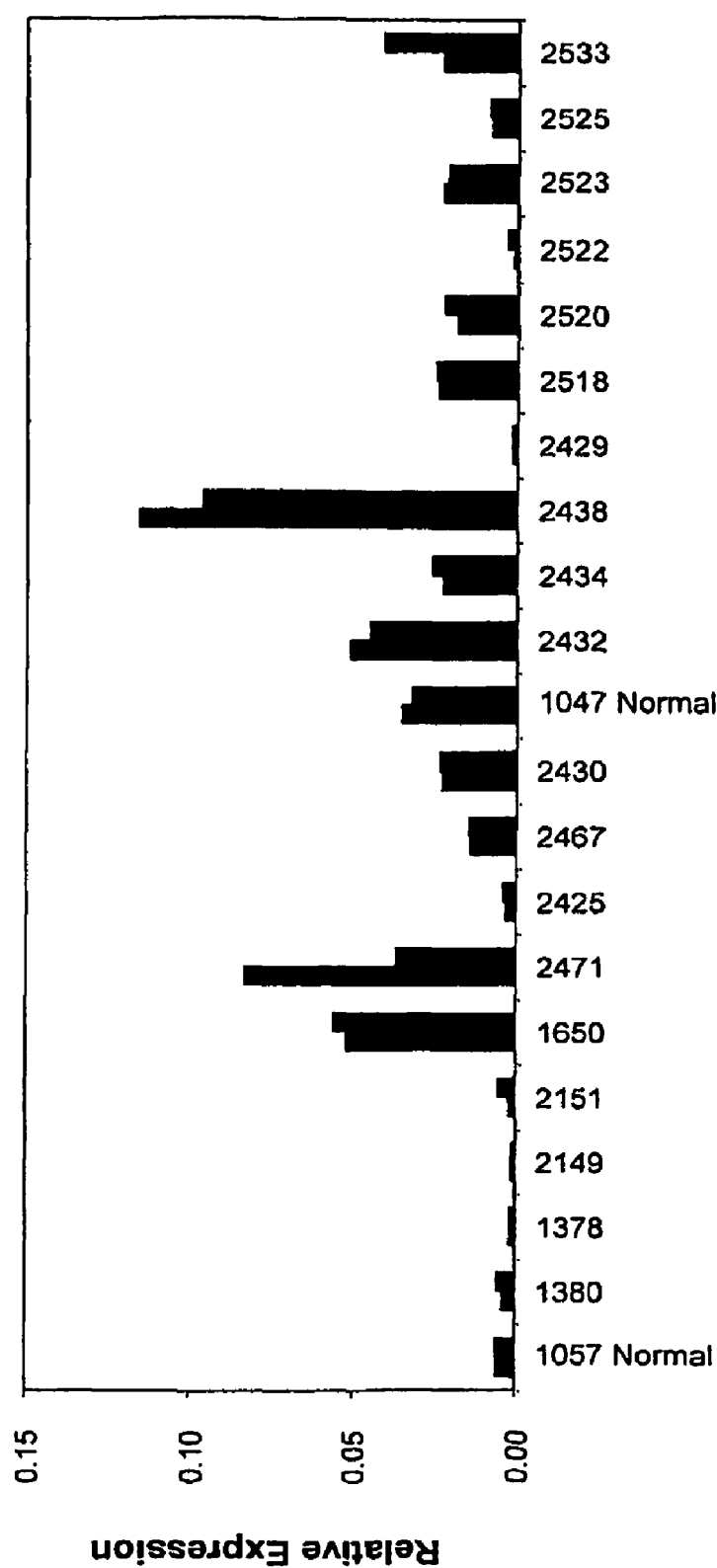

FIG. 6 shows the expression level of cluster 800228 in 19 breast cancer tissues and in two normal breast tissues as detected by quantitative real time PCR using probes specific to genes in cluster 800228.

In FIG. 6, relative gene expression is shown on the Y-axis, while breast cancer tissue and normal breast tissue specimens are indicated by specimen number on the X-axis. Gene expression values shown are relative to GAPDH, a housekeeping gene maintained at constant levels in all tissues. Each quantitative real time PCR was performed in duplicate, as represented by paired bars for each sample. The results show that a gene in cluster 800228 is overexpressed in 12 of 19 breast cancer samples examined and in one of two normal breast cancer samples examined.

Figure 7:
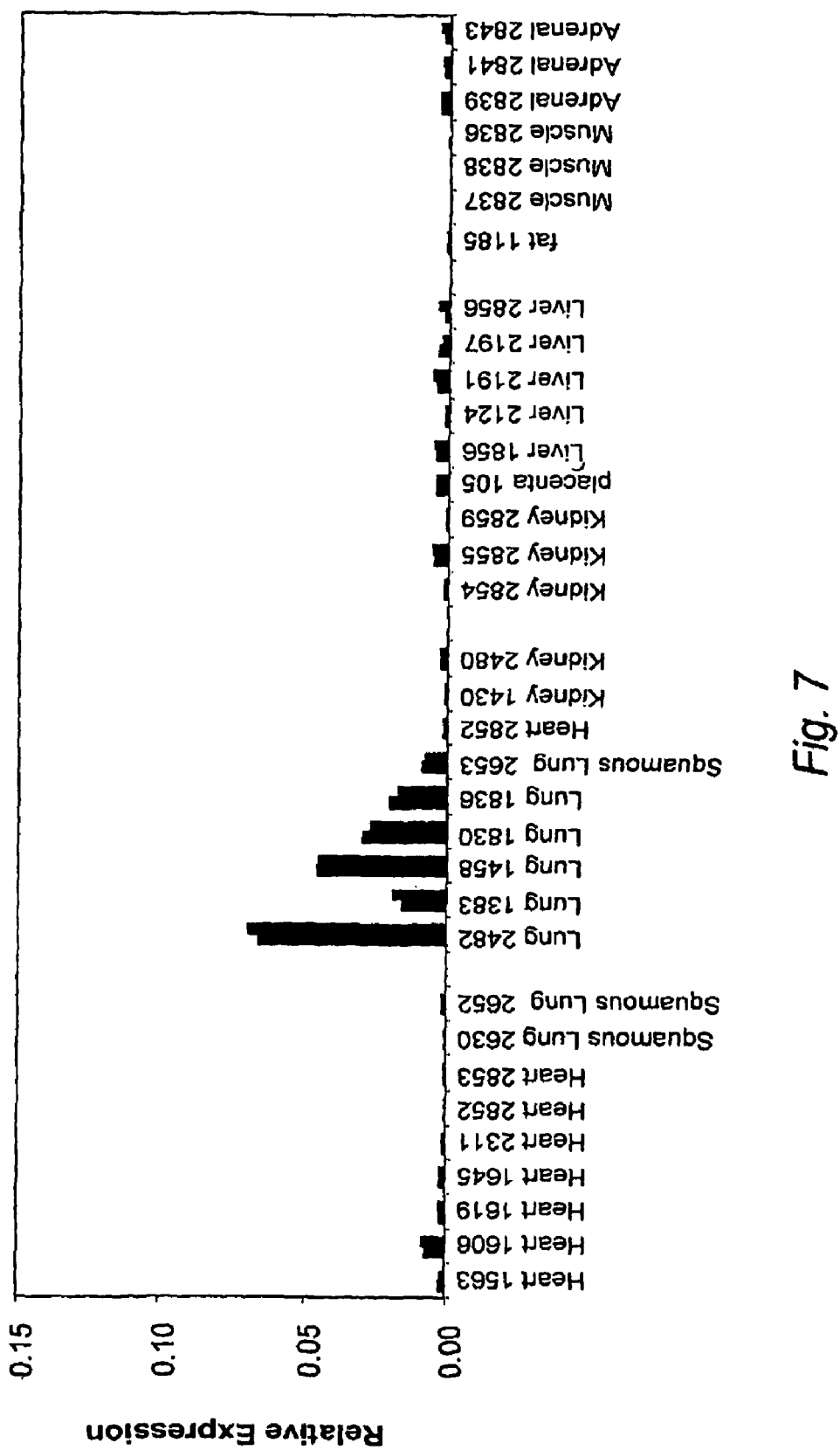

FIG. 7 shows the expression level of cluster 800228 in seven normal heart samples; five normal kidney samples; one normal placenta sample; five normal liver samples; one normal fat samples; three normal muscle samples; and three normal adrenal gland samples as detected by quantitative real time PCR using probes specific to genes in cluster 800228. Each quantitative real time PCR was performed in duplicate, as represented by paired bars for each sample.

FIG. 8 shows an amino acid sequence alignment of the human CLN00496840 amino acid sequence, SEQ ID NO: 111 (indicated as "CLN004," top sequence) and the corresponding chimpanzee amino acid sequence, SEQ ID NO: 165 (bottom sequence), which are encoded by nucleotide sequences assigned to cluster 800228, and represented by SEQ. ID. NOS.: 106 and 109, respectively.

Figure 9:
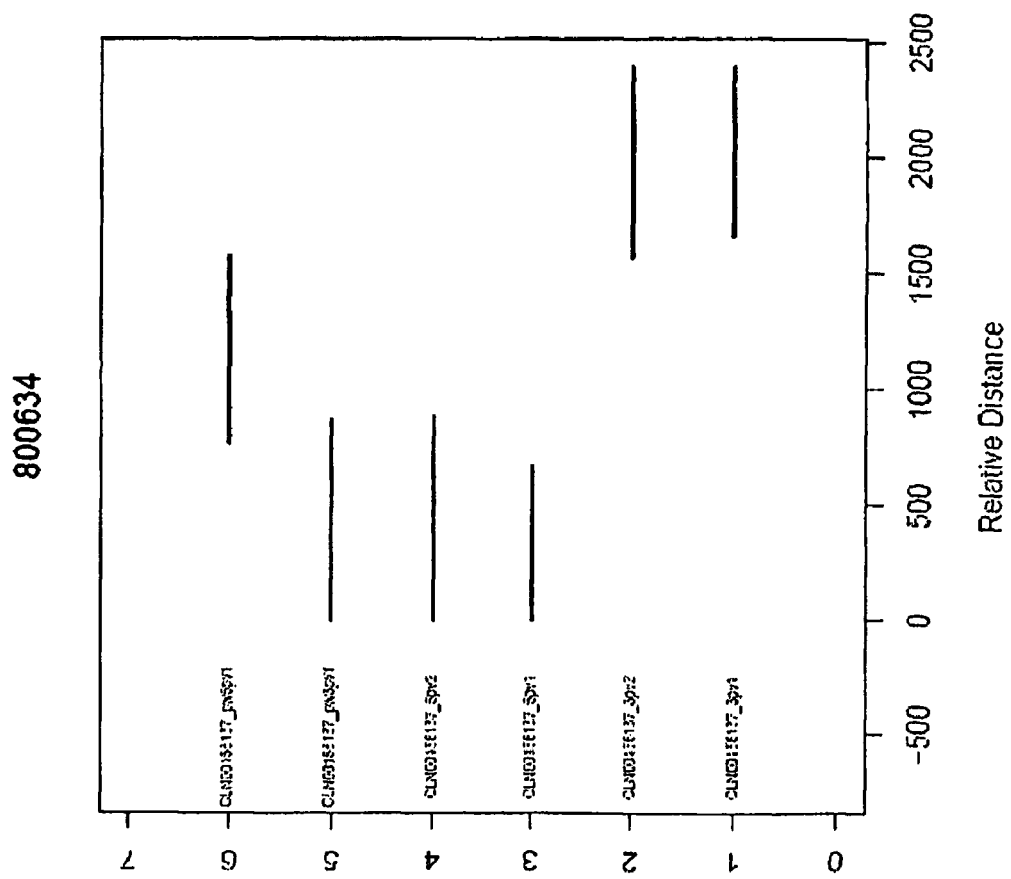

FIG. 9 shows an exon map providing the genomic location of certain nucleotide sequences assigned to cluster 800634. The horizontal axis is a scaled version of the genome which considers all the introns to have equal lengths. Each line represents a sequence of a clone, CLN00156137, obtained from different rounds of sequencing. "5pv1" represents the read from the first round of 5' end sequencing; "5pv2" represents the read from the second round of 5' end sequencing; "3pv1" represents the first round of 3' end sequencing; "3pv2" represents the second round of the 3' end sequencing; "pw" represents the read from primer walking. Based on these sequencing rounds, the full length of CLN00156137 (SEQ. ID. NO.: 179) was obtained. Furthermore, the circled area depicted for CLN00154127, represents the nucleotide sequence that was amplified in the PCR analysis of gene expression of the gene of cluster 800634, as shown in the figures below.

Figure 10:
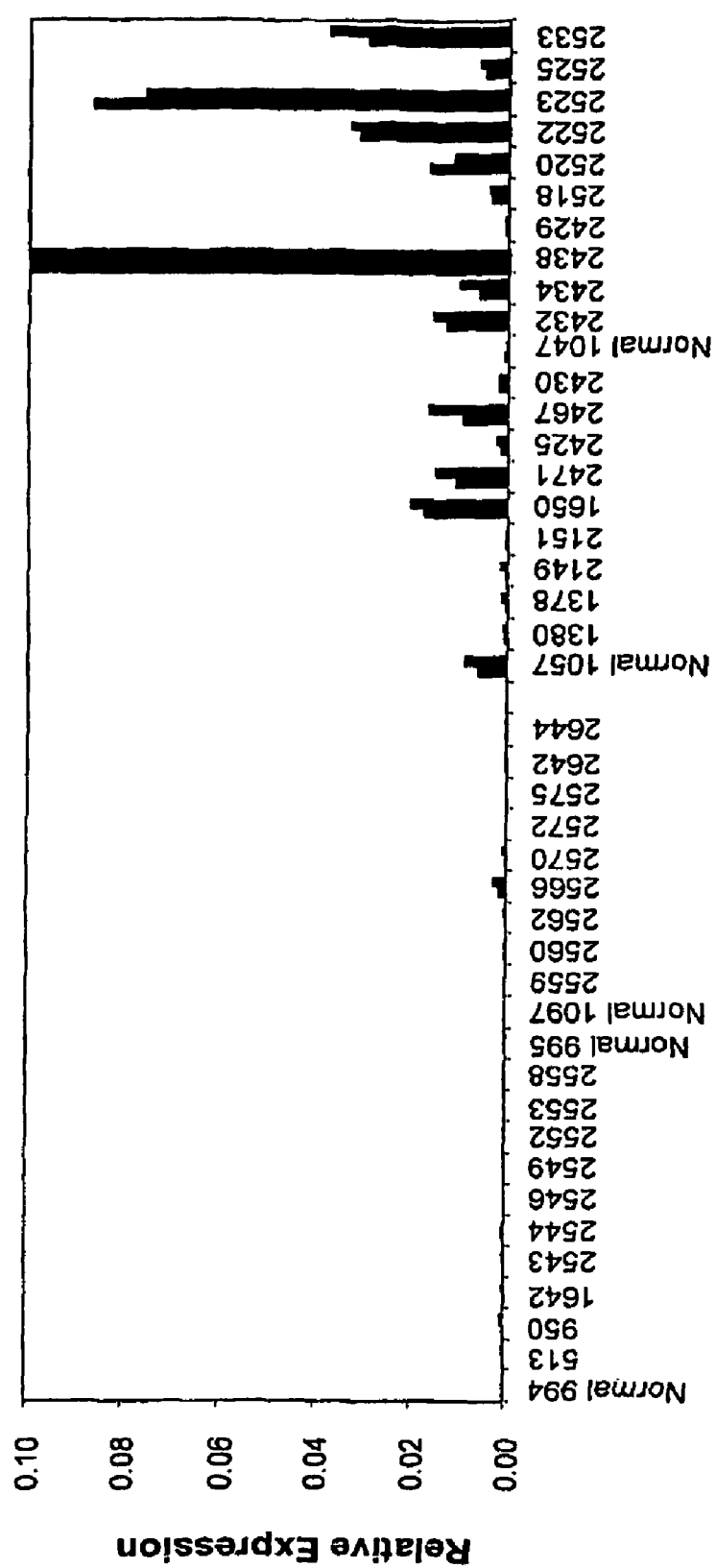

FIG. 10 shows the expression level of cluster 800634 in 19 breast cancer tissues and in 2 normal breast tissues, and in 19 prostate cancer tissues and 3 normal prostate tissues as detected by quantitative real time PCR using probes specific to genes in cluster 800634.

In FIG. 10, relative gene expression is shown on the Y-axis, while breast cancer tissue and normal breast tissue specimens are indicated by specimen number on the right half of the X-axis. Prostate cancer and normal prostate tissues are indicated by specimen number on the left half of the X-axis. Gene expression values shown are relative to GAPDH, a housekeeping gene maintained at constant levels in all tissues. Each quantitative real time PCR was performed in duplicate, as represented by paired bars for each sample.

The results show that a gene in cluster 800634 is overexpressed in 12 of 19 breast cancer samples examined and in one of two normal breast cancer samples examined. The results also show that a gene in cluster 800634 is overexpressed in none of 19 prostate cancer samples examined and in none of three prostate cancer samples examined.

Figure 11:
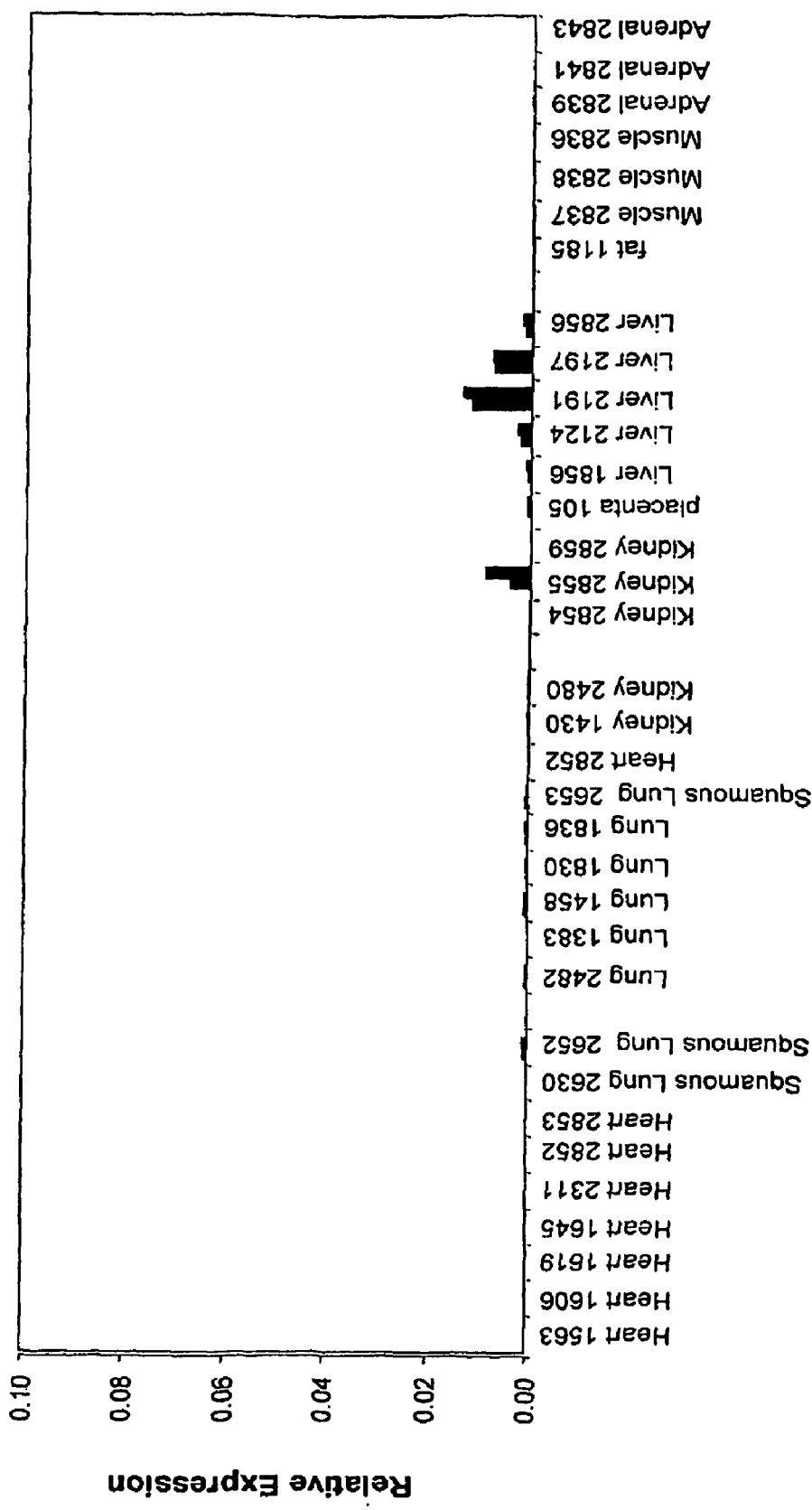

FIG. 11 shows the expression level of cluster 800634 in seven normal heart samples; five normal kidney samples; one normal placenta sample; five normal liver samples; one normal fat sample; three normal muscle samples; and three normal adrenal gland samples as detected by quantitative real time PCR using probes specific to genes in cluster 800634.

In FIG. 11, relative gene expression is shown on the Y-axis, while various normal tissue samples are indicated by specimen number on the X-axis. Gene expression values shown are relative to GAPDH, a housekeeping gene maintained at constant levels in all tissues. Each quantitative real time PCR reaction was performed in duplicate, as represented by paired bars for each sample.

BRIEF DESCRIPTION OF THE TABLES

Table 1 provides the SEQ. ID. NOS. for sequences listed in the Sequence Listing that relate to cluster 192473. Column 1 shows the internally designated identification number (FP ID) for each polynucleotide and/or the corresponding polypeptide sequences. Column 2 shows the SEQ. ID. NOS. of the nucleotide sequences (N1) that encode the open reading frames of the polypeptides (P1) in column 3. Column 3 shows the SEQ ID NOS. of the polypeptide sequences (P1). Column 4 shows the SEQ ID NOS. of the nucleotide sequences (NO) that also encode the corresponding polypeptide in the P1 column and may additionally include non-coding regions such as 5' or 3' UTRs. Column 5 shows the internally designated Source identification (Source ID), which includes a brief description of the source of the sequence, which generally includes the NCBI protein accession number and, if appropriate, the fragment number corresponding to the sequence. Column 6 shows either the amino acid coordinates or amino acid sequence for each P1 SEQ. ID. NO. or indicates that the sequence is full-length ("FL").

Table 2 provides structural information of the polypeptide of SEQ. ID. NO.: 4. Column 1 shows the FP ID. Column 2 shows the Source ID, such as the NCBI accession number. Column 3 shows the cluster number to which the sequence is assigned. Column 4 shows the predicted length of the polypeptides as indicated by the number of amino acid residues present in the polypeptide. Column 5 shows the number of transmembrane (TM) domains predicted for the polypeptide. Column 6 shows the position of the TM domain as predicted by an internally developed algorithm, the numbers indicating the position of the beginning amino acid residue (i.e., 42) and the ending amino acid residue (i.e., 64) spanning the TM domain (TM domains), with the first amino acid residue at the N-terminus of the polypeptide being amino acid residue 1. Column 7 shows the coordinates of the non-TM domains of the sequence.

Table 3 shows the percentage of tissue specimens showing mRNA expression corresponding to the gene in cluster 192473 from among six different types of cancer. Results were obtained by microarray analysis of the data in the Gene Logic (Gaithersburg, Md.) database, created using the Affy U133 (Affymetrix, Santa Clara, Calif.) microarray chip as it relates to expression of the gene in cluster 192473. Column 1 shows the tissue type of the analyzed tissue specimens, whether normal or malignant. Column 2 shows the percentage of tissue specimens for each tissue type that demonstrated mRNA expression corresponding to a gene in cluster 192473. Column 3 shows the total number of tissue specimens analyzed for each tissue type.

Table 4 provides the SEQ. ID. NOS. for sequences listed in the Sequence Listing that relate to the gene in cluster 800228. The columns are as defined in Table 1.

Table 5 provides structural information relating to the polypeptide of SEQ. ID. NO.: 111. The columns are as described for Table 2. Column 4 shows the predicted length of the polypeptide to be 84 amino acid residues. Column 5 shows the presence of one transmembrane (TM) domain predicted for the polypeptide. Column 6 shows the position of the TM domain beginning at amino acid residue 22 and ending at amino acid 44. Column 7 shows the coordinates of the non-TM domains of the sequence.

Table 6 shows the genomic relationship between cluster 800228 and regions of increased chromosomal amplification termed amplicons. Determination of the relationship between a gene locus and an amplicon is based on a statistical calculation that results in a p-value. The gene is then ranked according to its p-value calculated for a particular cancer, as compared to other genes also affected by amplicon activity for that cancer type. This data is shown in the 'log p-value' and 'rank' columns. Cluster 800228 is mapped to a genomic region that falls close to amplicons that were detected in the cancer tissue specimens listed on the table. The fourth column (Distance to the Amplicon) shows this distance measured in nucleotides. The cancers listed in the table are examples of the types of cancers showing amplicon activity within 1000000 nucleotides of the 800228 cluster.

Table 7 provides the SEQ. ID. NOS. for sequences listed in the Sequence Listing that relate to the gene in cluster 800634. The columns are as defined in Table 1.

Table 8 provides structural information relating to the polypeptides of SEQ. ID. NOS.: 185 and 294. Column 1 shows the FP ID. Column 2 shows the Source ID. Column 3 shows the predicted length of the polypeptides. Column 4 shows the Tree-vote score, which is the result of an internally developed decision tree algorithm that predicts whether the polypeptide is a secreted protein or not, with "1" corresponding to a high probability that the polypeptide is secreted and "0" corresponding to a low probability that the polypeptide is secreted. Column 5 shows the position of the signal peptide of each clone as predicted by an internally developed algorithm, indicating the position of the beginning and ending amino acid residues spanning the predicted signal peptides of each clone (Signal Peptide Coords). Column 6 shows the position of the beginning and ending amino acid residues of the polypeptide spanning the predicted mature polypeptides of each clone (Mature Protein Coords), which is amino acid residues 49-112 for CLN00156137.a and 23-101 for CLN00156137.b. Column 7 shows the location of the predicted transmembrane (TM) domain for CLN00156137.b, which is from amino acid residue 44 to 66. Column 8 shows the non-TM domain coordinates.

DESCRIPTION OF THE EMBODIMENTS

The invention provides polynucleotides assigned to clusters 192473, 800228, or 800634, complements thereof, polypeptides encoded thereby, and variants and fragments of the polynucleotides, complements, and polypeptides which are amplified and/or over expressed in certain cancer cells. For example, as compared to respective control tissues, cluster 192473 polynucleotides and polypeptides are more frequently overexpressed by certain populations of breast cancer tumor cells, ovarian cancer tumor cells, colon cancer tumor cells, and melanoma tumor cells. Cluster 800228 polynucleotides and polypeptides are more frequently overexpressed by certain populations of breast cancer tumor cells, ovarian cancer tumor cells, prostate cancer tumor cells, and stomach cancer tumor cells. Cluster 800634 polynucleotides and polypeptides are more frequently overexpressed by certain populations of breast cancer tumor cells, lung cancer tumor cells, and ovarian cancer tumor cells.

The invention further provides modulators, such as antibodies, that may function as either agonists or antagonists and/or that may specifically bind to or interfere with the activity of polynucleotides assigned to clusters 192473, 800228, or 800634, complements thereof, polypeptides encoded thereby, and variants and fragments of the polynucleotides, complements, and polypeptides thereof and thereby treat cancer. For example, polypeptides described herein can be used as immunogens to produce antibody modulators directed against the polypeptide targets. These antibodies can bind to and modulate polypeptides on cell surfaces, such as the extracellular or secreted domain of a transmembrane protein, for example, by inducing antibody-dependent cell cytotoxicity (ADCC) or complement-dependent cytotoxicity (CDC), carry a payload, such as a radioisotope or a cytotoxic molecule, or act as agonist or antagonist antibodies, for example by affecting ligand/receptor interactions, affecting cofactor interactions, interfering with cell signaling, or inducing an apoptotic factor. The antibody modulators of the invention may also be directed against secreted polypeptides that are not anchored to a cell. These antibody modulators may inhibit or block the biological function of a secreted polypeptide. For example, the antibody modulator may block the interaction of a ligand and a receptor by binding to the ligand in such a way that the interaction with the ligand's cognate receptor is blocked. Antibody modulators may also inhibit or block the biological function of polypeptide targets of the invention by preventing the multimerization of polypeptides with other polypeptides, including the formation of homodimers and heterodimers. The modulators of the invention include not only antibodies, but also peptides such as soluble receptors, and extracellular fragments of receptors or transmembrane proteins small molecule drugs, RNAi molecules, ribozymes, and antisense molecules.

The invention provides methods of treating cancers by providing modulators of polynucleotides assigned to clusters 192473, 800228, or 800634, complements thereof, polypeptides encoded thereby, and variants and fragments of the polynucleotides, complements, and polypeptides and administering the modulator to a subject, wherein the modulator inhibits tumor growth and/or progression in the subject. The invention also provides methods of diagnosing cancers using such target molecules and modulators.

DEFINITIONS

The terms used herein have their ordinary meanings, as set forth below, and can be further understood in the context of the specification.

The terms "polynucleotide," "nucleotide," "nucleic acid," "nucleic acid molecule," "nucleic acid sequence," "polynucleotide sequence," and "nucleotide sequence" are used interchangeably herein to refer to polymeric forms of nucleotides of any length. The polynucleotides can contain deoxyribonucleotides, ribonucleotides, and/or their analogs or derivatives.

The terms "amplify" or "amplified" refer to the increased expression of a specified gene by a cell, relative to the expression level that would normally be expected for said cell. "Amplification" of gene expression may occur in response to, for example, an increase in the rate of mRNA transcription, a decrease in the rate of mRNA degradation, a multiplication of the number of copies of a gene, or any combination of these or other cellular events. A typical consequence of "amplified" gene expression is a corresponding increase in the expression of the polypeptide encoded by the said gene.

A "cluster" is an internally devised mechanism for grouping human cDNA clones which map to a single locus on the human chromosome.

"Interfering RNA (RNAi)" refers to the effector molecules of RNA interference, a cellular mechanism of sequence-specific gene silencing that involves inhibition of gene transcription and/or translation. Interfering RNAs (RNAi) are short double-stranded RNA molecules that include, for example, small interfering RNAs (siRNAs) and microRNAs (miRNAs).

The terms "polypeptide," "peptide," and "protein," used interchangeably herein, refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers. The term also includes peptide aptamers.

A "soluble receptor" is a receptor that lacks a membrane anchor domain, such as a transmembrane domain, and may include naturally occurring splice variants of a wild-type transmembrane protein receptor in which the transmembrane domain is spliced out and the extracellular domains or any fragment of the extracellular domain of the transmembrane protein receptor. Soluble receptors can modulate a target protein. They can, for example, compete with wild-type receptors for ligand binding and participate in ligand/receptor interactions, thus modulating the activity of or the number of the receptors and/or the cellular activity downstream from the receptors. This modulation may trigger intracellular responses, for example, signal transduction events which activate cells, signal transduction events which inhibit cells, or events that modulate cellular growth, proliferation, differentiation, and/or death, or induce the production of other factors that, in turn, mediate such activities.

A "biologically active" entity, or an entity having "biological activity," is one or more entities having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction, for example, one that can serve as an epitope or immunogen to stimulate an immune response, such as production of antibodies, or that can participate in stimulating or inhibiting signal transduction by binding to ligands receptors or other proteins, or nucleic acids; or activating enzymes or substrates.

The terms "antibody" and "immunoglobulin" refer to a protein, for example, one generated by the immune system, synthetically, or recombinantly, that is capable of recognizing and binding to a specific antigen; antibodies are commonly known in the art. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab')$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

A "humanized" antibody is a non-human immunoglobulin that contains human immunoglobulin sequences. This term is generally used to refer to an immunoglobulin that has been modified to incorporate a human framework region with the hypervariable regions of a non-human immunoglobulin. The non-human regions of a humanized antibody may extend beyond the hypervariable regions into the variable regions and beyond the variable regions into the framework regions to achieve the desired antigen-binding properties.

A "target cell" is a cell affected, either directly or indirectly, by an administered composition, including those comprising polynucleotides of the invention, polypeptides of the invention, fragments thereof, or modulators thereof.

"Antibody-dependent cell cytotoxicity" (ADCC) is a form of cell mediated cytotoxicity in which an effector cell, such as a lymphocyte, NK cell, granulocyte, neutrophil, eosinophil, basophil, mast cell, or macrophage, mediates the killing of a cell to which an antibody is attached. ADCC can involve humoral and/or cell-dependent mechanisms.

"Complement dependent cytotoxicity" (CDC) is a form of cytotoxicity that can result from activation of the complement pathway. It includes actions mediated through the classical complement pathway.

The term "binds specifically," in the context of antibody binding, refers to high avidity and/or high affinity binding of an antibody to a specific epitope. Hence, an antibody that binds specifically to one epitope (a "first epitope") and not to another (a "second epitope") is a "specific antibody." An antibody specific to a first epitope may cross react with and bind to a second epitope if the two epitopes share homology or other similarity.

The term "binds specifically," in the context of a polynucleotide, refers to hybridization under stringent conditions. Conditions that increase stringency of both DNA/DNA and DNA/RNA hybridization reactions are widely known and published in the art. See, for example, Sambrook, J., et al. (2000) Molecular Cloning, A Laboratory Manual. 3rd ed. Cold Spring Harbor Laboratory Press.

An "isolated," "purified," "substantially isolated," or "substantially purified" molecule (such as a polypeptide, polynucleotide, or antibody) is one that has been manipulated to exist in a higher concentration than in nature. For example, a subject antibody is isolated, purified, substantially isolated, or substantially purified when at least 10%, or 20%, or 40%, or 50%, or 70%, or 90% of non-subject-antibody materials with which it is associated in nature have been removed. As used herein, an "isolated," "purified," "substantially isolated," or "substantially purified" molecule includes recombinant molecules.

A "host cell" is an individual cell or cell culture which can be or has been a recipient of any recombinant vector(s) or isolated polynucleotide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention may be called a "recombinant host cell."

"Patient," "individual," "host," and "subject" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

A "patient sample" is any biological specimen derived from a patient; the term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay.

The term "receptor" refers to a polypeptide that binds to a specific ligand. The ligand is usually an extracellular molecule which, upon binding to the receptor, usually initiates a cellular response such as initiation of a signal transduction pathway.

The term "ligand" refers to a molecule that binds to a specific site on another molecule, usually a receptor.

The term "modulate" refers to the production, either directly or indirectly, of an increase or a decrease, a stimulation, inhibition, interference, or blockage in a measured activity when compared to a suitable control. A "modulator" of a polypeptide or polynucleotide or an "agent" are terms used interchangeably herein to refer to a substance that affects, for example, increases, decreases, stimulates, inhibits, interferes with, or blocks a measured activity of the polypeptide or polynucleotide, when compared to a suitable control.

An "antibody modulator of a polypeptide" is a modulator that recognizes and binds specifically to the polypeptide. Such an antibody may, for example, induce ADCC, CDC, or apoptosis, or may block or otherwise interfere with the activity of a polypeptide.

"Modulating a level of an active subject polypeptide" includes increasing or decreasing, blocking, or interfering with the expression or activity of a subject polypeptide, increasing or decreasing a level of an active polypeptide, and increasing or decreasing the level of mRNA encoding an active subject polypeptide. Modulation can occur directly or indirectly.

"Treatment," as used herein, covers any administration or application of remedies for disease in a mammal, including a human, and includes inhibiting the disease, arresting its development, or relieving the disease, for example, by causing regression, or restoring or repairing a lost, missing, or defective function; or stimulating an inefficient process. For example, "treatment" may include inhibiting breast cancer tumor or melanoma tumor growth.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

A "composition" herein refers to a composition that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses, or powders.

"Disease" refers to any condition, infection, disorder, or syndrome that requires medical intervention or for which medical intervention is desirable. Such medical intervention can include treatment, diagnosis, and/or prevention.

"Tumor" refers to any abnormal cell or tissue growth, whether malignant, pre-malignant, or non-malignant.

A "tumor cell" refers to any cell that is part of a tissue that is abnormally growing. It may be either cancerous (malignant) or benign in nature. Tumor cells that are cancerous may have the ability to metastasize, or spread to neighboring tissues and grow tumors there. Benign tumor cells do not invade neighboring tissues, but may grow to great size and cause other problems that may be impede, for example, breathing, mobility, circulation.

"Biological product of a tumor" or "biological product of a cell or tumor cell" refers to any molecule produced by a cell or cells of a tumor. The "biological product of a tumor" may be secreted or not secreted. It may also be released upon cell lysis or cell death, including programmed cell death (apoptosis). "Biological products of a tumor" may include for example, proteins, small peptides, polynucleotides, hormones, lipids, carbohydrates, or any combination of these or other cellular products.

"Prophylaxis" refers to a therapeutic method intended to prevent the formation of a tumor. Generally, "prophylaxis" involves the inhibition or blockage of the biological activity of a polypeptide or polynucleotide, which in turn results in the death of a potential tumor cell or in the inhibition or blockage of the proliferation of the tumor cell.

"Cancer" is any malignant growth or tumor. Cancer is characterized by the loss of normal control mechanisms for cell growth, including for cell proliferation. Cancer cells may or may not invade the surrounding tissue and, hence, may or may not metastasize to new body sites. Cancer encompasses carcinomas, which are cancers of epithelial cells; carcinomas include breast, colon, lung, ovarian, prostate, stomach, and squamous cell carcinomas, adenocarcinomas, melanomas, and hepatomas. Cancer also encompasses sarcomas, which are tumors of mesenchymal origin; sarcomas include osteogenic sarcomas, gliomas, rhabdomyosarcomas and leiomyosarcomas. Cancers also encompass leukemias, lymphomas, and myelomas. Cancers may involve one or more neoplastic cell type.

The term "progression," includes the meaning of "tumor progression" and comprises the expression of the malignant phenotype by tumor cells as well as the tendency of tumor cells to acquire more aggressive characteristics over time. "Tumor progression" includes all aspects of the meaning of the term metastasis as it is understood by an individual of ordinary skill in the art. "Tumor progression" may involve, for example: 1) the ability of tumor cells to secrete proteases that allow invasion beyond the immediate primary tumor location; 2) the propensity for genomic instability and uncontrolled growth; 3) the activation of protooncogenes and the functional loss of tumor suppressor genes; and/or 4) an increase in the rate of tumor cell proliferation.

The term "proliferation" includes the meaning of "cell proliferation" and refers to an increase in the number of cells as a result of cell growth and cell division.

The Target Molecules of the Invention

As described herein, polynucleotides assigned to clusters 192473, 800228, or 800634, complements thereof, polypeptides encoded thereby, and variants and fragments of these polynucleotides, complements, and polypeptides are overexpressed in certain tumor tissues. Such overexpression can be, for example, driven by an increase in the copy number of the gene encoding the target molecule, i.e., target gene amplification. This particular phenomenon illustrates one manifestation of the concept of "oncogene addiction," in which the product of the amplified gene drives tumorigenesis, and in doing so, alters the cell signaling pathways in such a way as to make a tumor dependent upon target molecule mediated signals for tumor growth and survival (see, for example, Weinstein I B, et al. (2002) Science. 297:63-64).

Overexpression in tumor tissue as a result of gene amplification may correspond 16 a subset of a given tumor type. For example, patients exhibiting an overexpression of the her2/neu gene due to gene amplification comprise approximately 20-25% of all breast cancer patients. Significantly, the group of patients exhibiting her2/neu amplifications are typically more likely to respond to her2/neu directed therapies (e.g., Herceptin/trastuzumab) when compared to patients lacking the her2/neu gene amplification. Thus, detecting molecules that are overexpressed in a specific tumor tissue as a result of a gene amplification event may provide a valuable technique for predicting patient populations that may demonstrate a favorable response to target directed therapy. Such molecules may also provide a potential target for therapeutic action. While the invention is not to be limited by the reason for overexpression, the inventors believe that the overexpression is probably due to a gene amplification event.

The target molecules of the invention were identified following an analysis of genes specifically overexpressed in certain cancer tissues. These genes have been assigned to genomic locations similar to loci, called clusters, which refer to an internally devised mechanism for grouping human cDNA clones which map to a single locus on the human chromosome. The polynucleotides assigned to clusters 192473, 800228, or 800634, complements thereof, polypeptides encoded thereby, and variants and fragments of the polynucleotides, complements, and polypeptides are expressed at higher levels in selected tumor tissues, as compared to their expression in normal tissues, as illustrated, for example, in the Figures and Examples.

The polynucleotides assigned to cluster 192473, complements thereof, polypeptides encoded thereby, and variants and fragments of the polynucleotides, complements, and polypeptides include the National Center for Biotechnology Information (NCBI) clone 27498157. SEQ. ID NOS.:1-105 relate to cluster 192473. Similarly, SEQ. ID. NOS.: 106-178 relate to cluster 800228, which includes an amino acid sequence provided by CN 1351058 A, corresponding to SEQ. ID. NO.: 111. Cluster 800634 provides novel polynucleotides and polypeptides and relates to SEQ. ID. NOS.: 179-366.

Thus, the target molecules of the invention relate to the polynucleotides of SEQ. ID. NOS.:1-3, 104, 106-110, and 177-184 and polypeptides of SEQ. ID. NOS.: 4-103, 105, 111-176, and 185-366, as well as complements of the polynucleotides and fragments and variants of the polynucleotides, their complements, and their encoded polypeptides. The full length molecules of cluster 192473 are provided by SEQ. ID NOS.:1, 4, and 104. The full length molecules of cluster 800228 are provided by SEQ. ID NOS.: 106, 111, and 177. The full length molecules of cluster 800634 are provided by SEQ. ID NOS.: 179, 185, 181, and 294. The target molecules may comprise the genes or gene segments designated in the Figures, Tables, and Sequence Listing, and their gene products, i.e., RNA and polypeptides. They also include variants of those in the Figures, Tables, and Sequence Listing that are present in the normal physiological state, for example, variant alleles such as SNPs and splice variants, as well as variants that are affected in pathological states, such as disease-related mutations or sequences with alterations that lead to pathology, and variants with conservative amino acid changes.

The polynucleotides assigned to and polypeptides encoded by clusters 192473, 800228, or 800634, as well as complements, fragments, or variants thereof, may serve as therapeutic targets and diagnostic markers for certain cancers, because they are overexpressed in or by certain cancer tissues, as compared to normal tissues. For example, the polynucleotides assigned to and polypeptides encoded by cluster 192473, as well as complements, fragments, and variants thereof, are therapeutic targets and diagnostic markers for certain breast cancers, colon cancers, melanomas, and ovarian cancers. The polynucleotides assigned to and polypeptides encoded by cluster 800228, as well as complements, fragments, and variants thereof, are therapeutic targets and diagnostic markers for certain breast cancers, ovarian cancers, prostate cancers, and stomach cancers. The polynucleotides assigned to and polypeptides encoded by cluster 800634, as well as complements, fragments, and variants thereof, are therapeutic targets and diagnostic markers for certain breast cancers, lung cancers, and ovarian Cancers.

Modulators of the Invention

The target molecules of the invention, i.e., the polynucleotides assigned to and polypeptides encoded by clusters 192473, 800228, and 800634, as well as complements, fragments, and variants thereof, may serve to produce and/or identify modulators of the invention. These modulators find use as therapeutic agents in situations where one wishes to modulate an activity of a target polynucleotide or polypeptide for the treatment of, for example, breast cancer, colon cancer, lung cancer, melanoma, ovarian cancer, prostate cancer, or stomach cancer. As noted above, the modulators of the invention may affect, for example, increase, decrease, stimulate, inhibit, interfere with, or black, a measured activity of a target polypeptide or polynucleotide, when compared to a suitable control. Such actions may occur in particular cancers as well as particular populations of cancer patients.

A modulator of a biological activity of a target polypeptide or polynucleotide may cause increases or decreases in the activity or binding of at least about 10%, at least about 15%, at least about 20%, at least about 25%, at least about 50%, at least about 100%, or at least about two-fold, at least about five-fold, or at least about ten-fold or more when compared to a suitable control.

Modulators of the invention include, for example, antibodies, polypeptides and variants, aptamers, whether agonist or antagonist; small molecule drugs, interfering RNAs (RNAi), antisense molecules, and ribozymes.

In some embodiments, modulators of the invention bind to target polypeptides. They may directly modulate the targeted subject polypeptides as a result of their binding. They may also indirectly modulate a biological process by interacting with the targeted subject polypeptides. Modulators of the invention may bind to subject polypeptides in a manner that may or may not interfere with the function of the targeted molecules but may be therapeutically efficacious nonetheless. For example, a modulator may form a complex with a target polypeptide and an effector molecule or effector cell. In some embodiments, modulation may include the recruitment of other molecules that directly effect the modulation. For example, an antibody that modulates the activity of a target polypeptide that is a receptor on a cell surface may bind to the receptor and fix complement, activating the complement cascade and result in lysis of the cell.

The invention also provides a method of identifying a modulator of the biological activity of a polypeptide or polynucleotide of the invention by providing at least one polypeptide chosen from the sequences listed in the Tables, Figures, and Sequence Listing, and active fragments thereof; allowing at least one candidate modulator to contact the polypeptide or polynucleotide; and selecting a modulator that binds the polypeptide or polynucleotide or affects the biological activity of the polypeptide or polynucleotide.

In another embodiment, the invention provides a method of identifying a modulator that inhibits the growth or proliferation of a tumor cell by providing a plurality of candidate modulators, wherein each candidate modulator binds to and/or interferes with the binding or activity of, or otherwise modulates the activity of a polynucleotide assigned to any one of clusters 192473, 800228, or 800634, a complement thereof, a polypeptide encoded thereby, or a fragment or variant of any of these; allowing the plurality of candidate modulators to contact a tumor cell or a biological product of a tumor cell; and selecting a modulator that inhibits growth or proliferation of the tumor cell.

In a further embodiment, the invention provides compositions comprising modulators obtained by these or other methods and a pharmaceutically acceptable carrier. For example, the invention provides modulator compositions comprising a pharmaceutically acceptable carrier and a soluble receptor modulator that competes for ligand binding or cofactor binding to an isolated polypeptide comprising an amino acid sequence chosen from the Tables, Figures, and Sequence Listing. The invention also provides a modulator composition comprising a pharmaceutically acceptable carrier and an extracellular fragment modulator that competes for ligand binding or cofactor binding to an isolated polypeptide comprising an amino acid sequence chosen from the Tables, Figures, and Sequence Listing, and biologically active fragments thereof. The invention also provides modulator compositions comprising a pharmaceutically acceptable carrier and a antibody.

Antibodies

In one embodiment, the modulators of the polynucleotides assigned to any one of clusters 192473, 800228, or 800634, complements thereof, polypeptides encoded thereby, or fragments or variants of any of these, may be antibodies. Thus, in one embodiment, the invention provides isolated antibodies that specifically recognize, bind to, interfere with, and/or otherwise modulate the biological activity of at least one polypeptide comprising an amino acid sequence encoded by a polynucleotide selected from the Figures, Tables, and Sequence Listing, and biologically active fragments thereof. Such sequences may embody epitopes to which such antibodies may bind or interfere. In an embodiment, antibodies of the invention may bind specifically to any polypeptide of the invention, as set forth in the amino acid sequences of SEQ. ID. NOS.: 4-103, 105, 111-176, or 185-366, or biologically active fragments of any of these.

In one embodiment, an antibody modulators of the invention may be directed to a polypeptide comprising part or all of a non-transmembrane domain and/or an extracellular domain, or part or all of another functionally or structurally relevant domain. In one embodiment, the antibody modulators of the invention may block or interfere with the function or activity of secreted target polypeptides in the extracellular compartment, such as binding to receptor sites, thereby modulating the function or activity of the targets. Antibody modulators of the invention may prevent dimerization, and may block counterreceptor interactions.

Such antibodies can also be used in combination with standard chemotherapeutic or radiation regimens to treat cancers. In this case, the antibodies can act to directly or indirectly sensitize the cancer cells to chemotherapy or radiation, allowing for more efficient tumor killing. Alternatively, the antibodies can act in synergy with chemotherapy or radiation treatment, such that lower doses of either may be used, decreasing the overall toxicity to normal cells while maintaining equivalent efficacy in treating the tumor.

The antibodies of the present invention may be administered alone or in combination with other molecules for use as a therapeutic, for example, by linking the antibody to radioactive molecules or other cytotoxic agents. Radioactive antibodies and antibodies comprising a cytotoxic microbial, plant, or chemical compound that are specific to a cancer cell, diseased cell, or other target cell may be able to deliver a sufficient dose of radioactivity or toxin to kill the cell.

As with any modulator of the invention, antibodies of the invention can be used to modulate biological activity of cells, either directly or indirectly. An antibody can modulate the activity of a target cell, with which it has primary interaction, or it can modulate the activity of other cells by exerting secondary effects, i.e., when the primary targets interact or communicate with other cells. An antibody can also modulate the activity of a target cell by primarily interacting with an antigen, which then exerts an effect, whether direct, or indirect, on a target cell. Thus, antibodies of the invention may specifically inhibit the binding of a subject polypeptide to a ligand, inhibit the binding of a subject polypeptide to a substrate, specifically inhibit the binding of a subject polypeptide as a ligand, specifically inhibit the binding of a subject polypeptide as a substrate, specifically inhibit cofactor binding, induce apoptosis, induce ADCC, induce CDC, inhibit protease activity, inhibit adhesion, inhibit migration, inhibit proliferation, inhibit ligand/receptor interaction, and/or inhibit enzyme/substrate interaction.

The antibodies of the invention can be administered to mammals, and the present invention includes such administration, for example, for therapeutic and/or diagnostic purposes in humans. Accordingly, the invention provides a pharmaceutical composition comprising a pharmaceutically acceptable carrier and an antibody of the invention.

Peptides and Modified Peptides

The modulators of the invention also include peptides and modified peptides that may, in one embodiment, inhibit the binding of an isolated polynucleotide assigned to any one of clusters 192473, 800228, or 800634, a complement thereof, a polypeptide encoded thereby, or a fragment or variant of any of these. Such inhibition may serve to inhibit such a target molecule from interacting with its cognate receptor or co-receptor.

In some embodiments, a peptide modulator of the invention exhibits one or more of the following dominant-negative activities: inhibits binding of a target polypeptide to an interacting protein or other molecule, for example proteoglycans of the extracellular matrix; inhibits a target polypeptide from binding to a second polypeptide molecule; inhibits a signal transduction activity of a target polypeptide; inhibits an enzymatic activity of a target polypeptide; or inhibits a DNA binding activity of a target polypeptide.

In some embodiments, a peptide modulator of the invention may be a soluble receptor or a soluble co-receptor. In general, as would be known in the art, a soluble receptor is a receptor that lacks a membrane anchor domain, such as a transmembrane domain. Soluble receptors may include naturally occurring splice variants of a wild-type transmembrane protein receptor in which the transmembrane domain is spliced out having the extracellular domains or any fragment of the extracellular domain. Thus, such modulators are extracellular.

Soluble receptors can modulate a target protein by, for example, competing with wild-type receptors for ligand binding and participating in ligand/receptor interactions. This would serve to modulate the activity of or the number of the receptors and/or the cellular activity downstream from the receptors. This modulation may also serve to trigger intracellular responses, for example, signal transduction events which activate cells, signal transduction events which inhibit cells, or events that modulate cellular growth, proliferation, differentiation, and/or death, or induce the production of other factors that, in turn, mediate such activities.

Also as would be understood in the art, a soluble co-receptor is a co-receptor that lacks a membrane anchor domain, such as a transmembrane domain, and may include naturally occurring splice variants of a wild-type transmembrane protein co-receptor in which the extracellular domain of the co-receptor is expressed without the transmembrane domain as a consequence of the splicing event. Soluble co-receptors may be derived from co-receptors that normally function as secondary cell surface receptors in combination with a ligand and a primary receptor to initiate a biological process. Soluble co-receptors may also be derived from co-receptors that normally function to increase the sensitivity of a primary receptor to its ligand. Such soluble co-receptors can modulate a target protein, as described above.

The peptide modulators of the present invention include peptides of from about five amino acids to about 50. In other embodiments, the peptides range from about five to about 30, or from about ten to about 25 amino acids in length which may, but need not, correspond to the sequence of the naturally-occurring protein. In some embodiments, a peptide has a sequence of from about seven amino acids to about 45, from about nine to about 35, or from about 12 to about 25 amino acids of corresponding naturally-occurring protein.

Interfering RNA (RNAi)

In some embodiments, the modulator is an interfering RNA (RNAi) molecule that inhibits the transcription or translation of an isolated polynucleotide assigned to any one of clusters 192473, 800228, or 800634, a complement thereof, a polypeptide encoded thereby, or a fragment or variant of any of these. RNA interference provides a method of silencing eukaryotic genes. The use of RNAi to reduce a level of a particular mRNA and/or protein is based on the interfering properties of RNA, e.g., double-stranded RNA (dsRNA), derived from the coding regions of a gene. The technique is an efficient high-throughput method for disrupting gene function (O'Neil, N. J., at al. (2001) *Am. J. Pharmacogenomics.* 1:45-53). RNAi can also help identify the biochemical mode of action of a drug and to identify other genes encoding products that can respond or interact with specific compounds.

In an embodiment of the invention, complementary sense and antisense RNAs derived from a substantial portion of a target polynucleotide are synthesized in vitro. The resulting sense and antisense RNAs are annealed in an injection buffer, and the double-stranded RNA injected or otherwise introduced into the subject, for example, in food or by immersion in buffer containing the RNA (Gaudilliere, B., et al. (2002) *J. Biol. Chem.* 277:46,442-46,446.; O'Neil, N. J., et al. (2001) *Am. J. Pharmacogenomics.* 1:45-53.; WO99/32619).

In an embodiment, dsRNA derived from a target polynucleotide is generated in vivo by simultaneously expressing both sense and antisense RNA from appropriately positioned promoters operably linked to sequences in both sense and antisense orientations. The expressed sequences can be derived from the translated portion of a mRNA encoding a polypeptide of the invention, or from the 3' or 5' untranslated regions of such a mRNA.

Antisense Oligonucleotides

In certain embodiments of the invention, the modulator is an antisense molecule that modulates, and generally decreases or down regulates, polypeptide expression in a host. Such an antisense molecule inhibits the transcription or translation of an isolated polynucleotide assigned to any one of clusters 192473, 800228, or 800634, a complement thereof, a polypeptide encoded thereby, or a fragment or variant of any of these.

Antisense modulators of the invention include antisense oligonucleotides (ODN), i.e., synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit target gene expression through various mechanisms, for example, by reducing the amount of mRNA available for translation, through activation of RNaseH, or steric hindrance. One or a combination of antisense molecules can be administered, where a combination can comprise multiple different sequences. See, e.g., Agrawal, S., et al., eds. (1998) *Antisense Research and Application. Handbook of Experimental Pharmaco.*, Vol. 131. Springer-Verlag NY, Inc.; Hartmann, G. and Endres, S., eds. (1999) *Manual of Antisense Methodology (Perspectives in Antisense Science)*. 1$^{st}$ ed. Kluwer Law International.; Phillips, M. I., ed. (1999a) *Antisense Technology, Part A. Methods in Enzymology*, Vol. 313. Academic Press, Inc.; Phillips, M. I., ed. (1999b) *Antisense Technology, Part B. Methods in Enzymology*, Vol. 314. Academic Press, Inc.; Stein, C. A., et al., eds. (1998) *Appl. Antisense Oligonucl. Technol.* Wiley-Liss.).

Antisense molecules can be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides can be chemically synthesized by methods known in the art (Wagner, R. W., et al. (1993) *Science.* 260:1510-1513.; Mitchell, D. A., et al. (2000) *J. Clin. Invest* 106:1065-1069). Antisense oligonucleotides will generally be at least about seven, at least about 12, or at least about 20 nucleotides in length, and not more than about 500, not more than about 50, or not more than about 35 nucleotides in length, where the length is governed by efficiency of inhibition, and specificity, including absence of cross-reactivity, and the like. Short oligonucleotides, of from about seven to about eight bases in length, can be strong and selective inhibitors of gene expression (Wagner, R. W., et al. (1996) *Nat. Biotechnol.* 14:840-844).

A specific region or regions of the endogenous sense strand of target mRNA sequence is selected to be complemented by the antisense sequence. Selection of a specific sequence for the oligonucleotide can use an empirical method, where several candidate sequences are assayed for inhibition of expression of the target gene in an in vitro or animal model. As noted above, a combination of sequences can also be used, where several regions of the mRNA sequence are selected for antisense complementation.

In certain embodiments, the invention provides alternatives to antisense inhibitors. These embodiments involve catalytic nucleic acid compounds, for example, ribozymes, or antisense conjugates, that can be used to inhibit gene expression. Ribozymes can be synthesized in vitro and administered to the patient, or can be encoded in an expression vector, from which the ribozyme is synthesized in the targeted cell (WO 9523225; Beigelman, L., et al. (1995) *Nucleic Acids Res.* 23:4434-4442). Examples of oligonucleotides with catalytic activity are described in WO 9506764. Conjugates of antisense ODN with a metal complex, for example, terpyridyl Cu(II), capable of mediating mRNA hydrolysis have also been described (see Bashkin J K, et al. (1995) Appl Biochem Biotechnol. 54(1-3):43-56).

Aptamers

In yet other embodiments, the modulators of the invention include aptamers. Aptamers of the invention include both nucleotide and peptide aptamers that bind to a polypeptide encoded by a polynucleotide assigned to any one of clusters 192473, 800228, or 800634, or a fragment or variant of any of these. Aptamers of the invention may bind nucleotide cofactors (Latham, J. A., et al. (1994) *Nucl. Acids Res.* 22:2817-2822).

Nucleotide aptamers of the invention include double stranded DNA and single stranded RNA molecules. Peptide aptamers are peptides or small polypeptides that act as dominant inhibitors of protein function. Peptide aptamers specifically bind to target proteins, blocking their functional ability (Kolonin, M. G., et al. (1998) *Proc. Natl. Acad. Sci.* 95:14, 266-14,271). Due to the highly selective nature of peptide aptamers, they can be used not only to target a specific protein, but also to target specific functions of a given protein (for example, a signaling function). Further, peptide aptamers can be expressed in a controlled fashion by use of promoters which regulate expression in a temporal, spatial, or inducible manner. Peptide aptamers act dominantly, therefore, they can be used to analyze proteins for which loss-of-function mutants are not available.

Peptide aptamers that bind with high affinity and specificity to a target protein can be isolated by a variety of techniques known in the art. Peptide aptamers can be isolated from random peptide libraries by yeast two-hybrid screens (Xu, C. W., et al. (1997) *Proc. Natl. Acad. Sci.* 94:12,473-12,478). They can also be isolated from phage libraries (Hoogenboom, H. R., et al. (1998) *Immunotechnology* 4:1-20) or chemically generated peptides/libraries.

Small Molecules

In further embodiments, the modulators of the invention include small molecules such as those commonly used as therapeutic drugs. Small molecule modulators include chemical compounds that bind the polypeptide or polynucleotide and modulate its activity or the activity of the cell that contains it. Small molecule modulators may permeate the cell, and/or may exert their action at the extracellular surface or on non-cellular structures, such as the extracellular matrix.

Therapeutic Applications

Cancer Treatment

As described above, treatment refers to obtaining a desired pharmacologic and/or physiologic effect, covering any treatment of a pathological condition or disorder in a mammal, including a human. The effect may be therapeutic in terms of a partial or complete cure for a disorder and/or adverse affect attributable to the disorder and/or may be prophylactic in terms of completely or partially preventing a disorder or symptom thereof. In an embodiment, the polynucleotides and polypeptides of the invention can be used as targets for treatment modalities for breast, colon, lung, ovarian, prostate, and stomach cancers, and melanoma. Thus, polynucleotides assigned to clusters 192473, 800228, or 800634, complements thereof, polypeptides encoded thereby, and variants and fragments of the polynucleotides, complements, and polypeptides which are amplified and/or over expressed in certain cancer cells can be useful in (1) preventing the disorder from occurring or recurring in a subject who may be predisposed to the disorder but has not yet been diagnosed as having it, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

In an embodiment, the compositions and methods of the invention kill tumor cells. In an embodiment, they inhibit tumor development. Cancer is characterized by the proliferation of abnormal cells that tend to invade the surrounding tissue and metastasize to new body sites. The growth of cancer cells exceeds that of and is uncoordinated with the normal cells and tissues. In an embodiment, the compositions and methods of the invention inhibit the progression of premalignant lesions to malignant tumors.

These cancer treatments may encompass modulating, including increasing and inhibiting, a biological activity of a target protein. In other embodiments, methods of treating cancer may involve modulating a signal transduction activity of a target protein. In further embodiments, the methods of treating cancer may involve methods of modulating the interaction of a target protein with another, interacting protein or other macromolecule (for example a DNA, carbohydrate, or lipid).

Cancers treatable by the molecules of the invention include breast, colon, lung, ovary, prostate and stomach cancers and melanoma. They may have one or more than one neoplastic cell type. Some characteristics that can, in some instances, apply to cancer cells are that they are morphologically different from normal cells, and may appear anaplastic; they have a decreased sensitivity to contact inhibition, and may be less likely than normal cells to stop moving when surrounded by other cells; and they may have lost their dependence on anchorage for cell growth, and may continue to divide in liquid or semisolid surroundings, whereas normal cells must be attached to a solid surface to grow.

In some embodiments, polynucleotides assigned to clusters 192473, 800228, or 800634, complements thereof, polypeptides encoded thereby, and variants and fragments of these polynucleotides, complements, and polypeptides are involved in the control of cell proliferation, and a modulator of the invention inhibits undesirable cell proliferation. In various embodiments, the polynucleotides and polypeptides of the invention may be targets for inhibiting the cellular proliferation of breast, colon, lung, melanoma, ovary, prostate, or stomach tumor cells. Such modulators are useful for treating disorders that involve abnormal cell proliferation as is typical in cancer. How a particular modulator and/or therapeutic regimen of the invention is effective in reducing unwanted cellular proliferation in the context of treating cancer can be determined using standard methods.

In an embodiment, the invention provides a method of treating cancer, e.g., by inhibiting the growth or proliferation of a tumor cell in a subject by providing a modulator of a polynucleotide, complement thereof, polypeptide encoded thereby, or a variant or fragment of the polynucleotide, complement, or polypeptide; and administering the modulator to the subject, wherein the polynucleotide comprises a nucleotide sequence assigned to cluster 192473, 800228, or 800634, and wherein the modulator inhibits tumor growth and/or progression in the subject.

In an embodiment, the invention provides a method of modulating the biological survival of a first human or non-human animal target cell by providing a modulator of the invention and contacting the modulator with the first target cell, wherein the activity of the first target cell, and/or a second target cell, is modulated either directly or indirectly. For example, polynucleotides assigned to clusters 192473, 800228, or 800634, complements thereof, polypeptides encoded thereby, and variants and fragments of these polynucleotides, complements, and polypeptides may modulate a survival signal to a cell which would otherwise die. This modulation may occur either directly or indirectly, for example, through a signaling pathway. When an abnormal number of cells survive, they may contribute to tumor formation. In an embodiment, the invention provides the abrogation of such a survival signal, providing a therapeutic benefit.

Combination Therapies

In an embodiment, the target molecules of the invention can function as a tumor-targeting moiety. Suitable moieties may enhance delivery of a therapeutic molecule to a tumor. For example, compounds that selectively bind to cancer cells compared to normal cells, selectively bind to tumor vasculature, selectively bind to the tumor type undergoing treatment, or enhance penetration into a solid tumor are included in the invention.

In yet another embodiment, the target molecules of the invention can be used as an adjunct to cancer treatment. For example, a polynucleotide, polypeptide, or modulator described above may be added to a standard chemotherapy regimen. It may be combined with one or more of the wide variety of drugs that have been employed in cancer treatment, including, but are not limited to, cisplatin, taxol, etoposide, Novantrone (mitoxantrone), actinomycin D, camptothecin (or water soluble derivatives thereof), methotrexate, mitomycins (for example, mitomycin C), dacarbazine (DTIC), and anti-neoplastic antibiotics such as doxorubicin and daunomycin, or others, described, for example, in De Vita, V. T., Jr., et al., eds. (2001) *Cancer: Principles & Practice of Oncol*. The polynucleotides, polypeptides, and modulators described above can also be combined with radiation therapy.

Such combinations may exert a synergistic effect against cancer cells, such that the dosage of the second modulator may be reduced compared to the standard dosage of the second modulator when administered alone. In another embodiment, the combination may enhance the sensitivity of cancer cells to chemotherapeutic agents. Co-administration may be simultaneous or non-simultaneous administration. Polynucleotides, polypeptides, and modulators described above may be administered along with other therapeutic modulators, during the course of a treatment regimen. In one embodiment, administration of a polynucleotide, polypeptide, or modulator described above and other therapeutic modulators is sequential. An appropriate time course may be selected by the physician, according to such factors as the nature of a patient's illness, and the patient's condition.

Accordingly, in an embodiment, the invention provides a method of treating breast cancer, colon cancer, lung cancer, melanoma, ovarian cancer, prostate cancer, and stomach cancer by providing one or more polynucleotides assigned to clusters 192473, 800228, or 800634, complements thereof, polypeptides encoded thereby, and variants and fragments of the polynucleotides, complements, and polypeptides, and further comprising a second anti-cancer therapeutic. The second agent may comprise, for example, surgery, radiation therapy, a chemotherapeutic agent, or a biologic agent, such as, but not limited to, Herceptin, Avastin, or Rituxan.

Vaccine Therapy

The polynucleotides assigned to clusters 192473, 800228, or 800634, complements thereof, polypeptides encoded thereby, and variants and fragments of the polynucleotides, complements, and polypeptides may be more highly expressed at the surface of cancer cells and are not normally expressed at high levels in healthy individuals. Thus, in one embodiment, polypeptides, such as the extracellular domain of such target proteins, or fragments or variants thereof can be formulated and administered as a vaccine for the prophylaxis and treatment of breast cancer, colon cancer, lung cancer, melanoma, ovarian cancer, prostate cancer, or stomach cancer. Such a vaccine may comprise a biologically active fragment or variant of any of the polypeptides of the invention. The vaccine may be a cancer vaccine, and the polypeptide can concomitantly be a cancer antigen. The vaccine can be administered with or without an adjuvant.

Such a vaccine can be used to treat patients overexpressing the target at the surface of cancer cells, to thereby induce antibody or cell mediated immune responses against the cancer cells, including antibody-dependent cell cytotoxicity (ADCC) or complement dependent cytotoxicity (CDC).

In some embodiments, the invention provides a method for prophylaxis or therapeutic treatment of a subject by providing a vaccine comprising one or more modulators which inhibit the growth or proliferation of a tumor cell and administering the modulator(s) to the subject, wherein the modulator binds to and/or interferes with the binding or activity of, or otherwise modulates the activity of a polynucleotide, a complement thereof, a polypeptide encoded thereby, or a fragment or variant of any of these and wherein the polynucleotide is assigned to cluster 192473, 800228, or 800634.

In the embodiments of the invention, vaccine therapy involves the use of polynucleotides, polypeptides, or modulators of the invention as immunogens for tumor antigens (Machiels, J. P., et al. (2002) Semin. Oncol. 29:494-502; Shinnick, T. M., et al. (1983) Ann. Rev. Microbiol. 37:425-446). For example, peptide-based vaccines of the invention include unmodified polypeptides of the invention, fragments thereof, and MHC class I and class II-restricted peptide (Knutson, K. L., at al. (2001) J. Clin. Invest. 107:477-484), comprising, for example, the disclosed sequences with universal, nonspecific MHC class II-restricted epitopes. Peptide-based vaccines comprising a tumor antigen can be given directly, either alone or in conjunction with other molecules. The vaccines can also be delivered orally by producing the antigens in transgenic plants that can be subsequently ingested (U.S. Pat. No. 6,395,964).

In some embodiments, antibodies themselves can be used as antigens in anti-idiotype vaccines. That is, administering an antibody to a tumor antigen stimulates B cells to make antibodies to that antibody, which in turn recognize the tumor cells.

In yet other embodiments, nucleic acid-based vaccines can deliver tumor antigens as polynucleotide constructs encoding the antigen. Vaccines comprising genetic material, such as DNA or RNA, can be given directly, either alone or in conjunction with other molecules. Administration of a vaccine expressing a molecule of the invention, for example, as plasmid DNA, may lead to persistent expression and release of the therapeutic immunogen over a period of time, helping to control unwanted tumor growth.

In some embodiments, nucleic acid-based vaccines encode antibodies. In such embodiments, the vaccines (for example, DNA vaccines) can include post-transcriptional regulatory elements, such as the post-transcriptional regulatory acting RNA element (WPRE) derived from Woodchuck Hepatitis Virus. These post-transcriptional regulatory elements can be used to target the antibody, or a fusion protein comprising the antibody and a co-stimulatory molecule, to the tumor microenvironment (Pertl, U., et al., (2003). Blood. 101:649-654).

Cytokines can be used to help stimulate immune response. Cytokines act as chemical messengers, stimulating optimal responses from immune cells. An example of a cytokine is granulocyte-macrophage colony-stimulating factor (GM-CSF), which stimulates the proliferation of antigen-presenting cells, thus boosting an organism's response to a cancer vaccine. As with adjuvants, cytokines can be used in conjunction with the antibodies and vaccines disclosed herein. For example, they can be incorporated into the antigen-encoding plasmid or introduced via a separate plasmid, and in some embodiments, a viral vector can be engineered to display cytokines on its surface.

Besides stimulating anti-tumor immune responses by inducing humoral responses, vaccines of the invention can also induce cellular responses, including stimulating T-cells that recognize and kill tumor cells directly. For example, nucleotide-based vaccines of the invention encoding tumor antigens can be used to activate the $CD8^+$ cytotoxic T lymphocyte arm of the immune system.

In some embodiments, the vaccines activate T-cells directly, and in others they enlist antigen-presenting cells to activate T-cells. Killer T-cells are primed, in part, by interacting with antigen-presenting cells, for example, dendritic cells. In some embodiments, plasmids comprising the nucleic acid molecules of the invention enter antigen-presenting cells, which in turn display the encoded tumor-antigens that contribute to killer T-cell activation. Again, the tumor antigens can be delivered as plasmid DNA constructs, either alone or with other molecules.

In further embodiments, RNA can be used. For example, antigen-presenting cells can be transfected or transduced with RNA encoding tumor antigens (Heiser, A., at al. (2002) J. Clin. Invest. 109:409-417; Mitchell, D. A., et al. (2000) J. Clin. Invest. 106:1065-1069). This approach overcomes the limitations of obtaining sufficient quantities of tumor material, extending therapy to patients otherwise excluded from clinical trials. For example, a subject RNA molecule isolated from tumors can be amplified using RT-PCR. In some embodiments, the RNA molecule of the invention is directly isolated from tumors and transfected into antigen-presenting cells or dendritic cells with no intervening cloning steps.

In some embodiments the molecules of the invention are altered such that the peptide antigens are more highly antigenic than in their native state. These embodiments address the need in the art to overcome the poor in vivo immunogenicity of most tumor antigens by enhancing tumor antigen immunogenicity via modification of epitope sequences (Yu, Z. and Restifo, N. P. (2002) J. Clin. Invest. 110:289-294).

Another recognized problem of cancer vaccines is the presence of preexisting neutralizing antibodies. Some embodiments of the present invention overcome this problem by using viral vectors from non-mammalian natural hosts, i.e., avian pox viruses. Alternative embodiments that also circumvent preexisting neutralizing antibodies include genetically engineered influenza viruses, and the use of "naked" plasmid DNA vaccines that contain DNA with no associated protein (Yu, Z. and Restifo, N. P. (2002) J. Clin. Invest. 110:289-294).

Dosages

As described above, an effective amount of a target molecule or a modulator of the invention is administered to the host, at a dosage sufficient to produce a desired result. In some embodiments, the desired result is at least a modification of a given biological activity of a subject polypeptide (in the individual, or in a localized anatomical site in the individual), as compared to a control. In other embodiments, the desired result is at least a modification of the level of an active subject polypeptide (in the individual, or in a localized anatomical site in the individual), as compared to a control. In yet other embodiments, the desired result is at least a modification of the cellular activity of a primary and/or a secondary target cell, as compared to a control.

Typically, the compositions of the instant invention will contain from less than 1% to about 95% of the target molecule or modulator, in some embodiments, about 10% to about 50%. Generally, between about 100 mg and 500 mg of the compositions will be administered to a child and between about 500 mg and 5 grams will be administered to an adult. The frequency of administration will be determined by the care given based on patient responsiveness. Other effective dosages can be readily determined by one of ordinary skill in the art through trials establishing dose response curves.

In order to calculate the amount of a target molecule or a modulator to be administered, those skilled in the art could use readily available information with respect to the amount necessary to have the desired effect. The amount necessary to increase or decrease a level of an active target molecule can be calculated from in vitro experimentation. The amount will, of course, vary depending upon the particular agent used.

Other effective dosages can be readily determined by one of ordinary skill in the art through routine trials establishing dose response curves, for example, the amount of target molecule or modulator necessary to increase or decrease a level of an active target molecule or a level of a cellular activity of a target cell can be calculated from in vitro experimentation. Those of skill will readily appreciate that dose levels can vary as a function of the specific compound, the severity of the symptoms, and the susceptibility of the subject to side effects, and preferred dosages for a given compound are readily determinable by those of skill in the art by a variety of means.

Pharmaceutically Acceptable Carriers

The invention also provides compositions in which compounds of the invention are combined with pharmaceutically acceptable carriers, a wide variety of which are known in the art (Gennaro, A. R. (2003) *Remington: The Sci. and Pract. of Pharm. with Facts and Comparisons: DrugfactsPlus.* 20th ed. Lippincott Williams & Wilkins.; Ansel, H. C., et al., eds. (2004) *Pharmaceutical Dosage Forms and Drug Delivery Systems.* 8th ed. Lippincott Williams & Wilkins.; Kibbe, A. H., ed. (2000) *Handbook of Pharmaceutical Excipients.* $3^{rd}$ ed. Pharmaceutical Press.). Pharmaceutically acceptable carriers are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

In pharmaceutical dosage forms, the compositions of the invention can be administered in the form of their pharmaceutically acceptable salts, or they can also be used alone or in appropriate association, as well as in combination, with other pharmaceutically active compounds. The compositions are formulated in accordance to the mode of potential administration. Modes of administration include oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the compositions of the invention can be formulated into preparations in solid, semi-solid, liquid or gaseous forms, such as tablets, capsules, powders, granules, ointments, solutions, suspensions, suppositories, injections, inhalants, aerosols, sustained release formulations, or oral rinses.

For oral preparations, the agents can be used alone or in combination with appropriate additives, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

For injectable preparations, the agents can be formulated by dissolving, suspending, or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. Other formulations for oral or parenteral delivery can also be used, as conventional in the art.

For aerosol formulations the agents can be formulated into pressurized acceptable propellants such as dichlorodifluoromethane, propane, nitrogen, and the like. Further, the agents may be converted to powder form for administration intranasally or by inhalation, as conventional in the art.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

The agents may also be introduced into tissues or host cells by other routes, such as viral infection, microinjection, or vesicle fusion. For example, expression vectors can be used to introduce nucleic acid compositions into a cell as described above. Further, jet injection can be used for intramuscular administration (Furth, P. A., et al. (1992) *Anal. Biochem.* 205:365-368). The DNA can be coated onto gold microparticles, and delivered intradermally by a particle bombardment device, or "gene gun" as described in the literature (Tang, D. C., et al. (1992) *Nature* 356:152-154), where gold microprojectiles are coated with the DNA, then bombarded into skin cells.

The agents may be provided in unit dosage forms, i.e., physically discrete units suitable as unitary dosages for human and animal subjects, each unit containing a predetermined quantity of compounds of the present invention calculated in an amount sufficient to produce the desired effect in association with a pharmaceutically acceptable diluent, carrier, or vehicle. The specifications for the novel unit dosage forms of the present invention depend on the particular compound employed and the effect to be achieved, and the pharmacodynamics associated with each compound in the host.

Unit dosage forms for oral or rectal administration such as syrups, elixirs, and suspensions can be provided wherein each dosage unit, for example, teaspoonful, tablespoonful, tablet, or suppository, contains a predetermined amount of the composition containing one or more modulators. Similarly, unit dosage forms for injection or intravenous administration can comprise the modulator(s) in a composition as a solution in sterile water, normal saline or another pharmaceutically acceptable carrier.

Detection of Cancer

Detection of cancer cell-specific biomarkers provides an effective cancer screening strategy. Early detection provides not only early diagnosis, but also the ability to screen for polymorphisms and detect post-operative residual tumor cells and occult metastases, an early indicator of tumor recurrence. Early detection of cancer cell-specific biomarkers can thus improve survival in patients before diagnosis, while undergoing treatment, and while in remission. Since the polynucleotides and polypeptides of the invention are not normally expressed at high levels by skin and breast tissue of healthy individuals, but are highly expressed in breast, colon, lung, ovarian, prostate, and stomach cancer, and melanoma tumor tissue, their elevated presence can be used as a diagnostic or prognostic marker for melanoma and breast cancer. Thus, antibodies raised against the polynucleotides assigned to clusters 192473, 800228, or 800634, complements thereof, polypeptides encoded thereby, and variants and fragments of the polynucleotides, complements, and polypeptides may be used to diagnose their overexpression. Alternatively, the overexpression of these polynucleotides and polypeptides may lead to the presence or increased presence of antibodies against such targets, such that molecules of the invention may be used to diagnose their presence.

Thus, the invention also provides methods for diagnosing cancer disease states based on the detected presence and/or level of target polynucleotides, polypeptides, or antibodies in a biological sample, and/or the detected presence and/or level of biological activity of the polynucleotide or polypeptide. These detection methods can be provided as part of a kit. Thus, the invention further provides kits for detecting the presence and/or a level of a polynucleotide, polypeptide, or antibody of interest in a biological sample, or for detecting the presence and/or a level of biological activity of a polynucleotide or polypeptide in a biological sample.

Detection may be accomplished by a range of assay techniques, including but not limited to ELISA, Western blot, immunofluorescence, or immunohistochemistry. In some embodiments, the assay is a binding assay that detects binding of a polypeptide with an antibody specific for the polypeptide; one member of the binding pair is immobilized while the other is detectably labeled. For example, the antibody can be directly labeled or detected with a labeled secondary antibody. Thus, suitable labels include direct labels, which label the antibody to the protein of interest, and indirect labels, which label an antibody that recognizes the antibody to the protein of interest.

These labels include radioisotopes, including, but not limited to $^{64}$Cu, $^{67}$Cu, $^{90}$Y, $^{99m}$Tc, $^{111}$In, 124I, $^{125}$I, $^{131}$I, $^{137}$CS, $^{186}$Re, $^{211}$At, $^{212}$Bi, $^{213}$Bi, $^{223}$Ra, $^{241}$Am, and $^{244}$Cm; enzymes having detectable products (for example, luciferase, peroxidase, alkaline phosphatase, β-galactosidase, and the like); fluorescers and fluorescent labels, for example, fluorescein and rhodamine; fluorescence emitting metals, for example, $^{152}$Eu, or others of the lanthanide series, attached to the antibody through metal chelating groups such as EDTA; chemiluminescent compounds, for example, luminol, isoluminol, or acridinium salts; and bioluminescent compounds, for example, luciferin, or aequorin (green fluorescent protein), specific binding molecules, for example, magnetic particles, microspheres, nanospheres, luminescent quantum dot nanocrystals, and the like.

Alternatively, specific-binding pairs may be used, involving, for example, a second stage antibody or reagent that is detectably labeled and that can amplify the signal. For example, a primary antibody can be conjugated to biotin, and horseradish peroxidase-conjugated strepavidin added as a second stage reagent. Digoxin and antidigoxin provide another such pair. In other embodiments, the secondary antibody can be conjugated to an enzyme such as peroxidase in combination with a substrate that undergoes a color change in the presence of the peroxidase. The absence or presence of antibody binding can be determined by various methods, including flow cytometry of dissociated cells, microscopy, radiography, or scintillation counting. Such reagents and their methods of use are well known in the art.

Antibodies of the invention can be provided in the form of arrays, i.e., collections of plural biological molecules having locatable addresses that may be separately detectable. Generally, a microarray encompasses use of submicrogram quantities of biological molecules. The antibodies may be affixed to a substrate or may be in solution or suspension. The substrate can be porous or solid, planar or non-planar, unitary or distributed, such as a glass slide, a 96 well plate, with or without the use of microbeads or nanobeads. Antibody microarrays of the invention include arrays of antibodies obtained by purification, as fusion proteins, and or recombinantly, and can be used for specific binding studies (Zhu, H. and Snyder, M. (2001) *Curr. Drug Disc.* 6:31-34; Houseman, B. T. and Mrksich, M. (2002) *Chem. Biol.* 9:443-54; Schaeferling, M. et al. (2002) *Electrophoresis.* 23:3097-105; Weng, S. et al. (2002) *Proteomics.* 2:48-57; Winssinger, N. et al. (2002) *Proc. Natl. Acad. Sci.* 99:11139-44; and MacBeath, G. and Schreiber, S. L. (2000) *Science.* 289:1673).

In further embodiments, the invention provides kits based on such polypeptide and/or antibody reagents labeled as noted above. In an embodiment, the kit is a diagnostic kit for use in screening serum containing antibodies specific against polypeptides of the invention. Such a kit may include a control antibody that does not react with the polypeptide of interest. Such a kit may include a substantially isolated polypeptide antigen comprising an epitope which is specifically immunoreactive with at least one anti-polypeptide antigen antibody. In an embodiment, the kit may include a recombinantly produced or chemically synthesized polypeptide antigen. The polypeptide antigen of the kit may also be attached to a solid support.

In a further embodiment, the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In another embodiment, the invention provides a diagnostic kit for use in screening serum containing antigens of the polypeptides of the invention. Such a diagnostic kit would include a substantially isolated antibody specifically immunoreactive with polypeptide or polynucleotide antigens, and means for detecting the binding of the antibody to the polynucleotide or polypeptide antigen. In an embodiment, the antibody is attached to a solid support. In an embodiment, the antibody is a monoclonal antibody. The detecting means of the kit may include a second, labeled monoclonal antibody, as noted above. Alternatively, or in addition, the detecting means may include a labeled, competing antigen.

In one diagnostic configuration of the invention, test serum is reacted with a solid phase reagent having a surface-bound antigen obtained by the methods of the present invention. After the reaction, unbound serum components are removed by washing. The reagent is then reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate.

The solid surface reagent may be prepared by known techniques for attaching protein material to solid support material, such as polymeric beads, dip sticks, 96-well plates, and/or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with a biotinylated antigen.

All of the immunogenic methods of the invention can be used alone or in combination with other conventional or unconventional therapies. For example, immunogenic molecules can be combined with other molecules that have a variety of antiproliferative effects, or with additional substances that help stimulate the immune response, for example, adjuvants or cytokines.

Detection of Target Molecules of the Invention by FISH

An especially sensitive method for detecting gene amplification events associated with specific types of cancer is fluorescence in-situ hybridization ("FISH"). FISH is one example of a nucleic acid probe-based assay in which the probes of the invention may be used. This analysis generally entails preparing a cytological sample, labeling probes, denaturing target chromosomes and the probe, hybridizing the probe to the target sequence, and detecting a signal. Typically, the hybridization reaction fluorescently stains the target sequences so that their location, size, or number can be determined using fluorescence microscopy, flow cytometry or other suitable instrumentation. Single and multicolor FISH, using probes, have been applied to many different clinical applications, including the use of FISH analysis to detect the aggressive form of breast cancer normally associated with HER-2/neu gene amplification (Press M F, et al., (1997) 15:2894-904). Accordingly, the invention provides a method of providing a diagnosis or prognosis for a patient known to or suspected of having cancer by determining the presence, absence, and/or level of a polynucleotide assigned to cluster 192473, 800228, or 800634, using FISH analysis.

Polypeptide Expression

The peptides of the invention, including peptide modulators, may include naturally-occurring and non-naturally occurring amino acids. Peptides can comprise D-amino acids, a combination of D- and L-amino acids, and various "designer" or "synthetic" amino acids (for example, β-methyl amino acids, Cα-methyl amino acids, and Nα-methyl amino acids, etc.) to convey special properties. Additionally, peptides can be cyclic. Peptides can include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics can be incorporated into a peptide to induce or favor specific secondary structures, Including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analogs; amide bond isostere; or tetrazol, and the like.

Peptides of the invention can be a depsipeptide, which can be linear or cyclic (Kuisle, O., et al., (1999) *J. Org. Chem.* 64:8063-75). Linear depsipeptides can comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. Cyclic depsipeptides contain at least one ring formed only through peptide or ester links, derived from hydroxy carboxylic acids.

Peptides of the invention can be cyclic or bicyclic. For example, the C-terminal carboxyl group or a C-terminal ester can be induced to cyclize by internal displacement of the (—OH) or the ester (—OR) of the carboxyl group or ester respectively with the N-terminal amino group to form a cyclic peptide. For example, after synthesis and cleavage to yield the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art.

A desamino or descarboxy residue can be incorporated at the terminal ends of the peptide, so that there is no terminal amino or carboxyl group, to decrease susceptibility to proteases or to restrict conformation. C-terminal functional groups include amide, amide lower alkyl, amide di (lower alkyl), lower alkoxy, hydroxy, and carboxy, and the lower ester derivatives thereof, and the pharmaceutically acceptable salts of any of these. In general, pharmaceutical salts include the acid addition salts (formed with the free amino groups of the polypeptide) and which are formed with inorganic acids such as, for example, hydrochloric or phosphoric acids, or such organic acids as acetic, mandelic, oxalic, and tartaric. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, and histidine.

In addition to the foregoing N-terminal and C-terminal modifications, peptides or peptidomimetics of the invention can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran, and dextran derivatives. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zalipsky (Zalipsky, S. (1995) *Bioconjug. Chem.* 6:150-65); Monfardini (Monfardini, C., et al. (1995) *Bioconjug. Chem.* 6:62-9); U.S. Pat. Nos. 4,640,835; 4,496,689; 4,301,144; 4,670,417; 4,791,192; 4,179,337, or WO 95/34326.

The target polynucleotides of the invention may find use in the preparation of all or a portion of the polypeptides of the invention. As would be recognized in the art, the polypeptides described herein can be expressed from the polynucleotides using methods known in the art. The following is a non-limiting overview of such known methods.

Amplification of polynucleotide targets of the invention can be accomplished by any appropriate molecular biology technique available, including the polymerase chain reaction. Cell-based methods and cell-free methods are all suitable for producing polypeptides of the invention. The use of the polymerase chain reaction has been described in Saiki, R. K. at al. (1985) *Science.* 230:1350-1354 and current techniques have been reviewed in Sambrook & Russell (2000) *Molecular Cloning: A Laboratory Manual (Third Edition)* CSHL Press; Dieffenbach and Dveksler, (1995) *PCR Primer: A Laboratory Manual* (2003) CSHL Press. Cell-based methods generally involve introducing a nucleic acid construct into a host cell in vitro and culturing the host cell under conditions suitable for expression, then harvesting the polypeptide, either from the culture medium or from the host cell, (for example, by disrupting the host cell), or both. Host cells are described in more detail below.

The polynucleotides of the Invention can also be provided as part of a vector (e.g., a polynucleotide construct), a wide variety of which are known in the art. Vectors include, but are not limited to, plasmids; cosmids; viral vectors; human, yeast, bacterial, P1-derived artificial chromosomes (HAC's, YAC's, BAC's, PAC's, etc.), and mini-chromosomes. Vectors are amply described in numerous publications well known to those in the art (Ausubel, F. M. et al. (1995) *Current protocols in molecular biology*. John Wiley, New York, N.Y.; Jones, P. of al. (1998a) *Vectors: Cloning Applications: Essential Techniques*, John Wiley & Son, Ltd.; Jones, P. et al. (1998b) *Vectors: Expression Systems: Essential Techniques*, John Wiley & Son, Ltd.). Vectors can provide for nucleic acid expression, for nucleic acid propagation, or both.

A recombinant vector or construct that includes a polynucleotide of the invention is useful for propagating a nucleic acid in a host cell. Vectors can transfer nucleic acid between host cells derived from disparate organisms; these are known in the art as "shuttle vectors." Vectors can also insert a subject nucleic acid into a host cell's chromosome; these are known in the art as "insertion vectors." Vectors can express either sense or antisense RNA transcripts of the invention in vitro (e.g., in a cell-free system or within an in vitro cultured host cell); these are known in the art as "expression vectors." Expression vectors can also produce a subject polypeptide encoded by a subject nucleic acid.

Such expression vectors provide a transcriptional and translational initiation region, which may be inducible or constitutive, where the coding region is operably linked under the transcriptional control of the transcriptional initiation region, and a transcriptional and translational termination region. These transcriptional and translational control regions can be native to a gene encoding the subject peptides, or can be derived from exogenous sources.

Vectors typically include at least one origin of replication, at least one site for insertion of heterologous nucleic acid (e.g., in the form of a polylinker with multiple, tightly clustered, single cutting restriction endonuclease recognition sites), and at least one selectable marker, although some integrative vectors will lack an origin that is functional in the host to be chromosomally modified, and some vectors will lack selectable markers.

Prior to vector insertion, the DNA of interest will be obtained substantially free of other nucleic acid sequences, and will be at least about 50%, or at least about 90% pure. The DNA can be "recombinant," and flanked by one or more nucleotides with which it is not normally associated on a naturally occurring chromosome.

Expression vectors generally have convenient restriction sites located near the promoter sequence to provide for the insertion of nucleic acid sequences encoding heterologous proteins. A selectable marker operative in the expression host can be present. Expression vectors can be used for the production of fusion proteins, where the exogenous fusion peptide provides additional functionality, i.e. increased protein synthesis, stability, reactivity with defined antisera, or an enzyme marker, e.g. -galactosidase.

Expression vectors can be prepared comprising a transcription initiation region, the gene or fragment thereof, and a transcriptional termination region. Of particular interest is the use of DNA sequences that allow for the expression of functional epitopes or domains, at least about 8 amino acids in length, at least about 15 amino acids in length, or at least about 25 amino acids in length, or any of the above-described fragments, up to and including the complete open reading frame of the gene. After introduction of these DNA sequences, the cells containing the construct can be selected by means of a selectable marker, and the selected cells expanded and used as expression-competent host cells.

Introduction of the vector construct into a host cell can be effected by calcium phosphate transfection, DEAE-dextran mediated transfection, cationic lipid-mediated transfection, electroporation, transduction, infection, or other methods. Such methods are described in many standard laboratory manuals, such as Sambrook, J., et al. (2001) *Molecular Cloning, A Laboratory Manual.* $3^{rd}$ ed. Cold Spring Harbor Laboratory Press.

Host cells can comprise prokaryotes or eukaryotes that express proteins and polypeptides in accordance with conventional methods, the method depending on the purpose for expression. For large scale production of the protein, a unicellular organism, such as *E. coli, B. subtilis, S cerevisiae*, insect cells in combination with baculovirus vectors, or cells of a higher organism such as vertebrates, particularly mammals, e.g. COS 7 cells, can be used as the expression host cells. In some situations, it is desirable to express eukaryotic genes in eukaryotic cells, where the encoded protein will benefit from native folding and post-translational modifications.

Specific expression systems of interest include plants, bacteria, yeast, insect cells and mammalian cell-derived expression systems. Representative systems from each of these categories is are provided below.

Expression systems In plants include cereal plants, tobacco, tomato as well as those described in U.S. Pat. No. 6,096,546 and U.S. Pat. No. 6,127,145.

Expression systems in bacteria include those described by Chang et al., (1978) *Nature.* 275:615; Goeddel, D. V., et al. (1979) *Nature.* 281:544-548; Goeddel, D. V., et al., (1980) *Nucleic Acids Res.* 8:4057-4074; EP 0 036,776; U.S. Pat. No. 4,551,433; de Boer, H. A., et al. (1993) *Proc. Natl. Acad. Sci. U.S.A.* 80:21-25; and Siebenlist, U., et al., (1980) *Cell.* 20:269-281.

Expression systems in yeast include those described by Hinnen, A., et al. (1978) *Proc. Natl. Acad. Sci. U.S.A.* 75:1929-1933; Ito, H., et al., (1978) *J. Bacteria* 153:163-168; Kurtz, M. B., et al. (1986) *Mol. Cell. Biol.* 6:142-149.; Kurtz, M. B., et al. (1986) *Mol. Cell. Biol.* 6:142-149.; M. A. Gleeson and P. E. Sudbery, *The Methylotrophic Yeasts*, Yeast, vol. 4: 1-15 (1988); Roggenkamp, R., et al. (1984) *Mol. Gen. Genet.* 194:489-493; van den Berg, J. A., et al., (1990) *Bio/Technology* 8:135-139.; Kunze, G. et al., (1985) *J. Basic Microbiol.* 25:141-144.; Cregg, J. M., et al., (1985) *Mol. Cell. Biol.*

5:3376-3385.; U.S. Pat. Nos. 4,837,148 and 4,929,555; Beach, D., et al. (1982) *Nature* 300:706-709; Davidow, L. S., et al. (1987) *Curr. Genet.* 11:377-383; Gaillardin and Ribet. (1987) *Curr. Genet.* 11:369-375; Ballance, D. J., et al., (1983) *Biochem. Biophys. Res. Commun.* 112: 284-289; Tilburn, J., et al. (1983) *Gene* 26: 205-221.; Yelton, M. M., Hamer, J. E., Timberlake, W. E. (1984) *Proc. Natl. Acad. Sci.* (USA) 81:1470-1474; Kelly, J. M., Hynes, M. J. (1985) *EMBO J.* 4:475-479.; EP 0 244,234; WO 91/00357; and U.S. Pat. No. 6,080,559.

Expression systems for heterologous genes in insects includes those described in U.S. Pat. No. 4,745,051; Friesen et al., (1986) *The Regulation of Baculovirus Gene Expression, in: The Molecular Biology Of Baculoviruses* (W. Doerfler, ed.); EP 0 127,839; EP 0 155,476; Vlak, J. M. et al., (1988) *J. Gen. Viral.* 69:765-776.; Miller et al. (1988) *Ann. Rev. Microbiol.* 42:177 Carbonell, L. F., et al. (1988) *Gene* 73:409-18.; Maeda et al. (1985) *Nature* 315:592-594; Lebacq-Verheyden et al. (1988) *Mol. Cell. Biol.* 8:3129; Smith et al. (1985) *Proc. Natl. Acad. Sci.* (*USA*) 82:8844; Miyajima et al., (1987) *Gene* 58:273.; and Martin et al. (1988) *DNA* 7:99. Numerous baculoviral strains and variants and corresponding permissive insect host cells are described in Luckow et al. (1988) *Bio/Technology* 6:47-55, Miller et al., (1986) *Generic Engineering* 8:277-279, and Maeda et al., 1985.

Mammalian expression systems include those described in Dijkema, R., et al. (1985) *EMBO J.* 4:761-767; Gorman, C. M., et al. (1982) *Proc. Natl. Acad. Sci.* (*USA*) 79:6777-6781; Boshart, M., et al. (1985) *Cell* 41:521-30; and U.S. Pat. No. 4,399,216. Additional features of mammalian expression are facilitated as described in Ham and Wallace, (1979) *Meth. Enz.* 58:44; Barnes, D. and Sato, G. (1980) *Anal. Biochem.* 102:255-70; U.S. Pat. Nos. 4,767,704, 4,657,866, 4,927,762, 4,560,655, WO 90/103430, WO 87/00195, and U.S. RE 30,985.

When any of the above-referenced host cells, or other appropriate host cells or organisms, are used to replicate and/or express the polynucleotides of the invention, the resulting replicated nucleic acid, RNA, expressed protein or polypeptide, is within the scope of the invention as a product of the host cell or organism. The product can be recovered by any appropriate means known in the art.

Once the gene corresponding to a selected polynucleotide is identified, its expression can be regulated in the gene's native cell types. For example, an endogenous gene of a cell can be regulated by an exogenous regulatory sequence inserted into the genome of the cell at a location that will enhance gene expression. The regulatory sequence can be designed to integrate into the genome via homologous recombination, as disclosed in U.S. Pat. Nos. 5,641,670 and 5,733,761, the disclosures of which are herein incorporated by reference. Alternatively, it can be designed to integrate into the genome via non-homologous recombination, as described in WO 99/15650, the disclosure of which is also herein incorporated by reference. Also encompassed in the invention is the production of proteins without manipulating the encoding nucleic acid itself, but rather by integrating a regulatory sequence into the genome of a cell that already includes a gene that encodes the protein of interest; this production method is described in the above-incorporated patent documents.

The target polypeptides can be recovered and purified from recombinant cell cultures by well-known methods, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography (HPLC) can be employed for purification. Target polypeptides include products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Typically, a heterologous polypeptide, whether modified or unmodified, may be expressed as described above, or as a fusion protein, and may include not only secretion signals, but also a secretory leader sequence. A secretory leader sequence of the invention may direct certain proteins to the endoplasmic reticulum (ER). The ER separates the membrane-bound proteins from other proteins. Once localized to the ER, proteins can be further directed to the Golgi apparatus for distribution to vesicles; including secretory vesicles; the plasma membrane, lysosomes, and other organelles.

Proteins targeted to the ER by a secretory leader sequence can be released into the extracellular space as a secreted protein. For example, vesicles containing secreted proteins can fuse with the cell membrane and release their contents into the extracellular space in a process called exocytosis. Exocytosis can occur constitutively or in response to a triggering signal. In the latter case, the proteins may be stored in secretory vesicles (or secretory granules) until exocytosis is triggered. Similarly, proteins residing on the cell membrane can also be secreted into the extracellular space by proteolytic cleavage of a linker holding the protein to the membrane.

Additionally, peptide moieties and/or purification tags may be added to the polypeptide to facilitate purification. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin.

Protein expression systems known in the art can produce fusion proteins that incorporate the polypeptides of the invention. Target protein fusions can facilitate production, secretion, and/or purification. They can confer a longer half-life when administered to an animal. Fusion partners suitable for use in the invention include, for example, polyethylene glycol (PEG), fetuin, human serum albumin, immunoglobulin $F_c$, and/or one or more of their fragments. Such modified polypeptides can show, for example, enhanced activity or increased stability. In addition, they may be purified in higher yields and show better solubility than the corresponding natural polypeptide, at least under certain purification and storage conditions.

In yet further embodiments, the attributes of the protein may be changed by modifying amino acids. For example, replacing amino acids can also change the selectivity of the binding of a ligand to cell surface receptors. For example, Ostade et al. (1993) *Nature*. 361:266-268 describes mutations resulting in selective binding of TNF-α to only one of the two known types of TNF receptors. Sites that are critical for ligand-receptor binding can also be determined by structural analysis such as crystallization, nuclear magnetic resonance, or photoaffinity labeling, for example, Smith et al., (1992) *J. Mol. Biol.*, 224:899-904 and de Vos et al. (1992) *Science*. 255:306-312.

Process for the Selection and Production of Antibodies

Antibody Epitopes

The polynucleotides and polypeptides of the invention may serve to select and/or produce antibodies of the invention. In one embodiment, an eliciting sequence that can induce or select an antibody can be any polynucleotide or amino acid sequence of approximately eighteen or more contiguous nucleotides or approximately six or more amino acids. A variety of comparing means can be used to accomplish comparison of sequence information from a sample (for example, to analyze sequences, motifs, or relative expression levels) with the data storage means. A skilled artisan can readily recognize that any one of the publicly available homology search programs, for example, BLAST, can be used as the search means to accomplish comparison of such eliciting sequences and motifs. An eliciting sequence refers to an amino acid sequence that can be used as an immunogen for injection into animals for production of antibodies or for screening against a phage display or antibody library for identification of binding partners.

In some embodiments, the invention provides eliciting structural motifs and eliciting functional motifs, i.e., any rationally selected sequences or combination of sequences in which the sequence(s) are selected based on a three-dimensional configuration formed upon the folding of the motif, or on consensus sequences of regulatory or active sites. There are a variety of such motifs known in the art. Protein motifs include, but are not limited to, enzyme active sites and signal sequences. Nucleic acid motifs include, but are not limited to, hairpin structures, promoter sequences, and other expression elements, such as binding sites for transcription factors.

Antibodies of the invention bind specifically to their eliciting sequences. Specific binding, in the context of antibody binding, refers to high avidity and/or high affinity binding of an antibody to a specific polypeptide, or more accurately, to an epitope of a specific polypeptide. Antibody binding to such an epitope on a polypeptide can be stronger than binding of the same antibody to any other epitopes, particularly other epitopes that can be present in molecules in association with, or in the same sample as the polypeptide of interest. For example, when an antibody binds more strongly to one epitope than to another, adjusting the binding conditions can result in antibody binding almost exclusively to the specific epitope and not to any other epitopes on the same polypeptide, and not to any other polypeptide, which does not comprise the epitope. Antibodies that bind specifically to a subject polypeptide may be capable of binding other polypeptides at a weak, yet detectable, level (for example, 10% or less of the binding shown to the polypeptide of interest). Such weak binding, or background binding, is readily discernible from the specific antibody binding to a subject polypeptide, for example, by use of appropriate controls. In general, antibodies of the invention bind to a specific polypeptide with a binding affinity of $10^7$ $M^{-1}$ or greater (for example, $10^8$ $M^{-1}$, $10^8$ $M^{-1}$, $10^{10}$ $M^{-1}$, $10^{11}$ $M^{-1}$, etc.).

In one embodiment, the invention provides antibodies that can distinguish variant sequences from one another. These antibodies can distinguish polypeptides that differ by no more than one amino acid (U.S. Pat. No. 6,656,467). They have high affinity constants, i.e., in the range of approximately $10^{10}$ $M^{-1}$, and are produced, for example, by genetically engineering appropriate antibody gene sequences, according to the method described in U.S. Pat. No. 6,656,467.

In other embodiments, antibodies of the invention can be provided as matrices, i.e., as geometric networks of antibody molecules and their antigens, as found in immunoprecipitation and flocculation reactions. An antibody matrix can exist in solution or on a solid phase support.

In yet further embodiments, antibodies of the invention can be provided as a library of antibodies or fragments thereof, wherein at least one antibody or fragment thereof specifically binds to at least a portion of a polypeptide comprising an amino acid sequence or fragment thereof described in the Figures, and Sequence Listing, and/or wherein at least one antibody or fragment thereof interferes with at least one activity of the polypeptide or fragment thereof. In certain embodiments, the antibody library comprises at least one antibody or fragment thereof that specifically inhibits the binding of a NCBI 27498157 polypeptide to its ligand or other interaction partner, or that specifically inhibits binding of a NCBI 27498157 polypeptide as a ligand to a receptor for NCBI 27498157 polypeptides. In certain embodiments, the antibody library comprises combinatorial complementarity determining regions, heavy chains, and light chains. The present invention also features corresponding polynucleotide libraries comprising at least one polynucleotide sequence that encodes an antibody or antibody fragment of the invention. In specific embodiments, the library is provided on a nucleic acid array or in computer-readable format.

Methods of Making Antibodies

The invention also provides methods of making antibodies by introducing an antigen selected from an isolated nucleic acid molecule comprising at least one polynucleotide sequence selected from the Figures, Tables and Sequence Listing; sequences that hybridize to these sequences under high stringency conditions; sequences having at least 80% sequence identity to these sequences; complements of any of these sequences; or biologically active fragments of any of the above-listed sequences. The antigen may also be selected from an isolated polypeptide comprising an amino acid sequence, wherein the amino acid sequence is selected from the Figures, Tables and Sequence Listing, or a biologically active fragment thereof, or is encoded by a polynucleotide sequence selected from the Figures, Tables and Sequence Listing, or a biologically active fragment thereof. Such antigens may be introduced into an animal in an amount sufficient such that antibodies specific to the antigen can be generated and/or recovered.

Immunogens within the invention may comprise a nucleic acid, a complete protein, or fragments and derivatives thereof, or proteins expressed on cell surfaces. Protein domains, for example, extracellular, cytoplasmic, or luminal domains can be used as immunogens. Immunogens can comprise all or a part of a subject polypeptide, where the amino acids contain post-translational modifications, such as glycosylation, found on the native target protein. Immunogens comprising protein extracellular domains are produced in a variety of ways known in the art, for example, expression of cloned genes using conventional recombinant methods, or isolation from tumor cell culture supernatants, etc. The immunogen can also be expressed in vivo from a polynucleotide encoding the immunogenic peptide introduced into the host animal.

The production and use of antibodies is well-known in the art (Harlow, E. and Lane, D., eds. (1988) *Antibodies: A Laboratory Manual*. Cold Spring Harbor Laboratory.; Harlow, E., et al., eds. (1998) *Using Antibodies: A Laboratory Manual: Portable Protocol NO. 1.* Cold Spring Harbor Laboratory.; Howard, G. C. and Bethell, D. R. (2000) *Basic Methods in Antibody Production and Characterization.* CRC Press.). The following is a non limiting overview of such methods.

Polyclonal antibodies of the invention may be prepared by conventional techniques. These include immunizing the host animal in vivo with immunogen in substantially pure form. To increase the immune response of the host animal, the immunogen can be combined with an adjuvant; suitable adjuvants include alum, dextran, sulfate, large polymeric anions, and oil and water emulsions, for example, Freund's adjuvant (complete or incomplete). The immunogen can also be conjugated to synthetic carrier proteins or synthetic antigens. The immunogen is administered to the host, usually intradermally, with an initial dosage followed by one or more, usually at least two, additional booster dosages. Following immunization, blood from the host is collected, followed by separation of the serum from blood cells. The immunoglobulin present in the resultant antiserum can be further fractionated using known methods, such as ammonium salt fractionation, or DEAE chromatography and the like.

Monoclonal antibodies of the invention are also produced by conventional techniques, such as fusing an antibody-producing plasma cell with an immortal cell to produce hybridomas. Suitable animals will be used, for example, to raise antibodies against a mouse polypeptide of the invention; the host animal will generally be a hamster, guinea pig, goat, chicken, or rabbit, or the like. Generally, the spleen and/or lymph nodes of an immunized host animal provide the source of plasma cells, which are immortalized by fusion with myeloma cells to produce hybridoma cells. Culture supernatants from individual hybridomas are screened using standard techniques to identify clones producing antibodies with the desired specificity. The antibody can be purified from the hybridoma cell supernatants or from ascites fluid present in the host by conventional techniques, for example, affinity chromatography using antigen, for example, the subject protein, bound to an insoluble support, for example, protein A Sepharose®, etc.

The antibody can be produced as a single chain, instead of the normal multimeric structure of the immunoglobulin molecule. Single chain antibodies have been previously described (Jost, C. R., et al. (1994) *J. Biol. Chem.* 269:26, 267-26,273). DNA sequences encoding parts of the immunoglobulin, for example, the variable region of the heavy chain and the variable region of the light chain are ligated to a spacer, such as one encoding at least about four small neutral amino acids, i.e., glycine or serine. The protein encoded by this fusion allows the assembly of a functional variable region that retains the specificity and affinity of the original antibody.

The invention also provides intrabodies that are intracellularly expressed single-chain antibody molecules designed to specifically bind and inactivate target molecules inside cells. Intrabodies have been used in cell assays and in whole organisms (Chen, S. Y., et al. (1994) *Hum. Gene Ther.* 5:595-601; Hassanzadeh, G. H. G., et al. (1998) *FEBS Lett.* 437:75-80). Inducible expression vectors can be constructed with intrabodies that react specifically with a protein of the invention. These vectors can be introduced into host cells and model organisms.

The invention provides artificial antibodies, i.e., antibodies and antibody fragments produced and selected in vitro. In some embodiments, these antibodies, or fragments thereof are displayed on the surface of a bacteriophage or other viral particle, as described above. Suitable fragments include single chain variable region antibodies. In other embodiments, artificial antibodies are present as fusion proteins with a viral or bacteriophage structural protein, including, but not limited to, M13 gene III protein. Methods of producing such artificial antibodies are well known in the art (U.S. Pat. Nos. 5,516,637; 5,223,409; 5,658,727; 5,667,988; 5,498,538; 5,403,484; 5,571,698; and 5,625,033). The artificial antibodies, selected for example, on the basis of phage binding to selected antigens, can be fused to a Fc fragment of an immunoglobulin for use as a therapeutic, as described, for example, in U.S. Pat. No. 5,116,964 or WO 99/61630.

In an embodiment, artificial antibodies of the invention include genetically engineered antibodies. Single chain variable region antibodies are within the scope of such an embodiment. Engineered antibodies may incorporate non-antibody domains, including, for example, coiled coil domains for dimerization, linkers, or other such useful modifications. Genetically engineered antibodies of the invention include proteins with predetermined ligand specificity based on a known or predicted epitope, for example anticalins (Schlehuber, S., and Skerra, A. (2001) *Biol. Chem.* 382:1335-1342), which are suitable for use in the invention when an immunogenic, cross-linking, or effector property of an antibody is undesirable.

For in vivo use, particularly for injection into humans, in some embodiments it is desirable to decrease the antigenicity of the antibody. An immune response of a recipient against the antibody may potentially decrease the period of time that the therapy is effective. Methods of humanizing antibodies are known in the art. The humanized antibody can be the product of an animal having transgenic human immunoglobulin genes, for example, constant region genes (Grosveld, F. and Kollias, G., eds. (1992) *Transgenic Animals.* $1^{st}$ ed. Academic Press.; Murphy, D., and Carter, D. A., eds. (1993) *Transgenesis Techniques Principles and Protocols.* Humana Press.; Pinkert, C. A., ed. (1994) *Transgenic Animal Technology: A Laboratory Handbook.* Academic Press.; and International Patent Applications WO 90/10077 and WO 90/04036). Alternatively, the antibody of interest can be engineered by recombinant DNA techniques to substitute the CH1, CH2, CH3, hinge domains, and/or the framework domain with the corresponding human sequence (see, for example, WO 92/02190).

Thus, antibodies of the invention can be partially human or fully human antibodies. For example, xenogenic antibodies, which are produced in animals that are transgenic for human antibody genes, can be employed to make a fully human antibody. By xenogenic human antibodies is meant antibodies that are fully human antibodies, with the exception that they are produced in a non-human host that has been genetically engineered to express human antibodies (see for example, WO 98/50433; WO 98/24893 and WO 99/53049).

Humanized antibodies can be produced by immunizing mice that make human antibodies. The mouse lines developed by XenoMouse (U.S. Pat. Nos. 5,939,598; 6,075,181; 6,091,001; 6,114,598; 6,150,584; 6,162,963; 6,657,103; 6,673,986; 6,682,736) Medarex (U.S. Pat. Nos. 5,922,845; 6,111,166; 6,410,690; 6,680,209) and Kirin (U.S. Pat. Nos. 6,320,099; 6,632,976) are suitable for use in the invention. Humanized antibodies can also be made, for example, using the technology of Protein Design Labs, Inc. (Fremont, Calif.) (Coligan, J. E. et al., eds. (2002) *Current Protocols in Immunology*, Vols. 1-4 (including quarterly suppl.). John Wiley and Sons, Inc.). Both polyclonal and monoclonal antibodies made in non-human animals may be humanized before administration to human subjects.

Chimeric immunoglobulin genes constructed with immunoglobulin cDNA are known in the art (Liu A. Y., et al.

(1987a) *Proc. Natl. Acad. Sci. USA* 84:3439-3443.; Liu, A. Y., et al. (1987b) *J. Immunol.* 139:3521-3526). Messenger RNA is isolated from a hybridoma or other cell producing the antibody and used to produce cDNA. The cDNA of interest can be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant (C) regions genes are known in the art (Kabat, E. A. and Wu, T. T. (1991) *J. Immunol.* 147:1709-1719). Human C region genes are readily available from known clones. The choice of isotype will be guided by the desired effector functions, such as complement fixation, or antibody-dependent cellular cytotoxicity. IgG1, IgG2, IgG3, and IgG4 isotypes, and either of the kappa or lambda human light chain constant regions can be used. The chimeric, humanized antibody is then expressed by conventional methods.

Consensus sequences of heavy (H) and light (L) J regions can be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

A convenient expression vector for producing antibodies is one that encodes a functionally complete human CH or CL immunoglobulin sequence, with appropriate restriction sites engineered so that any VH or VL sequence can be easily inserted and expressed, such as plasmids, retroviruses, YACs, or EBV derived episomes, and the like. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody can be joined to any strong promoter, including retroviral LTRs, for example, SV-40 early promoter (Okayama, H., and Berg, P. (1983) *Mol. Cell. Biol.* 3:280-289), Rous sarcoma virus LTR (Gorman, et al. (1982) *Proc. Natl. Acad. Sci.* 79:6777-6781), and Moloney murine leukemia virus LTR (Grosschedl, R. and Baltimore, D. (1985) *Cell* 41:885-897), or native immunoglobulin promoters.

Antibody fragments, such as Fv, F(ab')$_2$, and Fab can be prepared by cleavage of the intact protein, for example, by protease or chemical cleavage. These fragments can include heavy and light chain variable regions. Alternatively, a truncated gene can be designed, for example, a chimeric gene encoding a portion of the F(ab')$_2$ fragment that includes DNA sequences encoding the CH1 domain and hinge region of the H chain, followed by a translational stop codon.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference in their entireties.

It must be noted that, as used herein and in the appended claims, the singular forms "a," "or," and "the" include plural referents unless the context clearly dictates otherwise. Thus, for example, reference to "a subject polypeptide" includes a plurality of such polypeptide's and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

The specification is most thoroughly understood in light of the references cited herein. Each of these references is hereby incorporated by the reference in its entirety.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Microarray Analysis of Cluster 192473 Gene Expression Showing Cluster 192473 Gene Overexpression in a Higher Percentage of Melanoma, Ovarian Cancer, and Colon Cancer Specimens, than Normal Controls Polynucleotides and polypeptides encoded by genes that are expressed by cancerous cells may serve as therapeutic and/or diagnostic targets. One potential method that can be used to identify such targets expressed by cancerous cells is microarray analysis. Described below, are the steps that were used to demonstrate gene expression at cluster 192473 in ovarian cancer, melanoma, and colon cancer. The analysis included 4,542 combined normal tissues, 95 normal ovarian specimens, 128 ovarian cancer specimens, 93 melanoma specimens, 257 normal colon specimens, and 76 colon cancer specimens, which are all included in a proprietary oncology database assembled by Gene Logic Inc. (Gaithersburg, Md.). The oncology database was probed by an Affymetrix U133 chip probe (232504_at) that included a cluster 192473-specific probe set designed and produced by Affymetrix. The relative location of the binding site on the cluster 192473 gene for the probes is shown on FIG. 1 at letter C.

Results were reported in terms of the target sequence of each nucleotide probe as being detected or undetected. The intensity of each hybridization reaction was also quantified. We considered a probe set a "hit" when a particular target was detected in tumor tissues and undetected or low in normal tissues. The targets of the invention were identified by this method as positive hits.

High expression of the cluster 192473 gene was observed to occur in five percent of ovarian cancer specimens versus 0% in ovarian tissue controls; in 13% of colon cancer specimens versus colon tissue controls; and in 35% of melanoma specimens (Table 3). The percentage of combined normal tissue types, which included that showed high cluster 192473 gene expression was one percent. Accordingly, these results indicated that the polynucleotides and polynucleotides assigned to cluster 192473 and the cluster 192473 sequences provided by Tables 1-3, could serve as therapeutic and diagnostic targets for the treatment and diagnosis of at least a subset of ovarian cancer, colon cancer, and melanoma tumors.

Example 2

Exon Map of Cluster 192473

Nucleotide sequences assigned to cluster 192473, and identified as being expressed in breast cancer, colon cancer, melanoma, and ovarian cancer tissue specimens (Example 1 and FIGS. 2 and 4), were mapped to the human genome according to the relative positions of the sequences to their corresponding sequences on the genome. The relative position of cluster 192473 nucleotide sequences with regard to the human genome was determined by comparing the cluster 192473 nucleotide sequences with publicly available genomic sequence databases. One advantage of knowing the genomic position of cluster 192473 is that it will allow the determination of whether this cluster is within, or near, a region of chromosomal amplification. This determination may be helpful in understanding the association of cluster 192473 gene expression with different types of cancer, including breast cancer, colon cancer, melanoma, and/or ovarian cancer.

The alignment of cluster 192473 nucleotide sequences with the genome helpful in the determination of the likely exon structure of a gene located at cluster 192473. For example, at FIG. 1, the representation of the cDNA sequence designated CLN00491404, that is also labeled "D," shows that this cDNA sequence includes nucleotide sequences from at least two exons, wherein the two exons border a more than 1,500 bp long intron. Knowledge of the exon structure of a gene is helpful for designing PCR primers to be used for gene expression analysis. Accordingly, knowledge of the exon structure of the cluster 192473 gene as shown in FIG. 1, was helpful for designing the quantitative real time PCR primer sets that were used to generate the overexpression data for breast cancer and melanoma, for FIGS. 2 and 3, respectively. Also depicted in FIG. 1 is the sequence for the nucleotide sequence NCBI 2749857, which is labeled "A," and relates to SEQ. ID. NOS. contained in Table 1. Further, the NCBI 2749857 sequence that is represented by line A in FIG. 1, contains a predicted 5' untranslated region, an open reading frame (ORF), and a predicted 3' untranslated region. Knowledge of the location of each of those regions is helpful when designing nucleotide probes to detect and/or analyze gene expression. For example, line "B" of FIG. 1 represents the ORF of NCBI 2749857. Nucleotide probes and PCR primers designed to target the ORF could, for example, be used to identify splice variants in the coding regions of the gene corresponding to NCBI 2749857 and SEQ. ID. NO. 104. Similarly, there are advantages of designing nucleotide probes and PCR primers that target the 3' untranslated region. One of these advantages is that such nucleotide probes and PCR primers allow for the detection of all splice variants, regardless of the effect splicing has on the ORF. In FIG. 1, the nucleotide sequence labeled "C," included the target sequence of the microarray probes used to identify gene expression at cluster 192473, as described in Example 1.

Example 3

Figure 2:
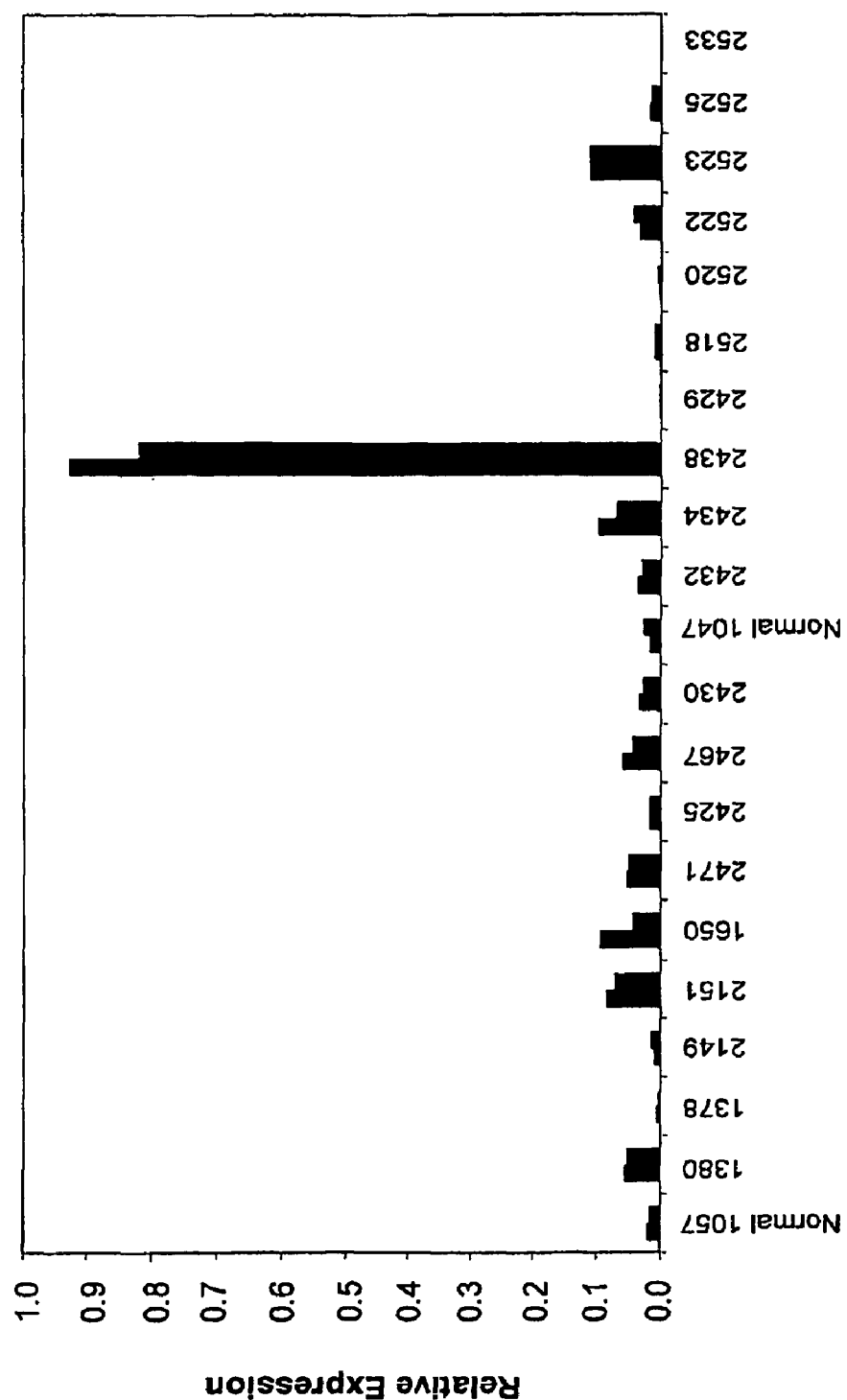
FIG. 2 shows the gene expression level of cluster 192473 in 19 breast cancer tissues and in two normal breast tissues as detected by quantitative real time PCR using probes F-2, R-2 complement, and P-2 CFAM, all of which are specific to genes in cluster 192473 and described in FIG. 1.

Quantitative Real Time PCR Analysis of Gene Expression at Cluster 192473 in Breast Cancer and Normal Breast Tissue Specimens If the overexpression of a particular gene is associated with one or more types of cancer, that gene and its encoded polynucleotides and polypeptides may serve as a therapeutic and diagnostic target of modulators and diagnostic agents. One method available for determining whether a gene is overexpressed is quantitative real time-PCR. Indeed, as shown in FIG. 2, quantitative real time PCR was used to demonstrate the over expression of a gene in cluster 192473, corresponding to NCBI 2749857, and the polynucleotide and polypeptide sequences provided in Tables 1 and 2.

Real-time PCR analysis was performed using a primer set designed to amplify a target sequence is contained within the ORF of the gene in cluster 192473 corresponding to NCBI 27498157 and described above in FIG. 1 and Example 2. This target sequence is common to SEQ. ID. NO.:104 and the CLN0049104 featured in FIG. 1. The sequence of the forward primer was 5' GAACAGGAATGCAAAGGCTTTG 3' and the sequence of reverse primer was 5' GCACCCAGCTGAC-CATGTC 3'. The location of the binding sites for the forward and reverse primers are indicated on FIG. 1 by F-2 and R-2 Complement, respectively.

The following tissue specimens were analyzed: 19 breast cancer specimens and 2 normal breast specimens resected from adjacent cancerous tissue. All specimens were flash frozen in liquid nitrogen, transported on dry ice, and stored at minus 180° C. in liquid nitrogen until needed. Histology was performed on a sample of each frozen tissue specimen and reviewed by a pathologist to confirm the cancer diagnosis or the tissue's normality. Only confirmed specimens were used for quantitative real time PCR experiments.

RNA was isolated from the tissues by grinding them to a fine powder under liquid nitrogen with a pre-chilled mortar and pestle. Total RNA was extracted using TRIzol reagent (Invitrogen, Carlsbad, Calif., USA) according to the manufacturer's protocol and then treated with DNase in a final volume of 500 µl using 350 µg total RNA, 35 U DNase I, 50 µl DNase buffer and 280 U RNaseOUT (all from Invitrogen). Following incubation at 37° C. for 30 min., 500 µl phenol:chloroform:isoamyl alcohol (Invitrogen) was added, and the mixture vortexed, spun at 14,000 rpm for 5 min., and the aqueous phase transferred to a new 2 ml tube. The RNA was then ethanol precipitated by adding 80 µL 5 M $NH_4OAc$, 1.5 ml EtOH, incubated at −20° C. for 30 min., then spun at 14,000 rpm for 30 min. The pellet was washed with 75% EtOH and resuspended with 20 µL $H_2O$. The quality and concentration of the RNA were determined spectrophotometrically at 260 and 280 nm wavelengths and by agarose gel electrophoresis.

The RNA was then used as a template to prepare cDNA. First-strand cDNA synthesis was performed in a final volume of 20 µl with 10 µg total RNA, 5 µM T7-linked oligo$(dT)_{24}$ primer, 4 µl of 5× first-strand cDNA buffer, 10 mM DTT, 0.5 mM dNTP mix and 400 U Superscript II reverse transcriptase (all from Invitrogen). This mixture was incubated at 42° C. for 80 min. Second-strand cDNA synthesis was performed in a final volume of 150 µl using 20 µl of the first strand synthesis mixture, 30 µl 5× second-strand reaction buffer, 0.2 mM dNTP mix, 10 U *E. coli* DNA ligase, 40 U *E. coli* DNA polymerase I, and 2 U *E. coli* RNase H. This mixture was incubated at 16° C. for 2 h. Then 20 U DNA polymerase was added and incubation at 16° C. continued for an additional 5 min.

Quantitative real time PCR analysis of cluster 192473 gene expression for each specimen was then performed in duplicate in a 25 µl reaction volumes containing 2× TaqMan Universal PCR Master Mix (Applied Biosystems), primers at a final concentration of 900 nM each, 250 nM probe, water to a 20 µl final volume, and 5 µl of the cDNA. Reactions were conducted using the following amplification parameters: 2 min. at 50° C., 10 min. at 95° C., 40 cycles of 15 sec. at 95° C. and 1 min. at 60° C. Analysis of the reactions was performed using an ABI Prism 7000 Sequence Detection System (Applied Biosystems).

As shown in FIG. 2, results from quantitative real time PCR analysis of relative gene expression at cluster 192473 demonstrated overexpression as compared to controls (Normal 1057 and Normal 1047) in at least eight of the 19 breast cancer specimens analyzed (Breast cancer specimens 1380, 2151, 1650, 2471, 2467, 2434, 2438, and 2523). Significant overexpression was observed for specimen No. 2438 (FIG. 2). Accordingly, these results indicated that the polynucleotides and polynucleotides assigned to cluster 192473 and the cluster 192473 sequences provided by Tables 1 and 2, could serve as therapeutic and diagnostic targets for the treatment and diagnosis of at least a subset of breast cancer tumors.

Example 4

Quantitative Real Time PCR Analysis of Gene Expression at Cluster 192473 in Melanoma Tissue Specimens Quantitative real time PCR was also used to show that gene overexpression at cluster 192473 could occur in a subset of melanoma tissue specimens. Analysis of cluster 192473 gene expression in melanoma specimens was performed using the same primer set described above in Example 3.

Two melanoma specimens were analyzed. Handling of the specimens, extraction of RNA, preparation of cDNA, and the set-up of the PCR were carried out as described above in Example 4.

As shown in FIG. 3, results from quantitative real time PCR analysis of relative gene expression at cluster 192473 demonstrated greater cluster 192473 gene expression in melanoma specimen 1871, than in specimen 1777 (FIG. 3). Accordingly, these results indicated that the polynucleotides and polynucleotides assigned to cluster 192473 and the cluster 192473 sequences provided by Tables 1-3, could serve as therapeutic and diagnostic targets for the treatment and diagnosis of at least a subset of melanoma tumors.

Example 5

Quantitative Real Time PCR Analysis of Gene Expression at Cluster 192473 in Normal Tissue Specimens Gene expression at cluster 192473 was also assessed for a panel of normal tissue specimens (FIG. 4). Analysis of cluster 192473 gene expression in normal tissue specimens was performed using the same primer set described above for Example 4.

The following tissue specimens were analyzed: 7 normal heart specimens; 5 normal kidney specimens; 1 normal placenta specimen; 5 normal liver specimens; 1 normal fat specimen; 3 normal muscle specimens; and 3 normal adrenal gland specimens (FIG. 4). Handling of the specimens, extraction of RNA, preparation of cDNA, and the set-up of the PCR were carried out as described above in Example 4.

As shown in FIG. 4, results from quantitative real time PCR analysis of relative gene expression at cluster 192473 demonstrated greater cluster 192473 gene expression in five out of the five lung specimens and in one of the three squamous lung specimens (specimen 2653), than in all of the other normal tissues analyzed.

Example 6

Predicted Amino Acid Sequence of Cluster 192473-Derived Polypeptides

The design of modulators and/or diagnostic agents, for example, antibodies, may require knowing the amino acid sequence of the desired target sequence, or as it is also termed, the epitope. The design of useful modulators, including antibody modulators, that are specific for the polypeptides encoded by polynucleotide sequences assigned to cluster 192473, may be facilitated by knowledge of the primary amino acid sequence. Therefore, the amino acid sequence of the polypeptide encoded by SEQ. ID. NOS.: 1 and 104, which is assigned to cluster 192473 and found in Table 1, was predicted. The full-length amino acid sequence of this polypeptide is provided by SEQ. ID. NO. 4 and is also represented in Table 1. The full length polypeptide, as well as large amino-terminal and carboxy-terminal fragments of this polypeptide, provided by SEQ. ID. NOS.: 5 and 6, may be considered for the design and generation of antibodies specific for cluster 192473 encoded polypeptides. In addition, since antibody epitopes commonly comprise six or fewer amino acids, Table 1 also provides a listing of polypeptide fragments, each six amino acids in length (SEQ. ID. NOS.:

7-103), and one larger fragment (SEQ. ID. NO.: 105), that may also be useful for the design and generation of epitope-specific antibodies.

Last, knowledge of how a polypeptide interacts with membranes may also be of value when considering desirable target sequences for use as antibody or modulator targets. To this end, the cluster 192473 polypeptide represented by SEQ. ID. NO. 4 and encoded by NCBI 27498157, was subjected to an internally developed algorithm designed to indicate the position of the beginning and ending amino acid residues spanning the TM domain (TM domains). This algorithm predicted that the cluster 192473 polypeptide described above contained at least one TM domain and that the domain spanned amino acids 42-64, based on the predicted amino acid sequence. Accordingly, based on these predictions, antibodies and/or modulators may be designed to either target or not target the TM domain of the cluster 192473 polypeptide discussed herein.

Example 7

Exon Map of Cluster 800228

Nucleotide sequences assigned to cluster 800228, and identified as expressed in certain breast cancer, ovarian cancer, prostate cancer, and stomach cancer specimens, were mapped to the human genome according to the relative positions of the sequences to their corresponding sequences on the genome (FIG. 5). The relative position of cluster 800228 nucleotide sequences with regard to the human genome was determined by comparing the cluster 800228 nucleotide sequences with publicly available genomic sequence databases. An advantage of knowing the genomic position of cluster 800228 is that it will allow the determination of whether this cluster is within, or near, a region of chromosomal amplification. This determination may be helpful in understanding the association of cluster 800228 gene expression with different types of cancer, including breast cancer, ovarian cancer, prostate cancer, and stomach cancer.

The alignment of cluster 800228 nucleotide sequences with the genome was helpful in the determination of the likely exon structure of a gene located at cluster 800228. For example FIG. 5 shows the schematic representation of 11 individual nucleotide sequences, which have all been given a CLN-based identification designation. Each of the CLN sequences are comprised of nucleotide sequences corresponding to two exons, separated by more than 500 bp intronic sequence. Knowledge of the exon structure of a gene is helpful for designing PCR primers to be used for gene expression analysis. Accordingly, knowledge of the exon structure of the cluster 800228 gene as shown in FIG. 5, was helpful for designing the quantitative real time PCR primer sets that were used to generate the overexpression data for breast cancer (FIG. 6).

Example 8

Quantitative Real Time PCR Analysis of Gene Expression at Cluster 800228 in Breast Cancer and Normal Breast Tissue Specimens Analysis of cluster 800228 gene overexpression in breast cancer and normal breast tissue specimens was performed in a manner similar to that described in Example 3 for analyzing cluster 192473 gene expression. Demonstration of cluster 800228 gene overexpression in certain breast cancer specimens suggested the polynucleotides and polypeptides assigned to cluster 800228 may serve as therapeutic and diagnostic targets for modulators, including for example, antibodies.

Real-time PCR analysis was performed using a primer set designed to amplify a nucleotide sequence contained within the ORF of the gene at cluster 800228, corresponding to any of the sequences represented and described above in FIG. 5 and Example 7. The sequence of the forward primer was 5' CCGGTGGATTTTTGCTTCTG 3' and the sequence of reverse primer was 5' GCCTCTTGTTGGACTGGAGAGA 3'. This PCR primer set was designed to amplify a nucleotide sequence that included the boundary between the first and second exons of the gene at cluster 800228, as represented by the CLN sequences provided in FIG. 5.

The breast cancer and normal breast tissue specimens described in Example 3 were also used for the cluster 800228 expression analysis. In addition, handling of the specimens, extraction of RNA, preparation of cDNA, and the set-up of the PCR were all performed as described above in Example 3.

As shown in FIG. 6, results from quantitative real time PCR analysis of relative gene expression at cluster 800228 demonstrated overexpression as compared to controls (Normal 1057 and Normal 1047) in at least four of the 19 breast cancer specimens analyzed (Breast cancer specimens 1650, 2471, 2432, and 2438). Greater expression was observed for specimen No. 2438 (FIG. 7). Accordingly, these results indicated that the polynucleotides and polynucleotides assigned to cluster 800228 and the cluster 800228 sequences provided by Tables 4 and 5 can serve as therapeutic and diagnostic targets of modulators, such as antibodies, that may be useful for the treatment and diagnosis of certain breast cancer tumors.

Example 9

Quantitative Real Time PCR Analysis of Gene Expression at Cluster 800228 in Normal Tissue Specimens Gene expression at cluster 800228 was also assessed for a panel of normal tissue specimens (FIG. 7). As was described for above in Example 8 for gene expression analysis of breast cancer specimens, real-time PCR analysis of cluster 800228 gene expression in normal tissue specimens was performed using the same primer described above in Example 8.

The following tissue specimens were analyzed: 7 normal heart specimens; 5 normal kidney specimens; 1 normal placenta specimen; 5 normal liver specimens; 1 normal fat specimen; 3 normal muscle specimens; and 3 normal adrenal gland specimens (FIG. 8). Handling of the specimens, extraction of RNA, preparation of cDNA, and the set-up of the PCR were all done as described above in Example 4.

As shown in FIG. 8, results from quantitative real time PCR analysis of relative gene expression at cluster 800228 demonstrated greater cluster 800228 gene expression in five out of the five lung specimens and in one of the three squamous lung specimens (specimen 2653), than in all of the other normal tissues analyzed.

Example 10

Clustal Analysis of Human and Chimp Amino Acid Sequences Assigned to Cluster 800228

Since human- and chimp-derived homologue polypeptides typically share significant sequence identity, the chimp homologue of a specified polypeptide may often be considered when selecting target sequences or target polypeptides to be used for the generation of antibodies and modulators. Accordingly, in order to help provide potential alternative amino acid sequences on which to base the design of antibodies and modulators assigned to cluster 800228, a sequence comparison of the human amino acid sequence of SEQ. ID. NO.: 112, a fragment of SEQ. ID. NO.: 111 (Table 4), was compared to the chimp amino acid sequence of SEQ. ID. NO.: 165 (Table 4).

The alignment of these sequences as shown in FIG. 8 was performed using the clustal format for T-COFFEE Version_ 1.37. Plus signs placed by the human and chimp amino acid residues at each point of comparison (+) indicate amino acid residues shared among all the sequences; colons; a single plus sign by either a human or a chimp amino acid residue, but not both (/+) indicate conservative amino acid changes; and the absence of a plus sign between residues indicate nonconserved amino acids.

Example 11

Predicted Amino Acid Sequence of Cluster 800228-Derived Polypeptides

The amino acid sequence of the full-length polypeptide assigned to cluster 800228 is represented by SEQ. ID. NOS.: 109 and 111, which are assigned to cluster 800228 and found in Table 4. The full length polypeptide, as well as a large carboxy-terminal fragment of this polypeptide, represented by SEQ. ID. NO.: 112, may be considered for the design and generation of antibodies specific for cluster 800228-encoded polypeptides. In addition, since antibody epitopes commonly comprise six or fewer amino acids, Table 1 also provides a listing of polypeptide fragments, each six amino acids in length (SEQ. ID. NOS.: 113-147, and 149-164), as well as one larger fragment (SEQ. ID. NO.: 148), and six amino acid fragments (SEQ. ID. NOS.: 167-176), derived from SEQ. ID. NO.: 165, that may also be useful for the design and generation of epitope-specific antibodies.

Last, knowledge of how a polypeptide interacts with cell membranes may also be of value when considering amino acid sequences to be used as desirable antibody or modulator target sequences. To this end, the cluster 800228 polypeptide defined by SEQ. ID. NO. 111 and encoded by CLN00496840.a, was subjected to internally developed algorithm used to indicate the position of the beginning and ending amino acid residues spanning the TM domain (TM domains). This algorithm predicted that the cluster 800228 polypeptide described above contained at least one TM domain and that the domain spanned amino acids 22-44, based on the predicted amino acid sequence. Accordingly, based on these predictions, antibodies and/or modulators may be designed to either target or not target the TM domain of the cluster 800228 polypeptide discussed herein.

Example 12

Amplicon Mapping of Cluster 800228

For many types of cancer, there may be a positive relationship between amplicons, which are regions of chromosomal amplification, and the expression of genes located nearby. The increased expression of a gene located within or near an amplicon may be because that gene has been amplified as well. Determination of the relationship between a gene and an amplicon depends on a statistical calculation that results in a p-value. Based on the p-value for a specified gene, that gene may then be ranked according to its p-value as compared to all other genes associated with an amplicon that is active for a particular type of cancer. This data is shown in the 'log p-value' and 'rank' columns of Table 6. Cluster 800228 was mapped to a genomic region that fell close to amplicons that were detected in the cancer tissue specimens listed in Table 6. The fourth column (Distance to the Amplicon) shows this distance measured in nucleotides. The cancer types listed in the table are examples of the types of cancers showing amplicon activity within 1000000 nucleotides of the 800228 cluster. They include stomach cancer, prostate cancer, breast cancer (specifically breast infiltrating ductile carcinoma), and ovarian cancer. Accordingly, the genomic proximity between cluster 800228 and an amplicon increases the likelihood that cluster 800228 is also amplified in a subset of the forementioned cancers. Further, chromosomal amplification could enhance tumor survival so cluster 800228 could be playing such a role.

Example 13

Exon Map of Cluster 800634

Nucleotide sequences assigned to cluster 800634, and identified as being overexpressed in breast cancer, lung cancer, and ovarian cancer specimens, were mapped to the human genome according to the relative positions of the sequences to their corresponding sequences on the genome (FIG. 11). The relative position of cluster 800634 nucleotide sequences with regard to the human genome was determined by comparing the cluster 800634 nucleotide sequences with publicly available genomic sequence databases. One advantage of knowing the genomic position of cluster 800634 is that it will allow the determination of whether this cluster is within, or near, a region of chromosomal amplification. This determination may be helpful in understanding the association of cluster 800634 gene expression with different types of cancer, including breast cancer, lung cancer, and ovarian cancer.

The alignment of cluster 800634 nucleotide sequences with the genome helped to deduce the likely exon structure of a gene located at cluster 800634. For example FIG. 9 shows the schematic representation of 6 individual nucleotide sequences, which have all been given a CLN-based identification designation. Knowledge of the exon structure of a gene is helpful for designing PCR primers to be used for gene expression analysis. Accordingly, knowledge of the exon structure of the cluster 800634 gene as shown in FIG. 11, was helpful for designing the quantitative real time PCR primer sets that were used to generate the overexpression data for breast cancer (FIG. 12).

Example 14

Quantitative Real Time PCR Analysis of Gene Expression at Cluster 800634 in Breast Cancer and Normal Breast Tissue Specimens Analysis of cluster 800634 gene overexpression in breast cancer and normal breast tissue specimens was performed in a manner similar to that described in Example 3 for analyzing cluster 192473 gene expression. Demonstration of cluster 800634 gene overexpression in certain breast cancer specimens suggested the polynucleotides and polypeptides assigned to cluster 800634 may serve as therapeutic and diagnostic targets for modulators, including for example, antibodies.

Real-time PCR analysis was performed using a primer set designed to amplify a nucleotide sequence contained within the ORF of the gene at cluster 800634, corresponding to any of the sequences represented and described above in FIG. 9 and Example 13. The sequence of the forward primer was 5' CATACCTTTGCCAGCAGAGTCA 3' and the sequence of reverse primer was 5' GGCATTCATTTCCCTCAGCAT 3'.

The following tissue specimens were analyzed: 19 prostate cancer specimens, three normal prostate controls, 19 breast cancer specimens and two normal breast specimens resected from adjacent cancerous tissue. The results are shown in FIG. 10, with the prostate specimens arranged in the left half of the figure and the breast specimens on the right half of the figure. Handling of the specimens, extraction of RNA, preparation of cDNA, and the set-up of the PCR were all done as described above in Example 4.

Among the pancreatic cancer specimens, cluster 800634 gene expression was relatively low in the cancer specimens as compared to the control specimens (Normal 994, Normal 995, and Normal 1097). Whereas, among the breast cancer specimens, gene expression at cluster 800634 was greater in at least nine of the 19 breast cancer specimens analyzed (Breast cancer specimens 1650, 2471, 2467, 2432, 2438, 2520, 2522, 2523, and 2433) as compared to controls (Normal 1057 and Normal 1047).

Example 15

Quantitative Real Time PCR Analysis of Gene Expression at Cluster 800634 in Normal Tissue Specimens Gene expression at cluster 800634 was also assessed for a panel of normal tissue specimens (FIG. 11). As was described for above in Example 13 for gene expression analysis of breast cancer specimens, real-time PCR analysis of cluster 800634 gene expression in normal tissue specimens was performed using the same primer set described above for Example 13.

The following tissue specimens were analyzed: 7 normal heart specimens; 5 normal kidney specimens; 1 normal placenta specimen; 5 normal liver specimens; 1 normal fat specimen; 3 normal muscle specimens; and 3 normal adrenal gland specimens (FIG. 11). Handling of the specimens, extraction of RNA, preparation of cDNA, and the set-up of the PCR were all done as described above in Example 3.

As shown in FIG. 11, results from quantitative real time PCR analysis of relative gene expression at cluster 800634 demonstrated greater cluster 800634 gene expression in two (specimens 2191 and 2197) out of the five liver specimens and in one (specimen 2855) of the five kidney specimens, than in all of the other normal tissues analyzed.

Example 16

Predicted Amino Acid Sequence of Cluster 800634-Derived Polypeptides

The full-length amino acid sequences of the polypeptides assigned to cluster 800634 are represented by SEQ. ID. NOS.: 185 and 294, respectively (Table 7). The full length polypeptide, as well as fragments of this polypeptide, including SEQ. ID. NOS.: 293. and 295-297, may be considered for the design and generation of antibodies specific for cluster 800634-encoded polypeptides. In addition, since antibody epitopes commonly comprise six or fewer amino acids, Table 1 also provides a listing of polypeptide fragments, each six amino acids in length (SEQ. ID. NOS.: 186-292, and 298-366), that may also be useful for the design and generation of epitope-specific antibodies.

The prediction of whether or not a specified therapeutic or diagnostic polypeptide target is secreted, also may help to determine how an antibody or modulator is expected to function. The probability of whether cluster 800634 polypeptides defined by SEQ. ID. NO. 185 and SEQ. ID. NO. 294 and encoded by CLN00156137.a (SEQ. ID. NO. 179) and CLN00156137.b SEQ. ID. NO. 181), respectively were secreted was determined by using an internally developed decision tree algorithm that predicts whether the polypeptide is a secreted protein. The probability of secretion is referred to as a Treevote score, with "1" corresponding to a high probability that the polypeptide is secreted and "0" corresponding to a low probability that the polypeptide is secreted. Table 8 shows the Tree-vote score for the polypeptides of CLN00156137 and CLN00156137.b. Based on the Treevote score for these two polypeptides it may be considered that the polypeptide encoded by CLN00156137.b is more likely to be secreted, even though both CLN00156137.a and CLN00156137.b polypeptides were predicted by an internally developed algorithm, to possess signal peptides (Table 8).

Last, knowledge of how a polypeptide interacts with membranes may also be of value when considering amino acid sequences to be used as desirable antibody or modulator target sequences. To this end, the cluster 800634 polypeptides defined by SEQ. ID. NO. 185 and SEQ. ID. NO. 294 and encoded by CLN00156137.a (SEQ. ID. NO. 179) and CLN00156137.b SEQ. ID. NO. 181), respectively were subjected to an internally developed algorithm used to indicate the position of the beginning and ending amino acid residues spanning the TM domain (TM domains). This algorithm predicted that the cluster 800634 polypeptide of CLN00156137.b (SEQ. ID. NO. 294) contained at least one TM domain and that the domain spanned amino acids 44-66, based on the predicted amino acid sequence. Accordingly, based on these predictions, antibodies and/or modulators may be designed to either target or not target the TM domain of the cluster 800634 polypeptide encoded by CLN00156137.b, which is represented by the nucleotide sequence of SEQ. ID. NO.: 181.

SEQUENCE LISTING

A sequence listing transmittal sheet and a sequence listing in paper format accompanies this application.

TABLES

TABLE 1

| FP ID | SEQ. ID. NO. (N1) | SEQ. ID. NO. (P1) | SEQ. ID. NO. (N0) | Source ID | Sequence |
|---|---|---|---|---|---|
| HG1019919 | SEQ. ID. NO.: 1 | SEQ. ID. NO.: 4 | SEQ. ID. NO.: 104 | 27498158: 27498157 (FL) | |

TABLE 1-continued

| FP ID | SEQ. ID. NO. (N1) | SEQ. ID. NO. (P1) | SEQ. ID. NO. (N0) | Source ID | Sequence |
|---|---|---|---|---|---|
| HG1019920 | SEQ. ID. NO.: 2 | SEQ. ID. NO.: 5 | | 27498158_frag1 | (1-41) |
| HG1019921 | SEQ. ID. NO.: 3 | SEQ. ID. NO.: 6 | | 27498158_frag2 | (65-130) |
| HG1019922 | | SEQ. ID. NO.: 7 | | 27498158_frag3 | MIFPPS |
| HG1019923 | | SEQ. ID. NO.: 8 | | 27498158_frag4 | IFPPSS |
| HG1019924 | | SEQ. ID. NO.: 9 | | 27498158_frag5 | FPPSSR |
| HG1019925 | | SEQ. ID. NO.: 10 | | 27498158_frag6 | PPSSRD |
| HG1019926 | | SEQ. ID. NO.: 11 | | 27498158_frag7 | PSSRDQ |
| 4HG1019927 | | SEQ. ID. NO.: 12 | | 27498158_frag8 | SSRDQR |
| HG1019928 | | SEQ. ID. NO.: 13 | | 27498158_frag9 | SRDQRE |
| HG1019929 | | SEQ. ID. NO.: 14 | | 27498158_frag10 | RDQREL |
| HG1019930 | | SEQ. ID. NO.: 15 | | 27498158_frag11 | DQRELI |
| HG1019931 | | SEQ. ID. NO.: 16 | | 27498158_frag12 | QRELIE |
| HG1019932 | | SEQ. ID. NO.: 17 | | 27498158_frag13 | RELIEC |
| HG1019933 | | SEQ. ID. NO.: 18 | | 27498158_frag14 | ELIECD |
| HG1019934 | | SEQ. ID. NO.: 19 | | 27498158_frag15 | LIECDN |
| HG1019935 | | SEQ. ID. NO.: 20 | | 27498158_frag16 | IECDND |
| HG1019936 | | SEQ. ID. NO.: 21 | | 27498158_frag17 | ECDNDS |
| HG1019937 | | SEQ. ID. NO.: 22 | | 27498158_frag18 | CDNDSL |
| HG1019938 | | SEQ. ID. NO.: 23 | | 27498158_frag19 | DNDSLA |
| HG1019939 | | SEQ. ID. NO.: 24 | | 27498158_frag20 | NDSLAG |
| HG1019940 | | SEQ. ID. NO.: 25 | | 27498158_frag21 | DSLAGT |
| HG1019941 | | SEQ. ID. NO.: 26 | | 27498158_frag22 | SLAGTA |
| HG1019942 | | SEQ. ID. NO.: 27 | | 27498158_frag23 | LAGTAE |
| HG1019943 | | SEQ. ID. NO.: 28 | | 27498158_frag24 | AGTAEA |
| HG1019944 | | SEQ. ID. NO.: 29 | | 27498158_frag25 | GTAEAS |
| HG1019945 | | SEQ. ID. NO.: 30 | | 27498158_frag26 | TAEASG |

TABLE 1-continued

| FP ID | SEQ. ID. NO. (N1) | SEQ. ID. NO. (P1) | SEQ. ID. NO. (N0) | Source ID | Sequence |
|---|---|---|---|---|---|
| HG1019946 | | SEQ. ID. NO.: 31 | | 27498158_frag27 | AEASGS |
| HG1019947 | | SEQ. ID. NO.: 32 | | 27498158_frag28 | EASGSF |
| HG1019948 | | SEQ. ID. NO.: 33 | | 27498158_frag29 | ASGSFL |
| HG1019949 | | SEQ. ID. NO.: 34 | | 27498158_frag30 | SGSFLR |
| HG1019950 | | SEQ. ID. NO.: 35 | | 27498158_frag31 | GSFLRS |
| HG1019951 | | SEQ. ID. NO.: 36 | | 27498158_frag32 | SFLRSA |
| HG1019952 | | SEQ. ID. NO.: 37 | | 27498158_frag33 | FLRSAV |
| HG1019953 | | SEQ. ID. NO.: 38 | | 27498158_frag34 | LRSAVK |
| HG1019954 | | SEQ. ID. NO.: 39 | | 27498158_frag35 | RSAVKE |
| HG1019955 | | SEQ. ID. NO.: 40 | | 27498158_frag36 | SAVKED |
| HG1019956 | | SEQ. ID. NO.: 41 | | 27498158_frag37 | AVKEDE |
| HG1019957 | | SEQ. ID. NO.: 42 | | 27498158_frag38 | VKEDEK |
| HG1019958 | | SEQ. ID. NO.: 43 | | 27498158_frag39 | RATLSL |
| HG1019959 | | SEQ. ID. NO.: 44 | | 27498158_frag40 | ATLSLC |
| HG1019960 | | SEQ. ID. NO.: 45 | | 27498158_frag41 | TLSLCI |
| HG1019961 | | SEQ. ID. NO.: 46 | | 27498158_frag42 | LSLCIS |
| HG1019962 | | SEQ. ID. NO.: 47 | | 27498158_frag43 | SLCISN |
| HG1019963 | | SEQ. ID. NO.: 48 | | 27498158_frag44 | LCISNK |
| HG1019964 | | SEQ. ID. NO.: 49 | | 27498158_frag45 | CISNKA |
| HG1019965 | | SEQ. ID. NO.: 50 | | 27498158_frag46 | ISNKAK |
| HG1019966 | | SEQ. ID. NO.: 51 | | 27498158_frag47 | SNKAKR |
| HG1019967 | | SEQ. ID. NO.: 52 | | 27498158_frag48 | NKAKRG |
| HG1019968 | | SEQ. ID. NO.: 53 | | 27498158_frag49 | KAKRGC |
| HG1019969 | | SEQ. ID. NO.: 54 | | 27498158_frag50 | AKRGCN |
| HG1019970 | | SEQ. ID. NO.: 55 | | 27498158_frag51 | KRGCNY |

TABLE 1-continued

| FP ID | SEQ. ID. NO. (N1) | SEQ. ID. NO. (P1) | SEQ. ID. NO. (N0) | Source ID | Sequence |
|---|---|---|---|---|---|
| HG1019971 | | SEQ. ID. NO.: 56 | | 27498158_frag52 | RGCNYT |
| HG1019972 | | SEQ. ID. NO.: 57 | | 27498158_frag53 | GCNYTL |
| HG1019973 | | SEQ. ID. NO.: 58 | | 27498158_frag54 | CNYTLL |
| HG1019974 | | SEQ. ID. NO.: 59 | | 27498158_frag55 | NYTLLQ |
| HG1019975 | | SEQ. ID. NO.: 60 | | 27498158_frag56 | YTLLQS |
| HG1019976 | | SEQ. ID. NO.: 61 | | 27498158_frag57 | TLLQSS |
| HG1019977 | | SEQ. ID. NO.: 62 | | 27498158_frag58 | LLQSSV |
| HG1019978 | | SEQ. ID. NO.: 63 | | 27498158_frag59 | LQSSVS |
| HG1019979 | | SEQ. ID. NO.: 64 | | 27498158_frag60 | QSSVSP |
| HG1019980 | | SEQ. ID. NO.: 65 | | 27498158_frag61 | SSVSPG |
| HG1019981 | | SEQ. ID. NO.: 66 | | 27498158_frag62 | SVSPGN |
| HG1019982 | | SEQ. ID. NO.: 67 | | 27498158_frag63 | VSPGNR |
| HG1019983 | | SEQ. ID. NO.: 68 | | 27498158_frag64 | SPGNRN |
| HG1019984 | | SEQ. ID. NO.: 69 | | 27498158_frag65 | PGNRNA |
| HG1019985 | | SEQ. ID. NO.: 70 | | 27498158_frag66 | GNRNAK |
| HG1019986 | | SEQ. ID. NO.: 71 | | 27498158_frag67 | NRNAKA |
| HG1019987 | | SEQ. ID. NO.: 72 | | 27498158_frag68 | RNAKAL |
| HG1019988 | | SEQ. ID. NO.: 73 | | 27498158_frag69 | NAKALK |
| HG1019989 | | SEQ. ID. NO.: 74 | | 27498158_frag70 | AKALKA |
| HG1019990 | | SEQ. ID. NO.: 75 | | 27498158_frag71 | KALKAS |
| HG1019991 | | SEQ. ID. NO.: 76 | | 27498158_frag72 | ALKASL |
| HG1019992 | | SEQ. ID. NO.: 77 | | 27498158_frag73 | LKASLF |
| HG1019993 | | SEQ. ID. NO.: 78 | | 27498158_frag74 | KASLFA |
| HG1019994 | | SEQ. ID. NO.: 79 | | 27498158_frag75 | ASLFAD |
| HG1019995 | | SEQ. ID. NO.: 80 | | 27498158_frag76 | SLFADM |
| HG1019996 | | SEQ. ID. NO.: 81 | | 27498158_frag77 | LFADMV |

TABLE 1-continued

| FP ID | SEQ. ID. NO. (N1) | SEQ. ID. NO. (P1) | SEQ. ID. NO. (N0) | Source ID | Sequence |
|---|---|---|---|---|---|
| HG1019997 | | SEQ. ID. NO.: 82 | | 27498158_frag78 | FADMVS |
| HG1019998 | | SEQ. ID. NO.: 83 | | 27498158_frag79 | ADMVSW |
| HG1019999 | | SEQ. ID. NO.: 84 | | 27498158_frag80 | DMVSWV |
| HG1020000 | | SEQ. ID. NO.: 85 | | 27498158_frag81 | MVSWVP |
| HG1020001 | | SEQ. ID. NO.: 86 | | 27498158_frag82 | VSWVPW |
| HG1020002 | | SEQ. ID. NO.: 87 | | 27498158_frag83 | SWVPWA |
| HG1020003 | | SEQ. ID. NO.: 88 | | 27498158_frag84 | WVPWAK |
| HG1020004 | | SEQ. ID. NO.: 89 | | 27498158_frag85 | VPWAKS |
| HG1020005 | | SEQ. ID. NO.: 90 | | 27498158_frag86 | PWAKSF |
| HG1020006 | | SEQ. ID. NO.: 91 | | 27498158_frag87 | WAKSFC |
| HG1020007 | | SEQ. ID. NO.: 92 | | 27498158_frag88 | AKSFCC |
| HG1020008 | | SEQ. ID. NO.: 93 | | 27498158_frag89 | KSFCCP |
| HG1020009 | | SEQ. ID. NO.: 94 | | 27498158_frag90 | SFCCPP |
| HG1020010 | | SEQ. ID. NO.: 95 | | 27498158_frag91 | FCCPPL |
| HG1020011 | | SEQ. ID. NO.: 96 | | 27498158_frag92 | CCPPLS |
| HG1020012 | | SEQ. ID. NO.: 97 | | 27498158_frag93 | CPPLSP |
| HG1020013 | | SEQ. ID. NO.: 98 | | 27498158_frag94 | PPLSPS |
| HG1020014 | | SEQ. ID. NO.: 99 | | 27498158_frag95 | PLSPSK |
| HG1020015 | | SEQ. ID. NO.: 100 | | 27498158_frag96 | LSPSKL |
| HG1020016 | | SEQ. ID. NO.: 101 | | 27498158_frag97 | SPSKLG |
| HG1020017 | | SEQ. ID. NO.: 102 | | 27498158_frag98 | PSKLGP |
| HG1020018 | | SEQ. ID. NO.: 103 | | 27498158_frag99 | SKLGPF |
| HG1020019 | | SEQ. ID. NO.: 105 | | 27498158_frag100 | RATLSLCISNKAKRG CNYTLLQSSVSPGNR |

TABLE 2

| FP ID | Source ID | FP Cluster No. | Predicted Size | No. of TM Domains | TM Domains | non-TM Domains |
|---|---|---|---|---|---|---|
| HG1019919 | 27498158: 27498157 | 192473 | 130 | 1 | (42-64) | (1-41) (65-130) |

TABLE 3

| Tissue Specimen | Percentage of Tissue Specimens Showing 27498158:27498157 Expression | Total Number of Tissue Specimens |
|---|---|---|
| Normal (all tissue types combined) | 1% | 4542 |
| Normal Ovary | 0% | 95 |
| Malignant Ovary | 5% | 128 |
| Melanoma Related | 35% | 93 |
| Normal Colon | 3% | 257 |
| Malignant Colon | 13% | 76 |

TABLE 4

| FP ID | SEQ. ID. NO. (N1) | SEQ. ID. NO. (P1) | SEQ. ID. NO. (N0) | Source ID | Sequence |
|---|---|---|---|---|---|
| HG1020019 | SEQ. ID. NO.: 106 | SEQ. ID. NO.: 111 | SEQ. ID. NO.: 177 | CLN00496840.a | |
| HG1020020 | SEQ. ID. NO.: 107 | SEQ. ID. NO.: 112 | | CLN00496840_frag1 | (45-84) |
| HG1020021 | | SEQ. ID. NO.: 113 | | CLN00496840_frag2 | LLSHSP |
| HG1020022 | | SEQ. ID. NO.: 114 | | CLN00496840_frag3 | LSHSPA |
| HG1020023 | | SEQ. ID. NO.: 115 | | CLN00496840_frag4 | SHSPAR |
| HG1020024 | | SEQ. ID. NO.: 116 | | CLN00496840_frag5 | HSPARK |
| HG1020025 | | SEQ. ID. NO.: 117 | | CLN00496840_frag6 | SPARKN |
| HG1020026 | | SEQ. ID. NO.: 118 | | CLN00496840_frag7 | PARKNL |
| HG1020027 | | SEQ. ID. NO.: 119 | | CLN00496840_frag8 | ARKNLS |
| HG1020028 | | SEQ. ID. NO.: 120 | | CLN00496840_frag9 | RKNLSF |
| HG1020029 | | SEQ. ID. NO.: 121 | | CLN00496840_frag10 | KNLSFE |
| HG1020030 | | SEQ. ID. NO.: 122 | | CLN00496840_frag11 | NLSFEF |
| HG1020031 | | SEQ. ID. NO.: 123 | | CLN00496840_frag12 | LSFEFL |
| HG1020032 | | SEQ. ID. NO.: 124 | | CLN00496840_frag13 | SFEFLK |
| HG1020033 | | SEQ. ID. NO.: 125 | | CLN00496840_frag14 | FEFLKC |
| HG1020034 | | SEQ. ID. NO.: 126 | | CLN00496840_frag15 | EFLKCI |
| HG1020035 | | SEQ. ID. NO.: 127 | | CLN00496840_frag16 | FLKCII |
| HG1020036 | | SEQ. ID. NO.: 128 | | CLN00496840_frag17 | LKCIIS |
| HG1020037 | | SEQ. ID. NO.: 129 | | CLN00496840_frag18 | KCIISS |
| HG1020038 | | SEQ. ID. NO.: 130 | | CLN00496840_frag19 | CIISSP |
| HG1020039 | | SEQ. ID. NO.: 131 | | CLN00496840_frag20 | IISSPP |
| HG1020040 | | SEQ. ID. NO.: 132 | | CLN00496840_frag21 | ISSPPQ |
| HG1020041 | | SEQ. ID. NO.: 133 | | CLN00496840_frag22 | SSPPQT |
| HG1020042 | | SEQ. ID. NO.: 134 | | CLN00496840_frag23 | SPPQTT |
| HG1020043 | | SEQ. ID. NO.: 135 | | CLN00496840_frag24 | PPQTTC |
| HG1020044 | | SEQ. ID. NO.: 136 | | CLN00496840_frag25 | PQTTCI |

TABLE 4-continued

| FP ID | SEQ. ID. NO. (N1) | SEQ. ID. NO. (P1) | SEQ. ID. NO. (N0) | Source ID | Sequence |
|---|---|---|---|---|---|
| HG1020045 | | SEQ. ID. NO.: 137 | | CLN00496840_frag26 | QTTCIP |
| HG1020046 | | SEQ. ID. NO.: 138 | | CLN00496840_frag27 | TTCIPV |
| HG1020047 | | SEQ. ID. NO.: 139 | | CLN00496840_frag28 | TCIPVS |
| HG1020048 | | SEQ. ID. NO.: 140 | | CLN00496840_frag29 | CIPVSH |
| HG1020049 | | SEQ. ID. NO.: 141 | | CLN00496840_frag30 | IPVSHL |
| HG1020050 | | SEQ. ID. NO.: 142 | | CLN00496840_frag31 | PVSHLK |
| HG1020051 | | SEQ. ID. NO.: 143 | | CLN00496840_frag32 | VSHLKG |
| HG1020052 | | SEQ. ID. NO.: 144 | | CLN00496840_frag33 | SHLKGE |
| HG1020053 | | SEQ. ID. NO.: 145 | | CLN00496840_frag34 | HLKGEM |
| HG1020054 | | SEQ. ID. NO.: 146 | | CLN00496840_frag35 | LKGEMV |
| HG1020055 | | SEQ. ID. NO.: 147 | | CLN00496840_frag36 | KGEMVI |
| HG1020068 | SEQ. ID. NO.: 108 | SEQ. ID. NO.: 148 | | CLN00496840_frag37 | (1-21) |
| HG1020069 | | SEQ. ID. NO.: 149 | | CLN00496840_frag38 | MFLPSH |
| HG1020070 | | SEQ. ID. NO.: 150 | | CLN00496840_frag39 | FLPSHT |
| HG1020071 | | SEQ. ID. NO.: 151 | | CLN00496840_frag40 | LPSHTQ |
| HG1020072 | | SEQ. ID. NO.: 152 | | CLN00496840_frag41 | PSHTQD |
| HG1020073 | | SEQ. ID. NO.: 153 | | CLN00496840_frag42 | SHTQDS |
| HG1020074 | | SEQ. ID. NO.: 154 | | CLN00496840_frag43 | HTQDSL |
| HG1020075 | | SEQ. ID. NO.: 155 | | CLN00496840_frag44 | TQDSLV |
| HG1020076 | | SEQ. ID. NO.: 156 | | CLN00496840_frag45 | QDSLVK |
| HG1020077 | | SEQ. ID. NO.: 157 | | CLN00496840_frag46 | DSLVKL |
| HG1020078 | | SEQ. ID. NO.: 158 | | CLN00496840_frag47 | SLVKLK |
| HG1020079 | | SEQ. ID. NO.: 159 | | CLN00496840_frag48 | LVKLKG |
| HG1020080 | | SEQ. ID. NO.: 160 | | CLN00496840_frag49 | VKLKGK |
| HG1020081 | | SEQ. ID. NO.: 161 | | CLN00496840_frag50 | KLKGKF |
| HG1020082 | | SEQ. ID. NO.: 162 | | CLN00496840_frag51 | LKGKFK |
| HG1020083 | | SEQ. ID. NO.: 163 | | CLN00496840_frag52 | KGKFKL |
| HG1020084 | | SEQ. ID. NO.: 164 | | CLN00496840_frag53 | GKFKLS |
| HG1020056 | SEQ. ID. NO.: 109 | SEQ. ID. NO.: 165 | SEQ. ID. NO.:: 178 | chimp_prediction | |
| HG1020057 | SEQ. ID. NO.: 110 | SEQ. ID. NO.: 166 | | chimp_frag1 | (45-84) |
| HG1020058 | | SEQ. ID. NO.: 167 | | chimp_frag2 | LLSYSP |
| HG1020059 | | SEQ. ID. NO.: 168 | | chimp_frag3 | LSYSPA |
| HG1020060 | | SEQ. ID. NO.: 169 | | chimp_frag4 | SYSPAR |
| HG1020061 | | SEQ. ID. NO.: 170 | | chimp_frag5 | YSPARK |
| HG1020062 | | SEQ. ID. NO.: 171 | | chimp_frag6 | CIISSR |
| HG1020063 | | SEQ. ID. NO.: 172 | | chimp_frag7 | IISSRP |
| HG1020064 | | SEQ. ID. NO.: 173 | | chimp_frag8 | ISSRPQ |
| HG1020065 | | SEQ. ID. NO.: 174 | | chimp_frag9 | SSRPQT |

TABLE 4-continued

| FP ID | SEQ. ID. NO. (N1) | SEQ. ID. NO. (P1) | SEQ. ID. NO. (N0) | Source ID | Sequence |
|---|---|---|---|---|---|
| HG1020066 | | SEQ. ID. NO.: 175 | | chimp_frag10 | SRPQTT |
| HG1020067 | | SEQ. ID. NO.: 176 | | chimp_frag11 | RPQTTC |

TABLE 5

| FP ID | SEQ. ID. NO. (P1) | Source ID | Predicted Protein Length | TM | TM Domain | Non-TM Domains |
|---|---|---|---|---|---|---|
| HG1020019 | SEQ. ID. NO.: 111 | CLN00496840.a | 84 | 1 | (22-44) | (1-21) (45-84) |

TABLE 6

| Cancer Type | Rank Within Cancer | Log p-Value | Distance to Amplicon |
|---|---|---|---|
| stomach | 22 | −18.3119 | 107522 |
| prostate | 21 | −9.6372 | 657522 |
| breast infiltrating ductile carcinoma | 6 | −90 | 742478 |
| ovarian | 18 | −17.9238 | 792478 |

TABLE 7

| FP ID | SEQ. ID. NO. (N1) | SEQ. ID. NO. (P1) | SEQ. ID. NO. (N0) | Source ID | Sequence |
|---|---|---|---|---|---|
| HG1020089 | SEQ. ID. NO.: 179 | SEQ. ID. NO.: 185 | | CLN00156137.a | (FL) |
| HG1020194 | | SEQ. ID. NO.: 186 | | CLN00156137.a_frag1 | MVITKE |
| HG1020195 | | SEQ. ID. NO.: 187 | | CLN00156137.a_frag2 | VITKEV |
| HG1020196 | | SEQ. ID. NO.: 188 | | CLN00156137.a_frag3 | ITKEVT |
| HG1020197 | | SEQ. ID. NO.: 189 | | CLN00156137.a_frag4 | TKEVTP |
| HG1020198 | | SEQ. ID. NO.: 190 | | CLN00156137.a_frag5 | KEVTPK |
| HG1020199 | | SEQ. ID. NO.: 191 | | CLN00156137.a_frag6 | EVTPKV |
| HG1020200 | | SEQ. ID. NO.: 192 | | CLN00156137.a_frag7 | VTPKVI |
| HG1020201 | | SEQ. ID. NO.: 193 | | CLN00156137.a_frag8 | TPKVIC |
| HG1020202 | | SEQ. ID. NO.: 194 | | CLN00156137.a_frag9 | PKVICA |
| HG1020203 | | SEQ. ID. NO.: 195 | | CLN00156137.a_frag10 | KVICAS |
| HG1020204 | | SEQ. ID. NO.: 196 | | CLN00156137.a_frag11 | VICASS |
| HG1020205 | | SEQ. ID. NO.: 197 | | CLN00156137.a_frag12 | ICASSW |
| HG1020206 | | SEQ. ID. NO.: 198 | | CLN00156137.a_frag13 | CASSWA |

TABLE 7-continued

| FP ID | SEQ. ID. NO. (N1) | SEQ. ID. NO. (P1) | SEQ. ID. NO. (N0) | Source ID | Sequence |
|---|---|---|---|---|---|
| HG1020207 | | SEQ. ID. NO.: 199 | | CLN00156137.a_frag14 | ASSWAV |
| HG1020208 | | SEQ. ID. NO.: 200 | | CLN00156137.a_frag15 | SSWAVY |
| HG1020209 | | SEQ. ID. NO.: 201 | | CLN00156137.a_frag16 | SWAVYH |
| HG1020210 | | SEQ. ID. NO.: 202 | | CLN00156137.a_frag17 | WAVYHS |
| HG1020211 | | SEQ. ID. NO.: 203 | | CLN00156137.a_frag18 | AVYHSL |
| HG1020212 | | SEQ. ID. NO.: 204 | | CLN00156137.a_frag19 | VYHSLC |
| HG1020213 | | SEQ. ID. NO.: 205 | | CLN00156137.a_frag20 | YHSLCM |
| HG1020214 | | SEQ. ID. NO.: 206 | | CLN00156137.a_frag21 | HSLCMQ |
| HG1020215 | | SEQ. ID. NO.: 207 | | CLN00156137.a_frag22 | SLCMQG |
| HG1020216 | | SEQ. ID. NO.: 208 | | CLN00156137.a_frag23 | LCMQGA |
| HG1020217 | | SEQ. ID. NO.: 209 | | CLN00156137.a_frag24 | CMQGAC |
| HG1020218 | | SEQ. ID. NO.: 210 | | CLN00156137.a_frag25 | MQGACV |
| HG1020219 | | SEQ. ID. NO.: 211 | | CLN00156137.a_frag26 | QGACVP |
| HG1020220 | | SEQ. ID. NO.: 212 | | CLN00156137.a_frag27 | GACVPR |
| HG1020221 | | SEQ. ID. NO.: 213 | | CLN00156137.a_frag28 | ACVPRS |
| HG1020222 | | SEQ. ID. NO.: 214 | | CLN00156137.a_frag29 | CVPRSL |
| HG1020223 | | SEQ. ID. NO.: 215 | | CLN00156137.a_frag30 | VPRSLC |
| HG1020224 | | SEQ. ID. NO.: 216 | | CLN00156137.a_frag31 | PRSLCM |
| HG1020225 | | SEQ. ID. NO.: 217 | | CLN00156137.a_frag32 | RSLCMY |
| HG1020226 | | SEQ. ID. NO.: 218 | | CLN00156137.a_frag33 | SLCMYR |
| HG1020227 | | SEQ. ID. NO.: 219 | | CLN00156137.a_frag34 | LCMYRA |
| HG1020228 | | SEQ. ID. NO.: 220 | | CLN00156137.a_frag35 | CMYRAC |
| HG1020229 | | SEQ. ID. NO.: 221 | | CLN00156137.a_frag36 | MYRACV |
| HG1020230 | | SEQ. ID. NO.: 222 | | CLN00156137.a_frag37 | YRACVP |
| HG1020231 | | SEQ. ID. NO.: 223 | | CLN00156137.a_frag38 | RACVPK |
| HG1020232 | | SEQ. ID. NO.: 224 | | CLN00156137.a_frag39 | ACVPKA |

TABLE 7-continued

| FP ID | SEQ. ID. NO. (N1) | SEQ. ID. NO. (P1) | SEQ. ID. NO. (N0) | Source ID | Sequence |
|---|---|---|---|---|---|
| HG1020233 | | SEQ. ID. NO.: 225 | | CLN00156137.a_frag40 | CVPKAC |
| HG1020234 | | SEQ. ID. NO.: 226 | | CLN00156137.a_frag41 | VPKACV |
| HG1020235 | | SEQ. ID. NO.: 227 | | CLN00156137.a_frag42 | PKACVS |
| HG1020236 | | SEQ. ID. NO.: 228 | | CLN00156137.a_frag43 | KACVSG |
| HG1020237 | | SEQ. ID. NO.: 229 | | CLN00156137.a_frag44 | ACVSGL |
| HG1020238 | | SEQ. ID. NO.: 230 | | CLN00156137.a_frag45 | CVSGLC |
| HG1020239 | | SEQ. ID. NO.: 231 | | CLN00156137.a_frag46 | VSGLCV |
| HG1020240 | | SEQ. ID. NO.: 232 | | CLN00156137.a_frag47 | SGLCVK |
| HG1020241 | | SEQ. ID. NO.: 233 | | CLN00156137.a_frag48 | GLCVKP |
| HG1020242 | | SEQ. ID. NO.: 234 | | CLN00156137.a_frag49 | LCVKPV |
| HG1020243 | | SEQ. ID. NO.: 235 | | CLN00156137.a_frag50 | CVKPVY |
| HG1020244 | | SEQ. ID. NO.: 236 | | CLN00156137.a_frag51 | VKPVYV |
| HG1020245 | | SEQ. ID. NO.: 237 | | CLN00156137.a_frag52 | KPVYVL |
| HG1020246 | | SEQ. ID. NO.: 238 | | CLN00156137.a_frag53 | PVYVLG |
| HG1020247 | | SEQ. ID. NO.: 239 | | CLN00156137.a_frag54 | VYVLGL |
| HG1020248 | | SEQ. ID. NO.: 240 | | CLN00156137.a_frag55 | YVLGLH |
| HG1020249 | | SEQ. ID. NO.: 241 | | CLN00156137.a_frag56 | VLGLHA |
| HG1020250 | | SEQ. ID. NO.: 242 | | CLN00156137.a_frag57 | LGLHAQ |
| HG1020251 | | SEQ. ID. NO.: 243 | | CLN00156137.a_frag58 | GLHAQS |
| HG1020252 | | SEQ. ID. NO.: 244 | | CLN00156137.a_frag59 | LHAQSL |
| HG1020253 | | SEQ. ID. NO.: 245 | | CLN00156137.a_frag60 | HAQSLY |
| HG1020254 | | SEQ. ID. NO.: 246 | | CLN00156137.a_frag61 | AQSLYV |
| HG1020255 | | SEQ. ID. NO.: 247 | | CLN00156137.a_frag62 | QSLYVR |
| HG1020256 | | SEQ. ID. NO.: 248 | | CLN00156137.a_frag63 | SLYVRP |
| HG1020257 | | SEQ. ID. NO.: 249 | | CLN00156137.a_frag64 | LYVRPV |

TABLE 7-continued

| FP ID | SEQ. ID. NO. (N1) | SEQ. ID. NO. (P1) | SEQ. ID. NO. (N0) | Source ID | Sequence |
|---|---|---|---|---|---|
| HG1020258 | | SEQ. ID. NO.: 250 | | CLN00156137.a_frag65 | YVRPVC |
| HG1020259 | | SEQ. ID. NO.: 251 | | CLN00156137.a_frag66 | VRPVCQ |
| HG1020260 | | SEQ. ID. NO.: 252 | | CLN00156137.a_frag67 | RPVCQT |
| HG1020261 | | SEQ. ID. NO.: 253 | | CLN00156137.a_frag68 | PVCQTC |
| HG1020262 | | SEQ. ID. NO.: 254 | | CLN00156137.a_frag69 | VCQTCG |
| HG1020263 | | SEQ. ID. NO.: 255 | | CLN00156137.a_frag70 | CQTCGS |
| HG1020264 | | SEQ. ID. NO.: 256 | | CLN00156137.a_frag71 | QTCGSN |
| HG1020265 | | SEQ. ID. NO.: 257 | | CLN00156137.a_frag72 | TCGSNL |
| HG1020266 | | SEQ. ID. NO.: 258 | | CLN00156137.a_frag73 | CGSNLC |
| HG1020267 | | SEQ. ID. NO.: 259 | | CLN00156137.a_frag74 | GSNLCV |
| HG1020268 | | SEQ. ID. NO.: 260 | | CLN00156137.a_frag75 | SNLCVQ |
| HG1020269 | | SEQ. ID. NO.: 261 | | CLN00156137.a_frag76 | NLCVQG |
| HG1020270 | | SEQ. ID. NO.: 262 | | CLN00156137.a_frag77 | LCVQGI |
| HG1020271 | | SEQ. ID. NO.: 263 | | CLN00156137.a_frag78 | CVQGIC |
| HG1020272 | | SEQ. ID. NO.: 264 | | CLN00156137.a_frag79 | VQGICL |
| HG1020273 | | SEQ. ID. NO.: 265 | | CLN00156137.a_frag80 | QGICLV |
| HG1020274 | | SEQ. ID. NO.: 266 | | CLN00156137.a_frag81 | GICLVW |
| HG1020275 | | SEQ. ID. NO.: 267 | | CLN00156137.a_frag82 | ICLVWP |
| HG1020276 | | SEQ. ID. NO.: 268 | | CLN00156137.a_frag83 | CLVWPR |
| HG1020277 | | SEQ. ID. NO.: 269 | | CLN00156137.a_frag84 | LVWPRG |
| HG1020278 | | SEQ. ID. NO.: 270 | | CLN00156137.a_frag85 | VWPRGW |
| HG1020279 | | SEQ. ID. NO.: 271 | | CLN00156137.a_frag86 | WPRGWS |
| HG1020280 | | SEQ. ID. NO.: 272 | | CLN00156137.a_frag87 | PRGWSV |
| HG1020281 | | SEQ. ID. NO.: 273 | | CLN00156137.a_frag88 | RGWSVR |
| HG1020282 | | SEQ. ID. NO.: 274 | | CLN00156137.a_frag89 | GWSVRY |
| HG1020283 | | SEQ. ID. NO.: 275 | | CLN00156137.a_frag90 | WSVRYI |

TABLE 7-continued

| FP ID | SEQ. ID. NO. (N1) | SEQ. ID. NO. (P1) | SEQ. ID. NO. (N0) | Source ID | Sequence |
|---|---|---|---|---|---|
| HG1020284 | | SEQ. ID. NO.: 276 | | CLN00156137.a_frag91 | SVRYIW |
| HG1020285 | | SEQ. ID. NO.: 277 | | CLN00156137.a_frag92 | VRYIWM |
| HG1020286 | | SEQ. ID. NO.: 278 | | CLN00156137.a_frag93 | RYIWMC |
| HG1020287 | | SEQ. ID. NO.: 279 | | CLN00156137.a_frag94 | YIWMCF |
| HG1020288 | | SEQ. ID. NO.: 280 | | CLN00156137.a_frag95 | IWMCFG |
| HG1020289 | | SEQ. ID. NO.: 281 | | CLN00156137.a_frag96 | WMCFGQ |
| HG1020290 | | SEQ. ID. NO.: 282 | | CLN00156137.a_frag97 | MCFGQG |
| HG1020291 | | SEQ. ID. NO.: 283 | | CLN00156137.a_frag98 | CFGQGT |
| HG1020292 | | SEQ. ID. NO.: 284 | | CLN00156137.a_frag99 | FGQGTG |
| HG1020293 | | SEQ. ID. NO.: 285 | | CLN00156137.a_frag100 | GQGTGR |
| HG1020294 | | SEQ. ID. NO.: 286 | | CLN00156137.a_frag101 | QGTGRG |
| HG1020295 | | SEQ. ID. NO.: 287 | | CLN00156137.a_frag102 | GTGRGG |
| HG1020296 | | SEQ. ID. NO.: 288 | | CLN00156137.a_frag103 | TGRGGY |
| HG1020297 | | SEQ. ID. NO.: 289 | | CLN00156137.a_frag104 | GRGGYP |
| HG1020298 | | SEQ. ID. NO.: 290 | | CLN00156137.a_frag105 | RGGYPR |
| HG1020299 | | SEQ. ID. NO.: 291 | | CLN00156137.a_frag106 | GGYPRP |
| HG1020300 | | SEQ. ID. NO.: 292 | | CLN00156137.a_frag107 | GYPRPA |
| HG1020301 | SEQ. ID. NO.: 180 | SEQ. ID. NO.: 293 | | CLN00156137.a_frag108 | GQGTGRGGYPRP |
| HG1020090 | SEQ. ID. NO.: 181 | SEQ. ID. NO.: 294 | | CLN00156137.b | (FL) |
| HG1020302 | SEQ. ID. NO.: 182 | SEQ. ID. NO.: 295 | | CLN00156137.b_frag1 | MCLTYLKTFWGWM FCTAWQLYCLSRTC RPLDNGTGTSCPES QE |
| HG1020303 | SEQ. ID. NO.: 183 | SEQ. ID. NO.: 296 | | CLN00156137.b_frag2 | EMESCSVAQAGVQ GTISAPCDLRHLGS SNSPASAS |
| HG1020304 | SEQ. ID. NO.: 184 | SEQ. ID. NO.: 297 | | CLN00156137.b_frag3 | RTCRPLDNGTGTSC PESQEQ |
| HG1020305 | | SEQ. ID. NO.: 298 | | CLN00156137.b_frag4 | MCLTYL |
| HG1020306 | | SEQ. ID. NO.: 299 | | CLN00156137.b_frag5 | CLTYLK |

TABLE 7-continued

| FP ID | SEQ. ID. NO. (N1) | SEQ. ID. NO. (P1) | SEQ. ID. NO. (N0) | Source ID | Sequence |
|---|---|---|---|---|---|
| HG1020307 | | SEQ. ID. NO.: 300 | | CLN00156137.b_frag6 | LTYLKT |
| HG1020308 | | SEQ. ID. NO.: 301 | | CLN00156137.b_frag7 | TYLKTF |
| HG1020309 | | SEQ. ID. NO.: 302 | | CLN00156137.b_frag8 | YLKTFW |
| HG1020310 | | SEQ. ID. NO.: 303 | | CLN00156137.b_frag9 | LKTFWG |
| HG1020311 | | SEQ. ID. NO.: 304 | | CLN00156137.b_frag10 | KTFWGW |
| HG1020312 | | SEQ. ID. NO.: 305 | | CLN00156137.b_frag11 | TFWGWM |
| HG1020313 | | SEQ. ID. NO.: 306 | | CLN00156137.b_frag12 | FWGWMF |
| HG1020314 | | SEQ. ID. NO.: 307 | | CLN00156137.b_frag13 | WGWMFC |
| HG1020315 | | SEQ. ID. NO.: 308 | | CLN00156137.b_frag14 | GWMFCT |
| HG1020316 | | SEQ. ID. NO.: 309 | | CLN00156137.b_frag15 | WMFCTA |
| HG1020317 | | SEQ. ID. NO.: 310 | | CLN00156137.b_frag16 | MFCTAW |
| HG1020318 | | SEQ. ID. NO.: 311 | | CLN00156137.b_frag17 | FCTAWQ |
| HG1020319 | | SEQ. ID. NO.: 312 | | CLN00156137.b_frag18 | CTAWQL |
| HG1020320 | | SEQ. ID. NO.: 313 | | CLN00156137.b_frag19 | TAWQLY |
| HG1020321 | | SEQ. ID. NO.: 314 | | CLN00156137.b_frag20 | AWQLYC |
| HG1020322 | | SEQ. ID. NO.: 315 | | CLN00156137.b_frag21 | WQLYCL |
| HG1020323 | | SEQ. ID. NO.: 316 | | CLN00156137.b_frag22 | QLYCLS |
| HG1020324 | | SEQ. ID. NO.: 317 | | CLN00156137.b_frag23 | LYCLSR |
| HG1020325 | | SEQ. ID. NO.: 318 | | CLN00156137.b_frag24 | YCLSRT |
| HG1020326 | | SEQ. ID. NO.: 319 | | CLN00156137.b_frag25 | CLSRTC |
| HG1020327 | | SEQ. ID. NO.: 320 | | CLN00156137.b_frag26 | LSRTCR |
| HG1020328 | | SEQ. ID. NO.: 321 | | CLN00156137.b_frag27 | SRTCRP |
| HG1020329 | | SEQ. ID. NO.: 322 | | CLN00156137.b_frag28 | RTCRPL |
| HG1020330 | | SEQ. ID. NO.: 323 | | CLN00156137.b_frag29 | TCRPLD |
| HG1020331 | | SEQ. ID. NO.: 324 | | CLN00156137.b_frag30 | CRPLDN |
| HG1020332 | | SEQ. ID. NO.: 325 | | CLN00156137.b_frag31 | RPLDNG |

TABLE 7-continued

| FP ID | SEQ. ID. NO. (N1) | SEQ. ID. NO. (P1) | SEQ. ID. NO. (N0) | Source ID | Sequence |
| --- | --- | --- | --- | --- | --- |
| HG1020333 | | SEQ. ID. NO.: 326 | | CLN00156137.b_frag32 | PLDNGT |
| HG1020334 | | SEQ. ID. NO.: 327 | | CLN00156137.b_frag33 | LDNGTG |
| HG1020335 | | SEQ. ID. NO.: 328 | | CLN00156137.b_frag34 | DNGTGT |
| HG1020336 | | SEQ. ID. NO.: 329 | | CLN00156137.b_frag35 | NGTGTS |
| HG1020337 | | SEQ. ID. NO.: 330 | | CLN00156137.b_frag36 | GTGTSC |
| HG1020338 | | SEQ. ID. NO.: 331 | | CLN00156137.b_frag37 | TGTSCP |
| HG1020339 | | SEQ. ID. NO.: 332 | | CLN00156137.b_frag38 | GTSCPE |
| HG1020340 | | SEQ. ID. NO.: 333 | | CLN00156137.b_frag39 | TSCPES |
| HG1020341 | | SEQ. ID. NO.: 334 | | CLN00156137.b_frag40 | SCPESQ |
| HG1020342 | | SEQ. ID. NO.: 335 | | CLN00156137.b_frag41 | CPESQE |
| HG1020343 | | SEQ. ID. NO.: 336 | | CLN00156137.b_frag42 | PESQEQ |
| HG1020344 | | SEQ. ID. NO.: 337 | | CLN00156137.b_frag43 | EMESCS |
| HG1020345 | | SEQ. ID. NO.: 338 | | CLN00156137.b_frag44 | MESCSV |
| HG1020346 | | SEQ. ID. NO.: 339 | | CLN00156137.b_frag45 | ESCSVA |
| HG1020347 | | SEQ. ID. NO.: 340 | | CLN00156137.b_frag46 | SCSVAQ |
| HG1020348 | | SEQ. ID. NO.: 341 | | CLN00156137.b_frag47 | CSVAQA |
| HG1020349 | | SEQ. ID. NO.: 342 | | CLN00156137.b_frag48 | SVAQAG |
| HG1020350 | | SEQ. ID. NO.: 343 | | CLN00156137.b_frag49 | VAQAGV |
| HG1020351 | | SEQ. ID. NO.: 344 | | CLN00156137.b_frag50 | AQAGVQ |
| HG1020352 | | SEQ. ID. NO.: 345 | | CLN00156137.b_frag51 | QAGVQG |
| HG1020353 | | SEQ. ID. NO.: 346 | | CLN00156137.b_frag52 | AGVQGT |
| HG1020354 | | SEQ. ID. NO.: 347 | | CLN00156137.b_frag53 | GVQGTI |
| HG1020355 | | SEQ. ID. NO.: 348 | | CLN00156137.b_frag54 | VQGTIS |
| HG1020356 | | SEQ. ID. NO.: 349 | | CLN00156137.b_frag55 | QGTISA |
| HG1020357 | | SEQ. ID. NO.: 350 | | CLN00156137.b_frag56 | GTISAP |

TABLE 7-continued

| FP ID | SEQ. ID. NO. (N1) | SEQ. ID. NO. (P1) | SEQ. ID. NO. (N0) | Source ID | Sequence |
|---|---|---|---|---|---|
| HG1020358 | | SEQ. ID. NO.: 351 | | CLN00156137.b_frag57 | TISAPC |
| HG1020359 | | SEQ. ID. NO.: 352 | | CLN00156137.b_frag58 | ISAPCD |
| HG1020360 | | SEQ. ID. NO.: 353 | | CLN00156137.b_frag59 | SAPCDL |
| HG1020361 | | SEQ. ID. NO.: 354 | | CLN00156137.b_frag60 | APCDLR |
| HG1020362 | | SEQ. ID. NO.: 355 | | CLN00156137.b_frag61 | PCDLRH |
| HG1020363 | | SEQ. ID. NO.: 356 | | CLN00156137.b_frag62 | CDLRHL |
| HG1020364 | | SEQ. ID. NO.: 357 | | CLN00156137.b_frag63 | DLRHLG |
| HG1020365 | | SEQ. ID. NO.: 358 | | CLN00156137.b_frag64 | LRHLGS |
| HG1020366 | | SEQ. ID. NO.: 359 | | CLN00156137.b_frag65 | RHLGSS |
| HG1020367 | | SEQ. ID. NO.: 360 | | CLN00156137.b_frag66 | HLGSSN |
| HG1020368 | | SEQ. ID. NO.: 361 | | CLN00156137.b_frag67 | LGSSNS |
| HG1020369 | | SEQ. ID. NO.: 362 | | CLN00156137.b_frag68 | GSSNSP |
| HG1020370 | | SEQ. ID. NO.: 363 | | CLN00156137.b_frag69 | SSNSPA |
| HG1020371 | | SEQ. ID. NO.: 364 | | CLN00156137.b_frag70 | SNSPAS |
| HG1020372 | | SEQ. ID. NO.: 365 | | CLN00156137.b_frag71 | NSPASA |
| HG1020373 | | SEQ. ID. NO.: 366 | | CLN00156137.b_frag72 | SPASAS |

TABLE 8

| FP ID | Source ID | Pred Prot Length | Tree-vote | Signal Peptide Coords | Mature Protein Domains | TM Domain | non-TM Domains |
|---|---|---|---|---|---|---|---|
| HG1020089 | CLN00156137.a | 112 | 0.01 | 23-48 | 49-112 | N/A | 1-112 |
| HG1020090 | CLN00156137.b | 101 | 0.52 | 9-22 | 23-101 | 44-66 | 1-43 67-101 |

---

What is claimed is:

1. An isolated antibody that binds to a polypeptide consisting of the amino acid sequence of SEQ ID NO: 185.

2. The isolated antibody of claim 1, wherein the isolated antibody is a single chain antibody.

3. The isolated antibody of claim 1, wherein the isolated antibody has been humanized.

4. The isolated antibody of claim 1, wherein the isolated antibody is a human antibody.

5. An isolated antibody fragment that binds to a polypeptide consisting of the amino acid sequence of SEQ ID NO: 185.

6. The isolated antibody fragment of claim 5, wherein the isolated antibody fragment is an Fab, and F(ab')2 or an Fv.

\* \* \* \* \*

UNITED STATES PATENT AND TRADEMARK OFFICE
CERTIFICATE OF CORRECTION

PATENT NO. : 8,404,810 B2  Page 1 of 1
APPLICATION NO. : 12/279703
DATED : March 26, 2013
INVENTOR(S) : Hestir et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1198 days.

Signed and Sealed this
First Day of September, 2015

Michelle K. Lee
*Director of the United States Patent and Trademark Office*